United States Patent
Kato et al.

(10) Patent No.: US 11,538,863 B2
(45) Date of Patent: Dec. 27, 2022

(54) PHOTOELECTRIC CONVERSION DEVICE AND IMAGING APPARATUS

(71) Applicants: Sony Corporation, Tokyo (JP); SONY SEMICONDUCTOR SOLUTIONS CORPORATION, Kanagawa (JP)

(72) Inventors: Yu Kato, Kanagawa (JP); Yuta Inaba, Kanagawa (JP); Masato Kanno, Kanagawa (JP); Hideaki Mogi, Kanagawa (JP); Miki Kimijima, Kanagawa (JP); Sae Miyaji, Kanagawa (JP)

(73) Assignees: Sony Corporation, Tokyo (JP); Sony Semiconductor Solutions Corporation, Kanagawa (JP)

( * ) Notice: Subject to any disclaimer, the term of this patent is extended or adjusted under 35 U.S.C. 154(b) by 355 days.

(21) Appl. No.: 16/648,981

(22) PCT Filed: Sep. 7, 2018

(86) PCT No.: PCT/JP2018/033173
§ 371 (c)(1),
(2) Date: Mar. 19, 2020

(87) PCT Pub. No.: WO2019/058995
PCT Pub. Date: Mar. 28, 2019

(65) Prior Publication Data
US 2020/0295088 A1      Sep. 17, 2020

(30) Foreign Application Priority Data
Sep. 20, 2017   (JP) .............................. JP2017-180653

(51) Int. Cl.
*H01L 27/30*   (2006.01)
*H01L 51/00*   (2006.01)

(52) U.S. Cl.
CPC ........ *H01L 27/307* (2013.01); *H01L 51/0046* (2013.01); *H01L 51/0067* (2013.01); *H01L 51/0074* (2013.01); *H01L 51/0077* (2013.01)

(58) Field of Classification Search
CPC ............... H01L 27/307; H01L 51/0046; H01L 51/0067
(Continued)

(56) References Cited

U.S. PATENT DOCUMENTS

2007/0262303 A1   11/2007 Yan et al.
2009/0044863 A1   2/2009  Marder
(Continued)

FOREIGN PATENT DOCUMENTS

EP    3432376 A1     1/2019
JP    2005-303266 A  10/2005
(Continued)

OTHER PUBLICATIONS

International Search Report issued in connection with International Patent Application No. PCT/JP2018/033173, dated Oct. 23, 2018. (1 page).
(Continued)

*Primary Examiner* — Quoc D Hoang
(74) *Attorney, Agent, or Firm* — K&L Gates LLP

(57) ABSTRACT

[Problem] Provided are a photoelectric conversion device and an imaging apparatus capable of improving quantum efficiency and a response speed.
[Solving means] A first photoelectric conversion device according to one embodiment of the present disclosure includes a first electrode, a second electrode opposed to the first electrode, and a photoelectric conversion layer. The photoelectric conversion layer is provided between the first electrode and the second electrode and includes at least one type of one organic semiconductor material having crystal-
(Continued)

linity. Variation in a ratio between horizontally-oriented crystal and vertically-oriented crystal in the photoelectric conversion layer is three times or less between a case where film formation of the one organic semiconductor material is performed at a first temperature and a case where the film formation of the one organic semiconductor material is performed at a second temperature. The second temperature is higher than the first temperature.

21 Claims, 31 Drawing Sheets

(58) Field of Classification Search
USPC .......................................... 428/690; 257/307
See application file for complete search history.

(56) References Cited

U.S. PATENT DOCUMENTS

| 2016/0197281 | A1* | 7/2016 | Momose ............ H01L 51/0028 438/82 |
| 2017/0040550 | A1 | 2/2017 | Yakushiji |
| 2017/0069851 | A1 | 3/2017 | Takasu |

FOREIGN PATENT DOCUMENTS

| JP | 2007-059457 A | 3/2007 |
| JP | 2008-258421 A | 10/2008 |
| JP | 2009-060053 A | 1/2012 |
| JP | 2012-009910 A | 1/2012 |
| WO | WO-2016156546 A1 | 10/2016 |
| WO | WO-2017014146 A | 1/2017 |
| WO | WO-2017033736 A1 | 3/2017 |
| WO | 2017/122538 A1 | 7/2017 |

OTHER PUBLICATIONS

Dadvand, Afshin et al., "Heterocirculenes as a new class of organic semiconductors", Chem. Commun., 2008, pp. 5354-5356 in particular, p. 1, left column.

Myeong Jin Kang et al:"Diphenyl Derivatives of Dinaphtho[2,3-b:2',3 1'-f] thieno[3,2- b]thiophene: Organic Semiconductors for Thermally Stable Thin-Film Transistors ", ACS Applied Materials & Interfaces, vol. 5, No. 7, Feb. 14, 2013 (Feb. 14, 2013), pp. 2331-2336, XP055735801, US ISSN: 1944-8244, DOI: 10.1021/am3026163 *figure 1; table 2 ** p. 2334, col. 2, line 18—p. 2335, col. 1, l i ne 3 *.

Kazuaki Oniwa et al: "Single crystal biphenyl end-capped furan-incorporated oligomers: influence of unusual packing structure on carrier mobility and luminescence", Journal of Materials Chemistry C, vol. 1, No. 26, Apr. 29, 2013 (Apr. 29, 2013) , p. 4163, XP055733470, GB ISSN: 2050-7526, DOI: 10.1039/c3tc30220b *Scheme 1; p. 4164 p. 4163, col. 1, line 8-line9 p. 4164, col. 2, line6—p. 4165, col. 1, l i ne 12  p. 4167, col. 2, line33-line44p. 4167, col. 1, line 21-line22*.

Hoji Shinamura et al: "Linear- and Angular-Shaped Naphthodithiophenes: Selective Synthesis, Properties, and Application to Organic Field-Effect Transistors" , Journal of the Amer i can Chem i cal Soc! ety, vol. 133, No. 13, Apr. 6, 2011 (Apr. 6, 2011), pp. 5024-5035, XP055011617, ISSN: 0002-7863, DOI:10.1021/ja110973m * p. 5024, col. 1, line 5  figures 8, 10; compounds 1(c), 2(c), 3(c), 4(c)  p. 5027,col. 1, line 14p. 5029, col. 2, line6-line8;figures 8, 9p. 5032, col. 1, line6-line8**.

* cited by examiner

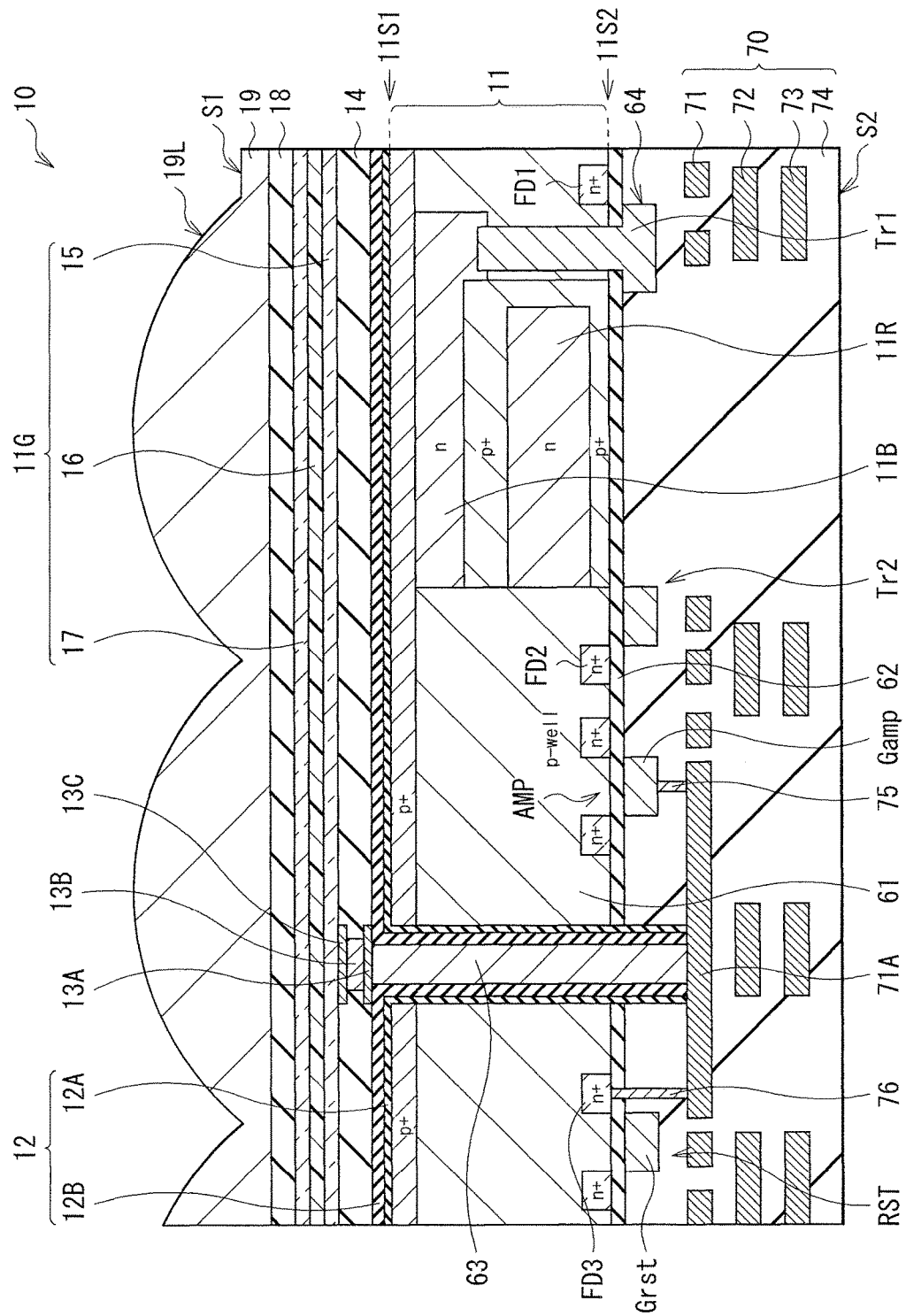
[FIG. 1]

[FIG. 2]
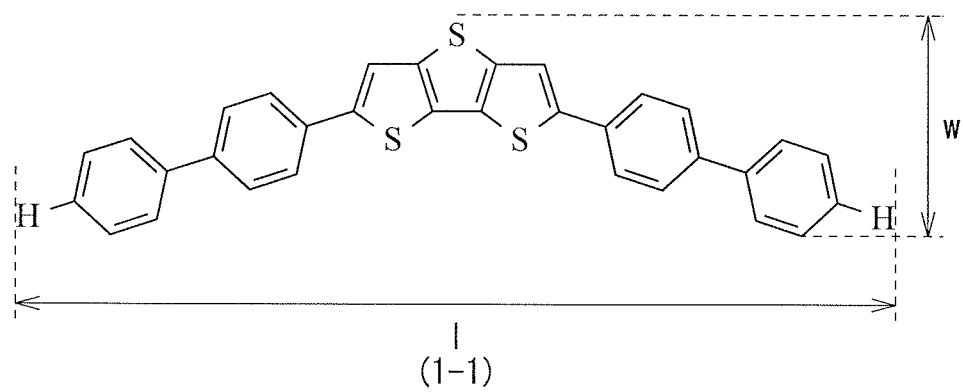
(1-1)
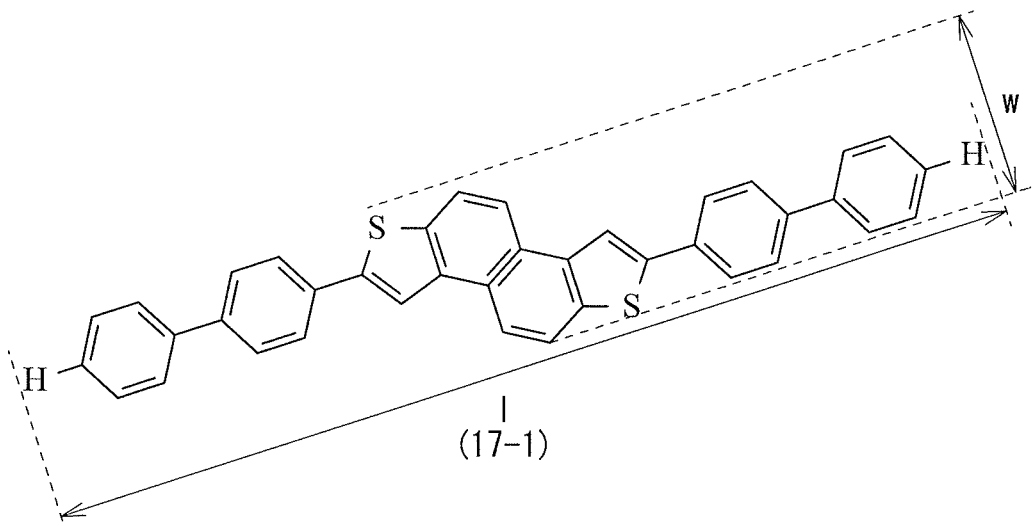
(17-1)

[FIG. 3]
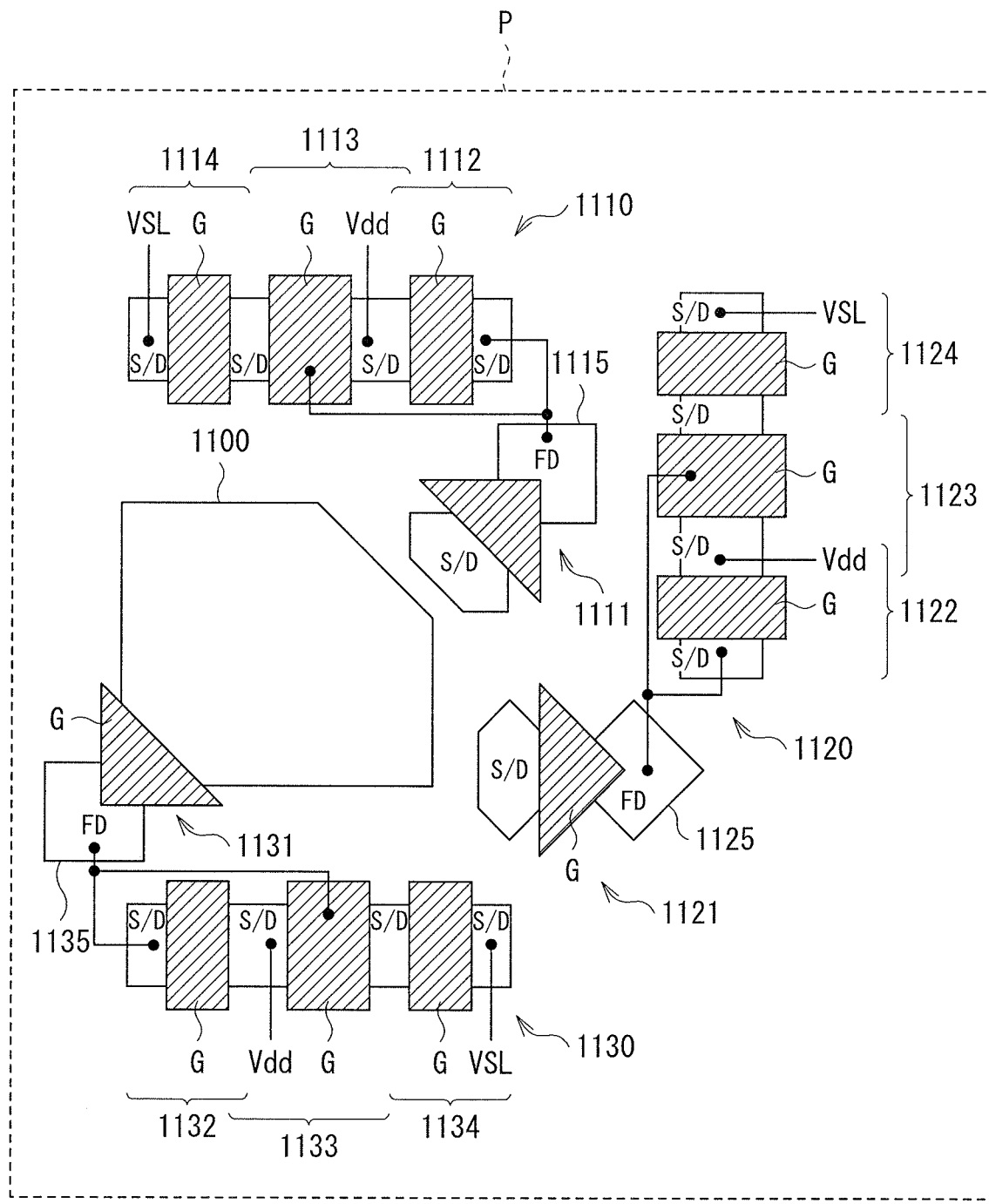

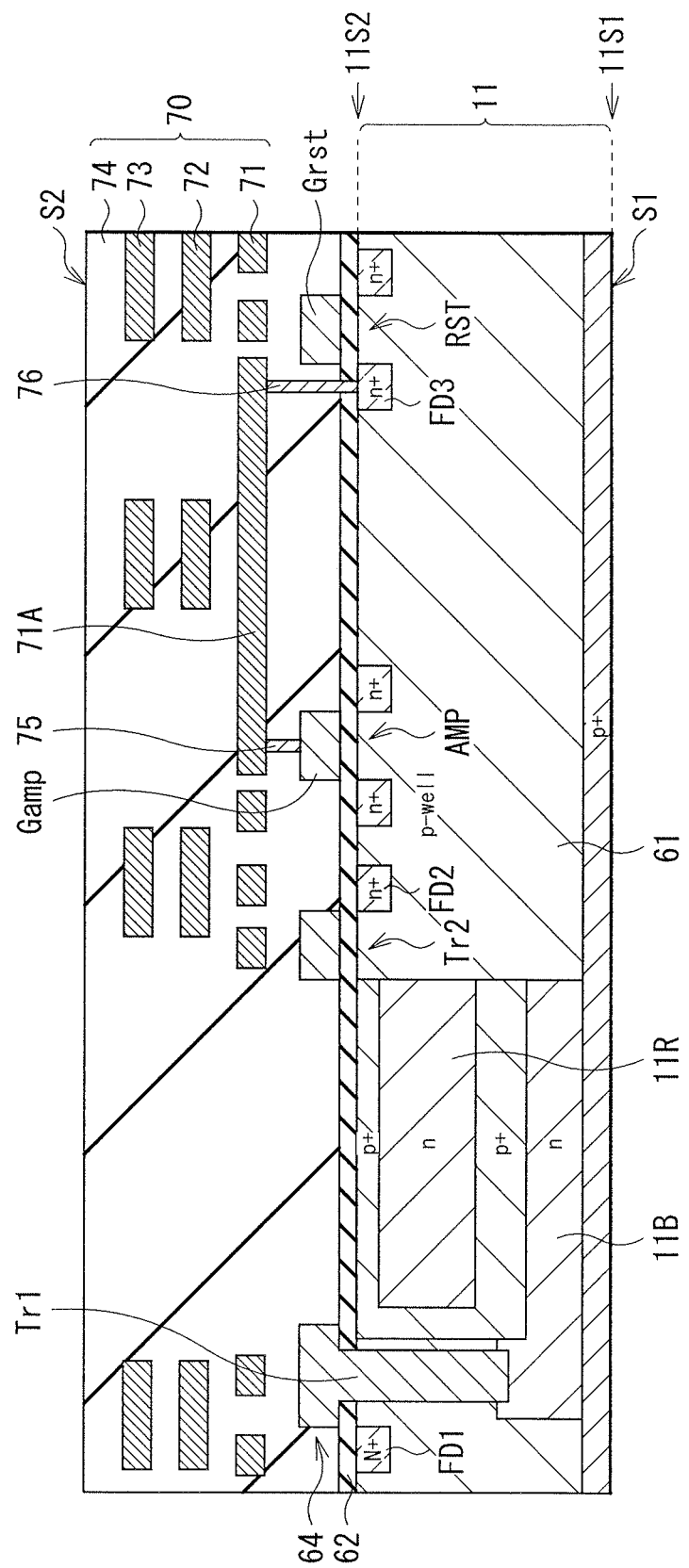
[FIG. 4]

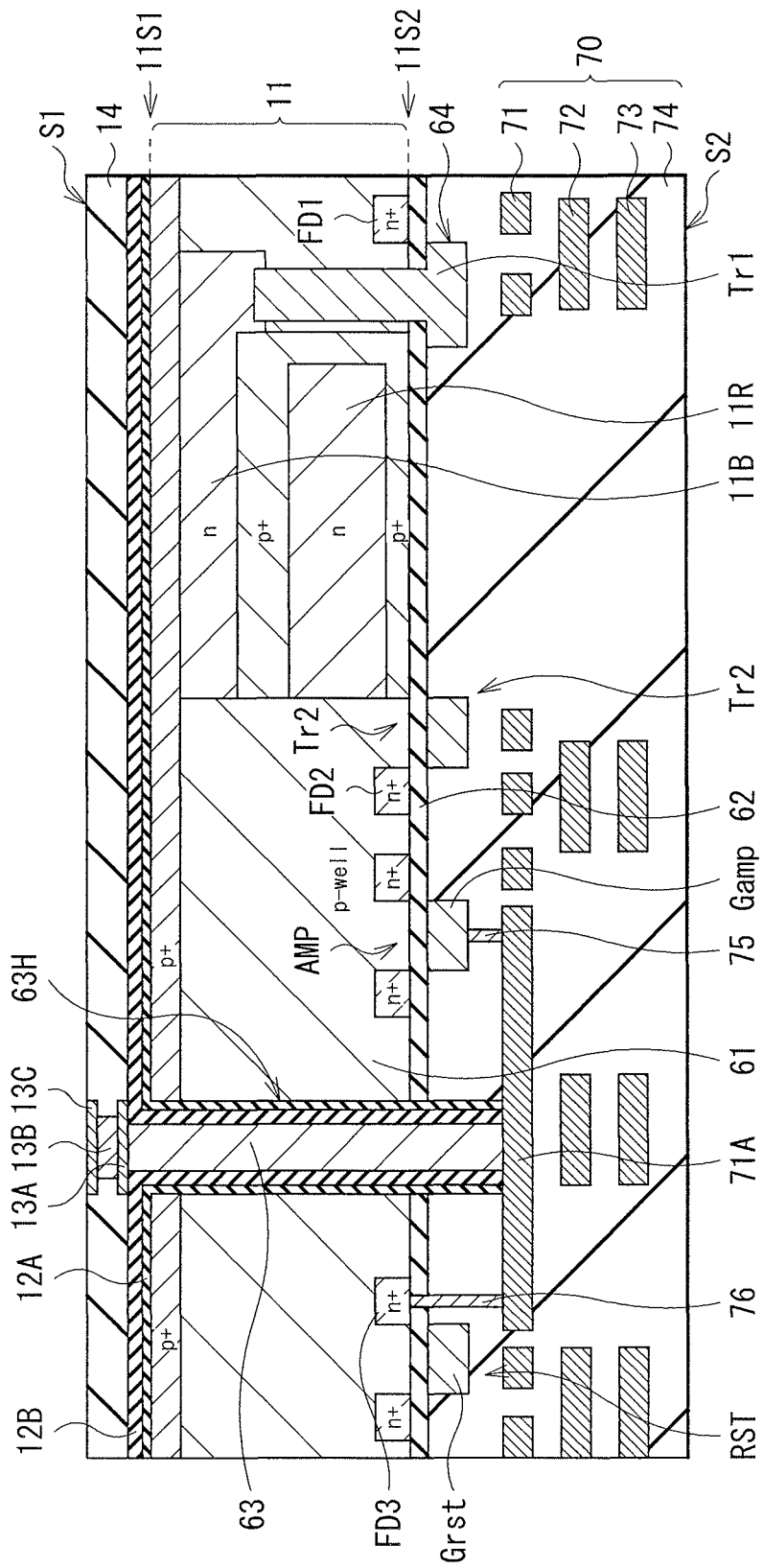
[FIG. 5]

[ FIG. 6 ]
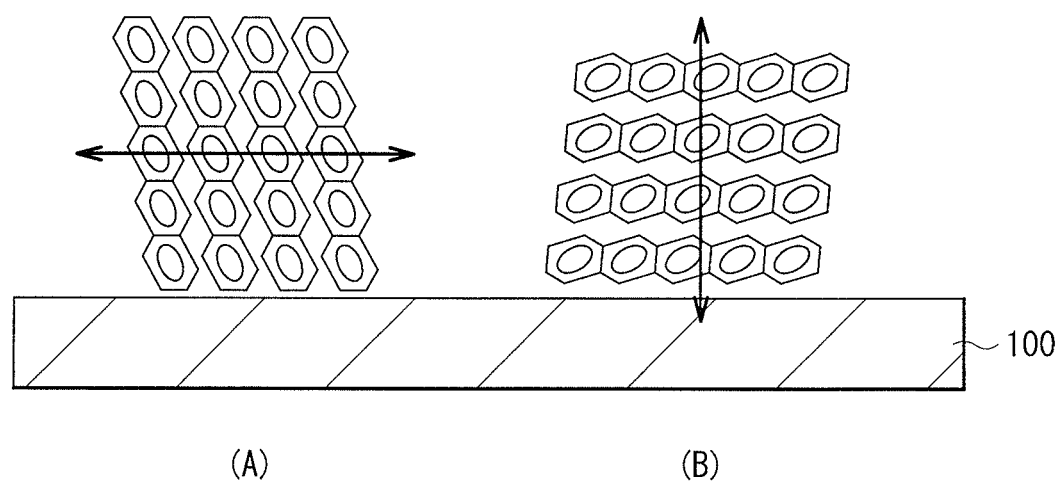
(A)　　　　　　　　　　(B)
[ FIG. 7 ]
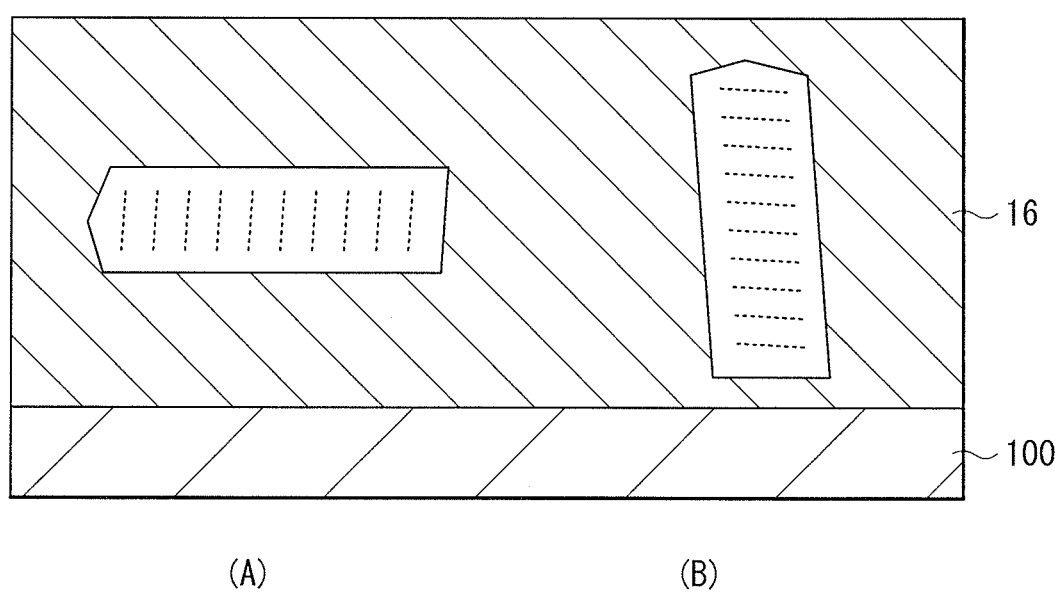
(A)　　　　　　　　　　(B)

[ FIG. 8 ]
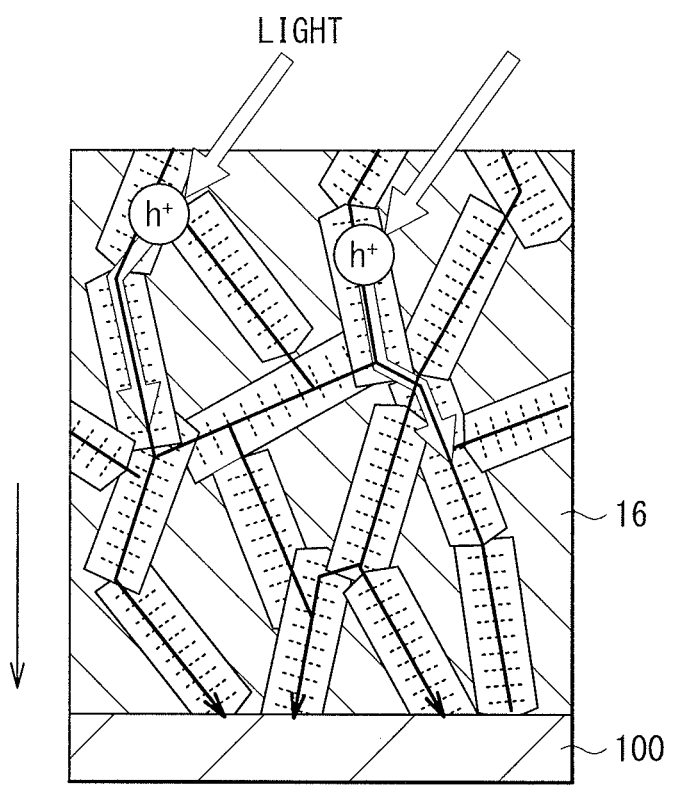

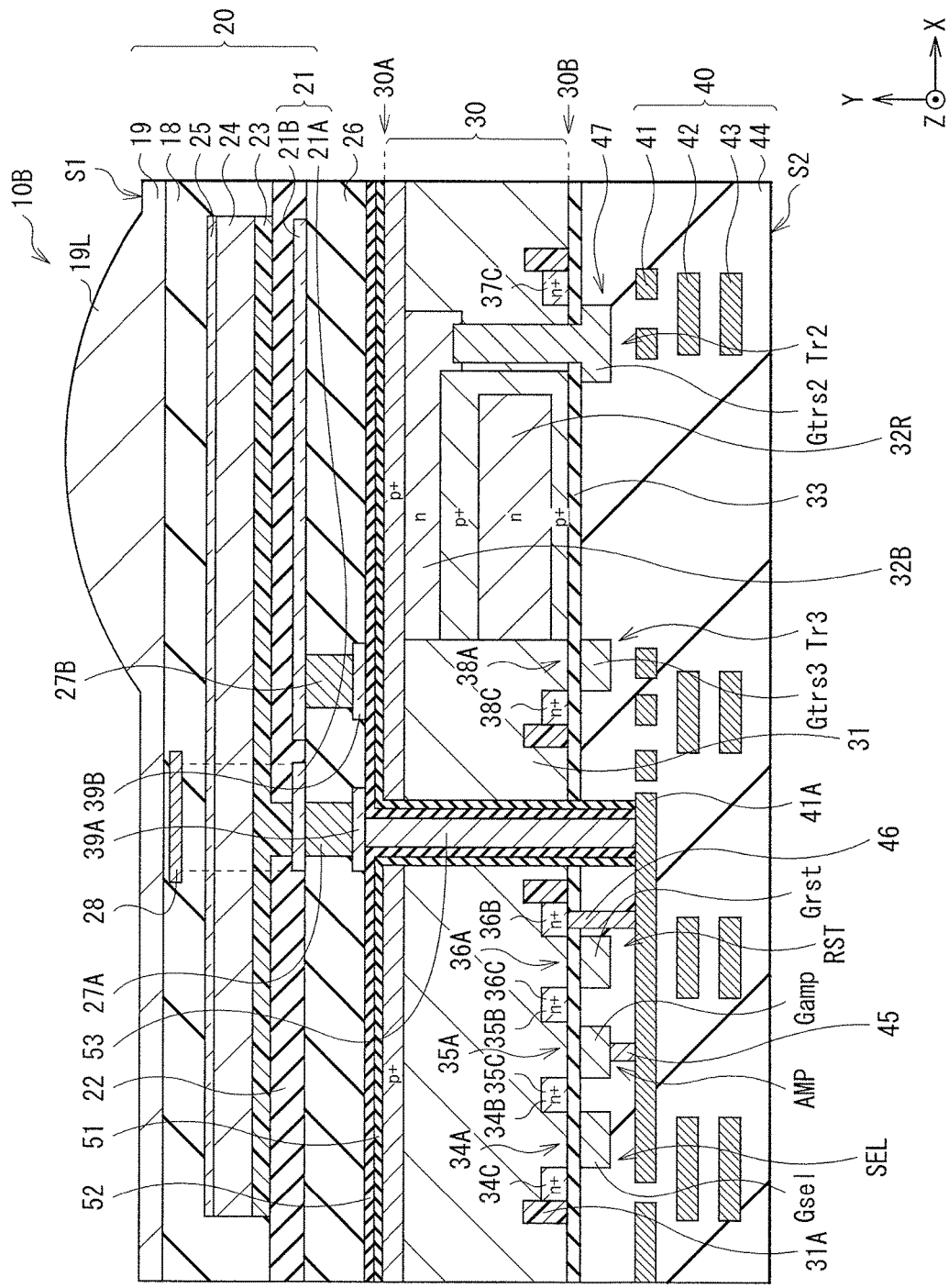

[ FIG. 10 ]
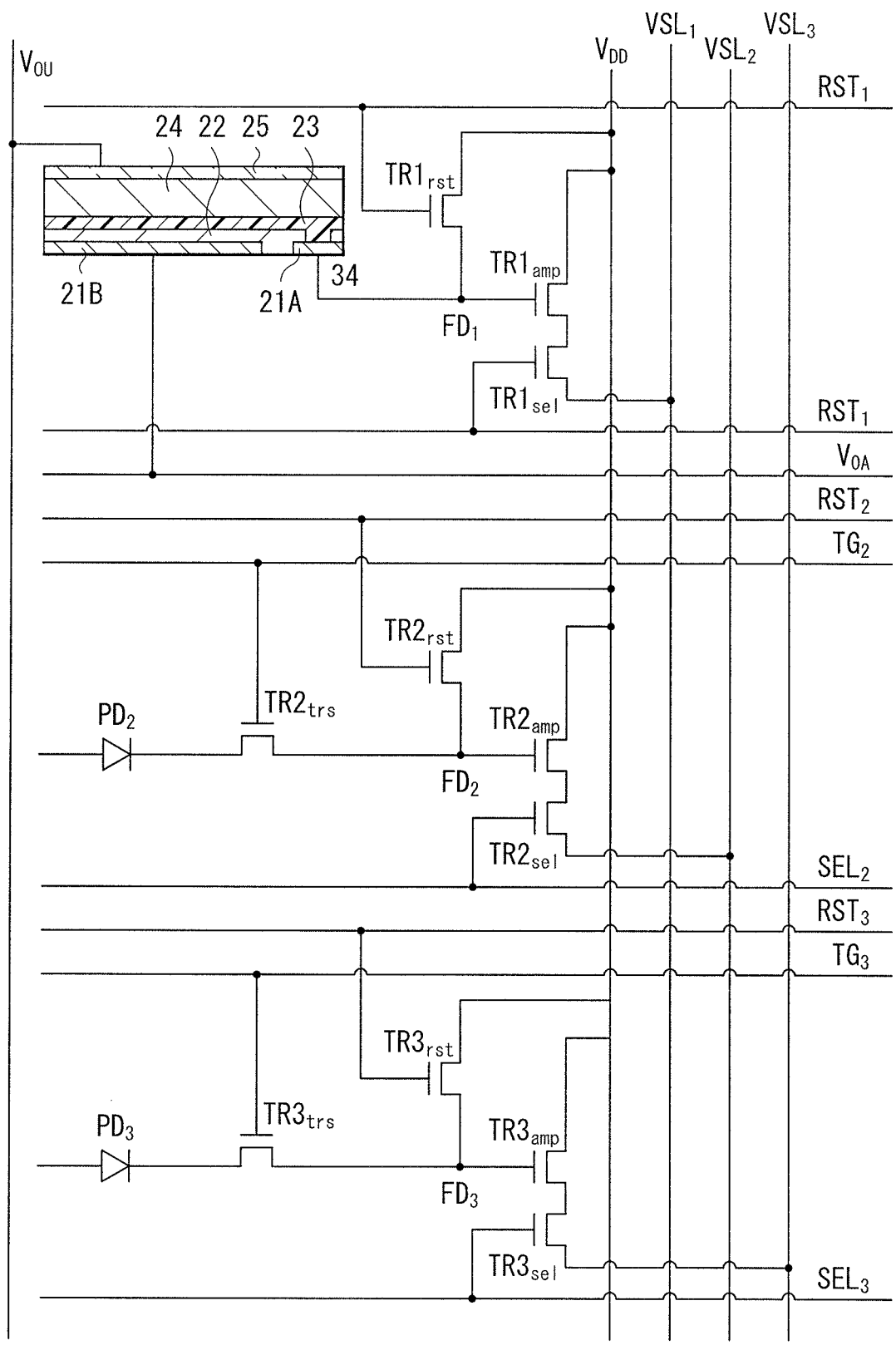

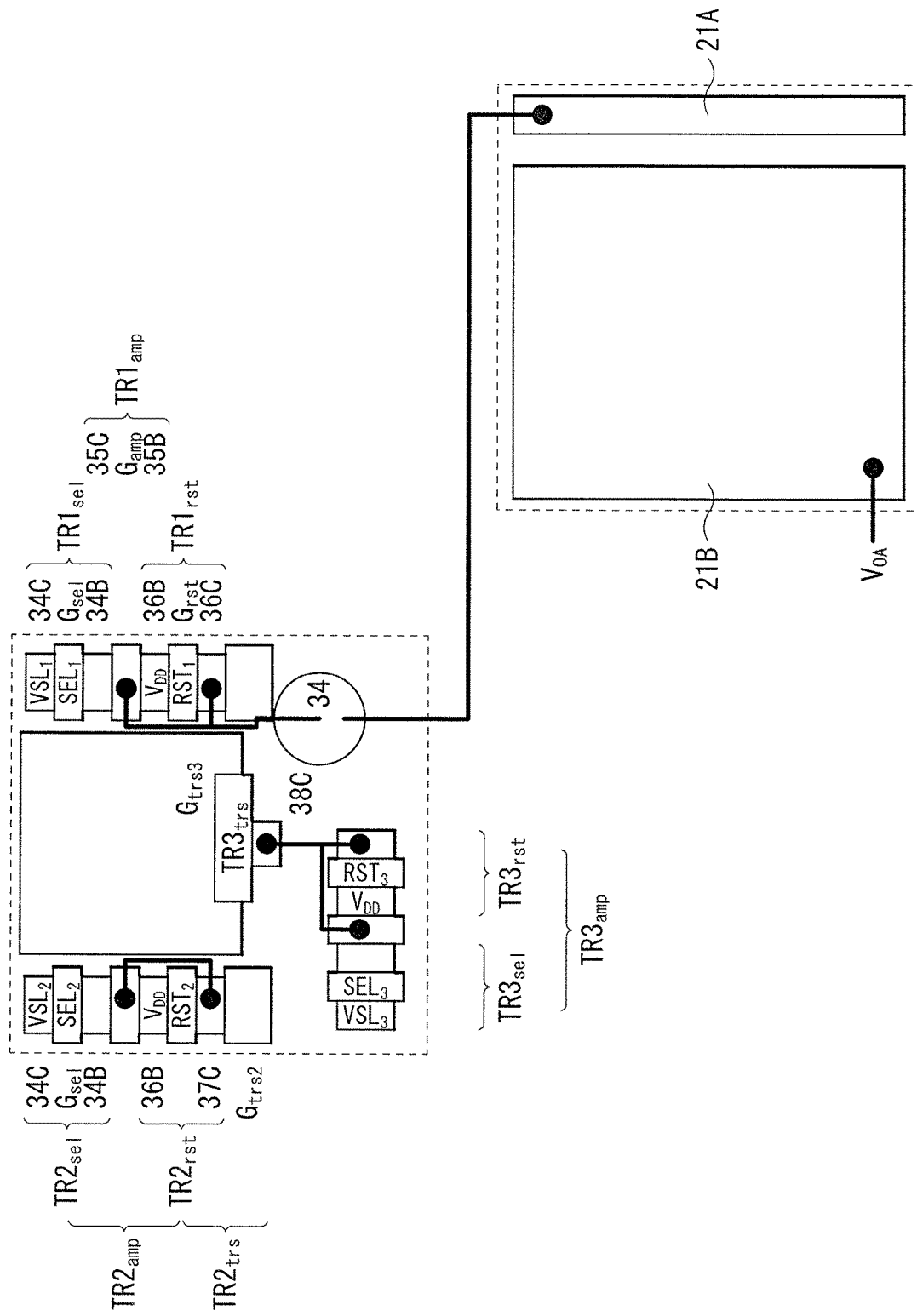

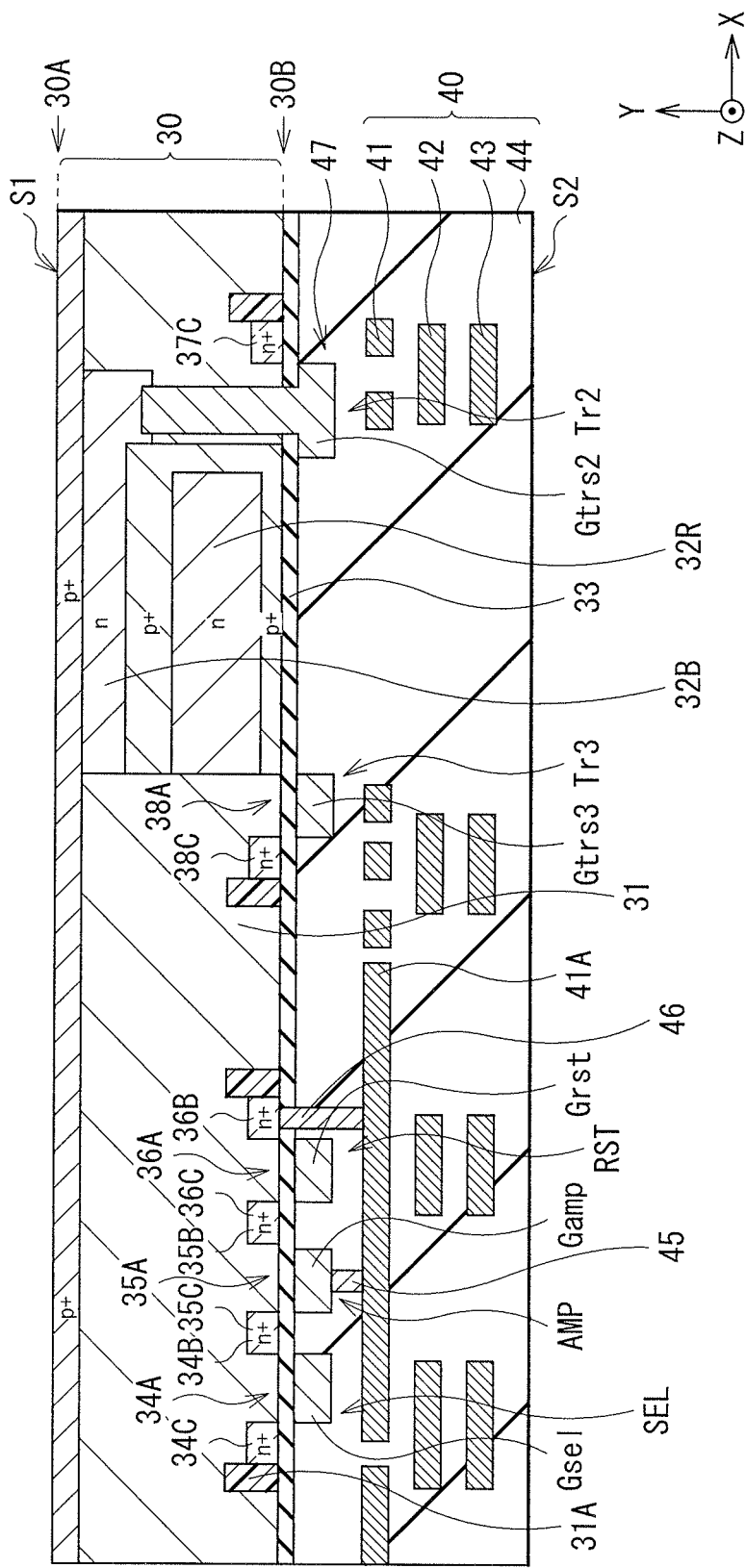
[ FIG. 12 ]

[FIG. 13]
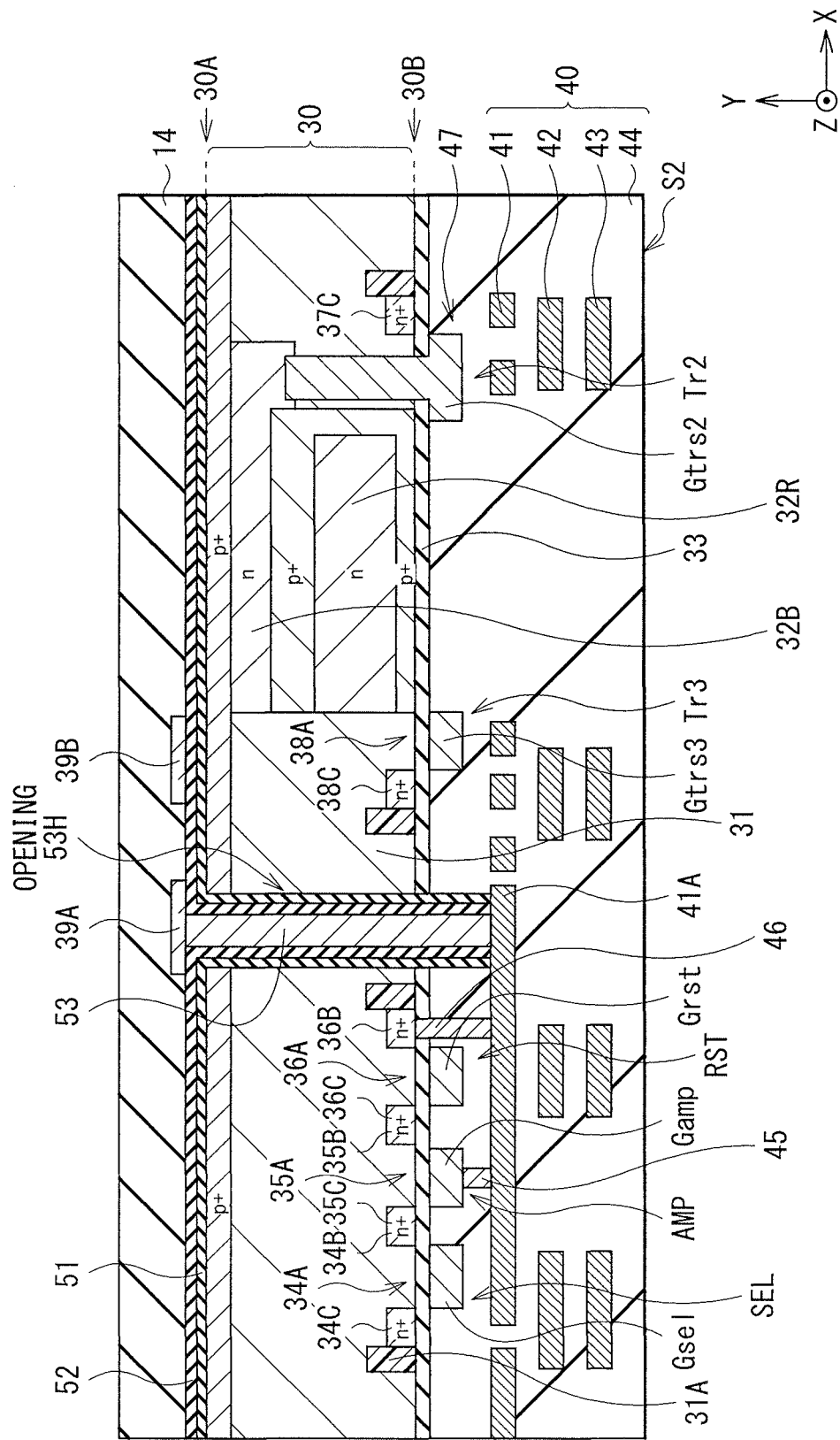

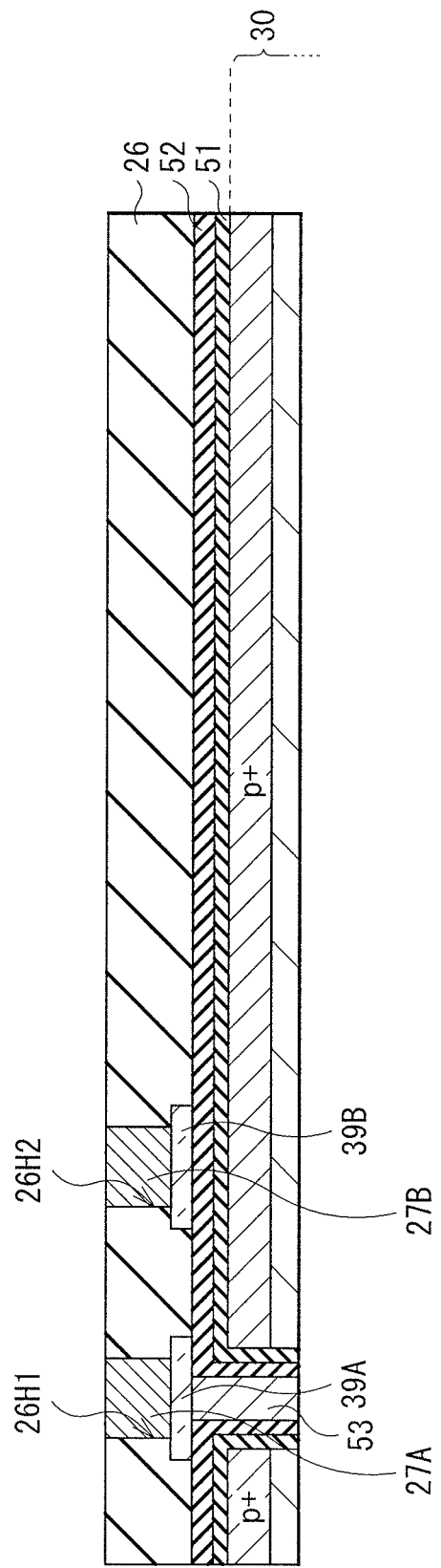

[FIG. 15]
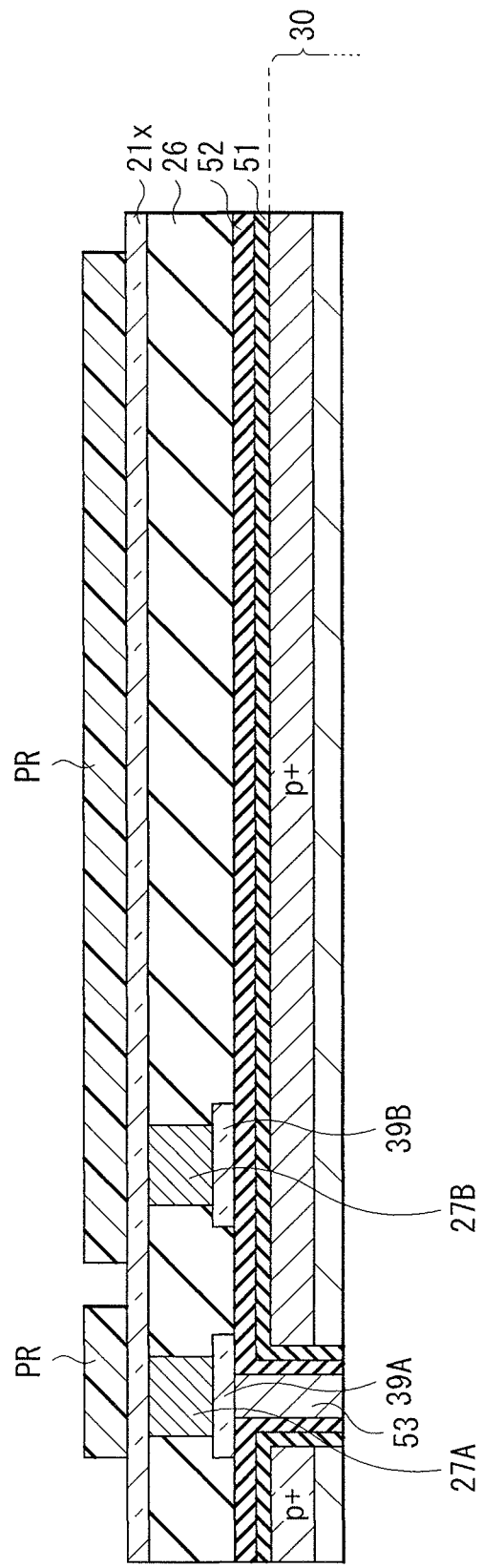

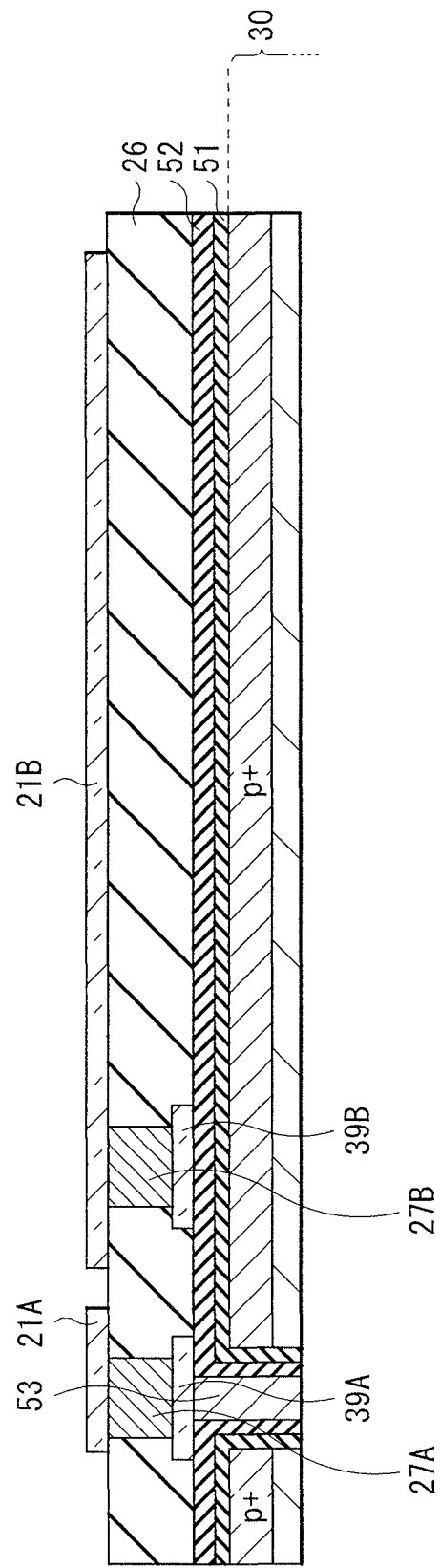

[FIG. 17]
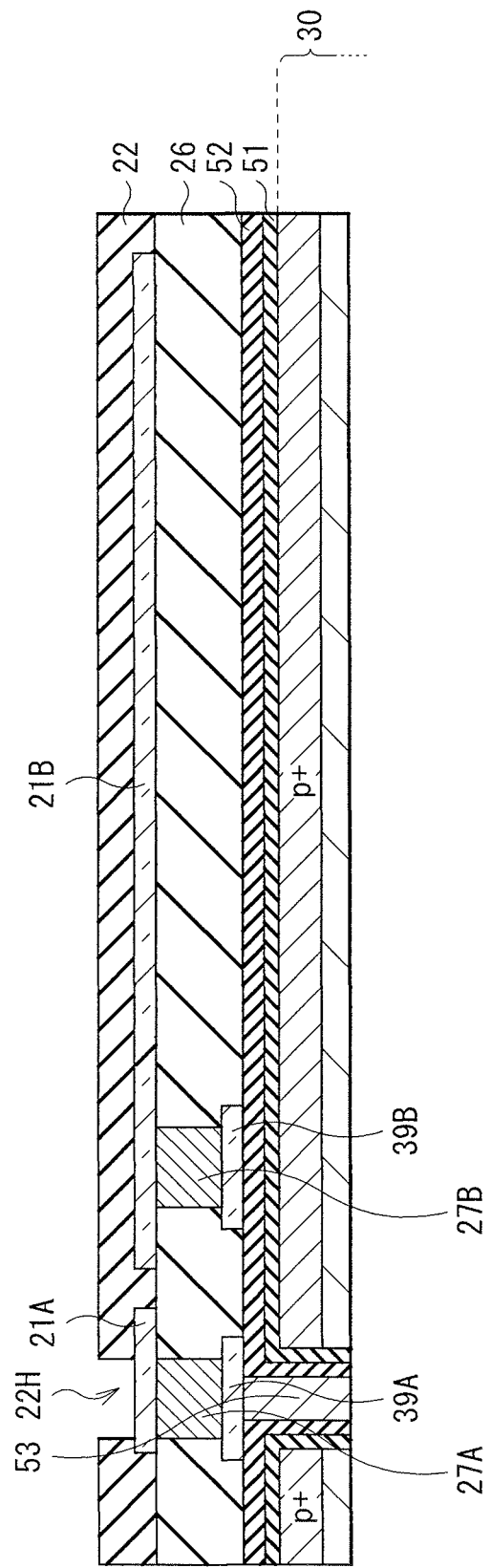

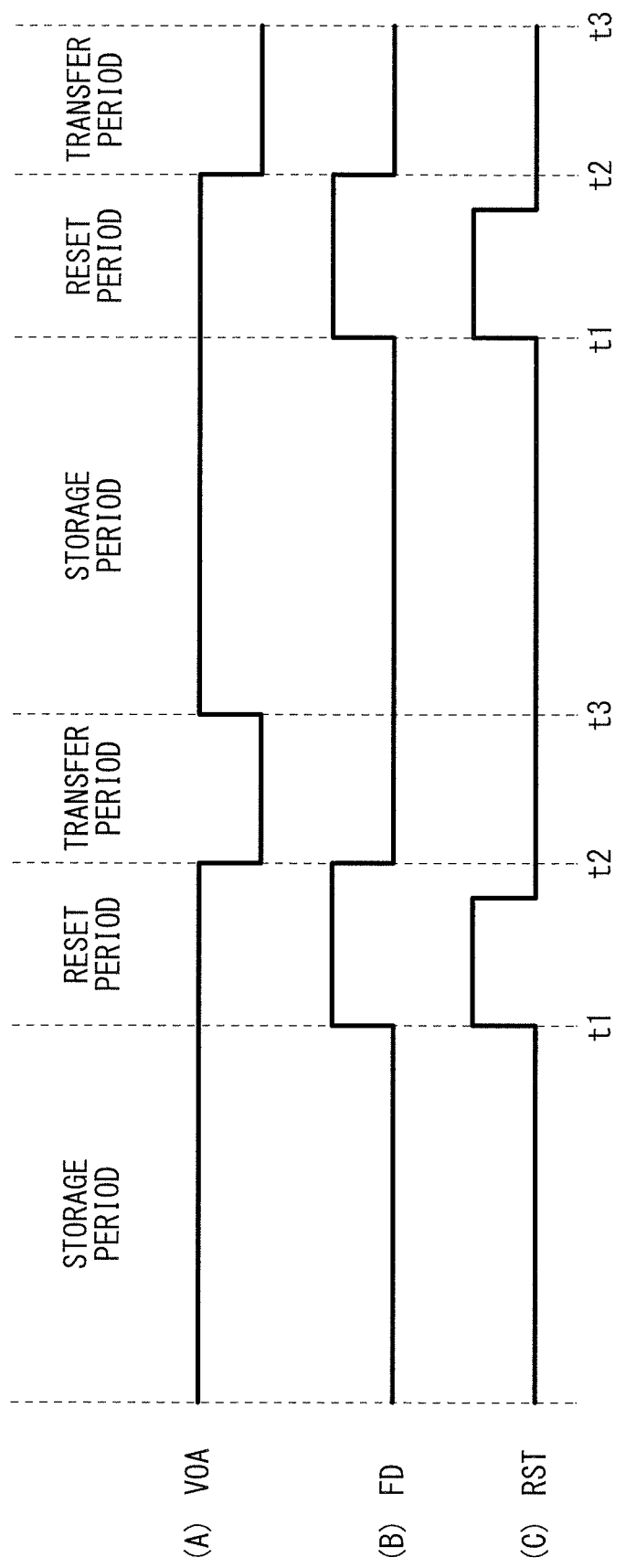
[FIG. 18]

[ FIG. 19 ]
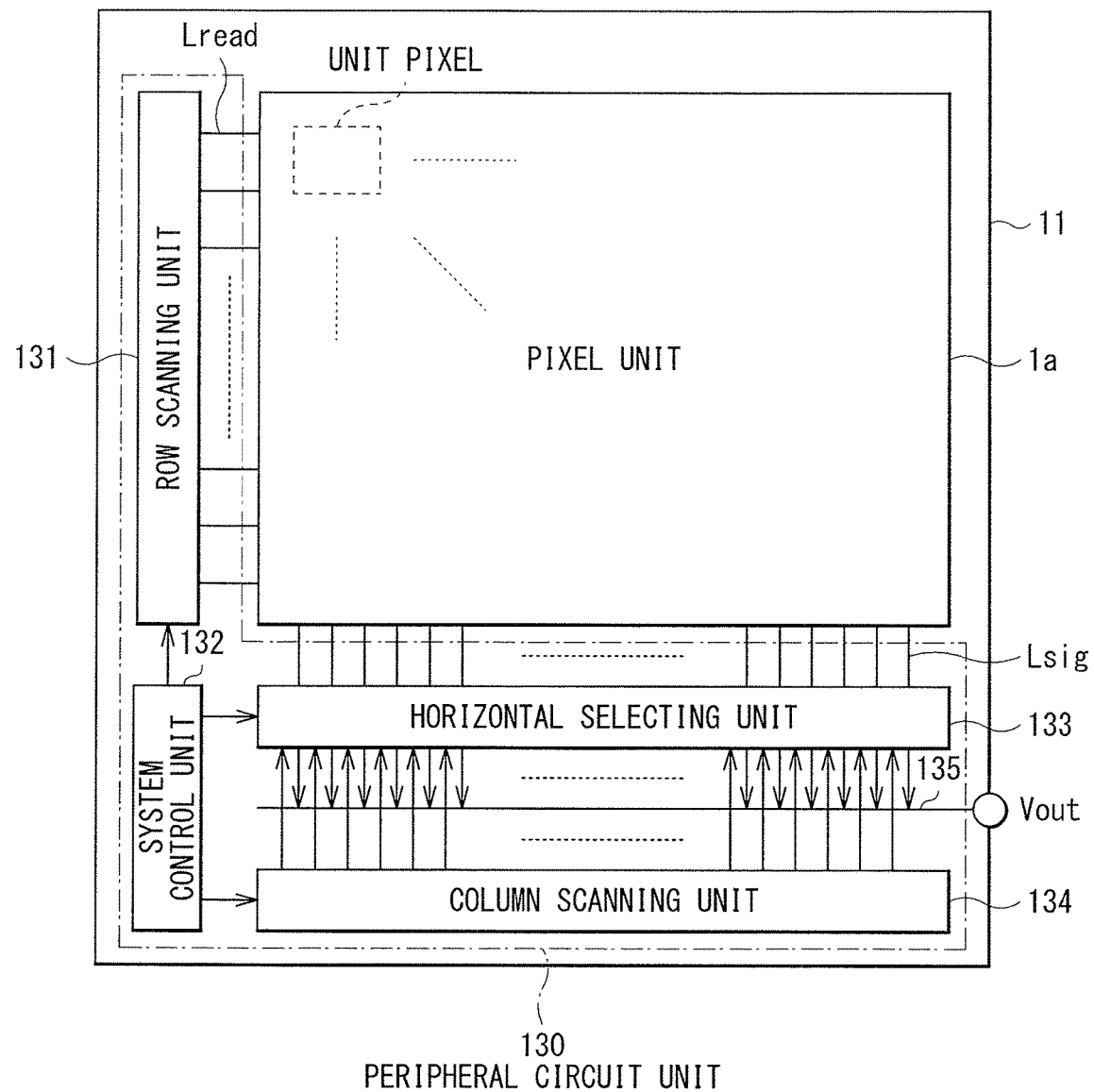

[FIG. 20]
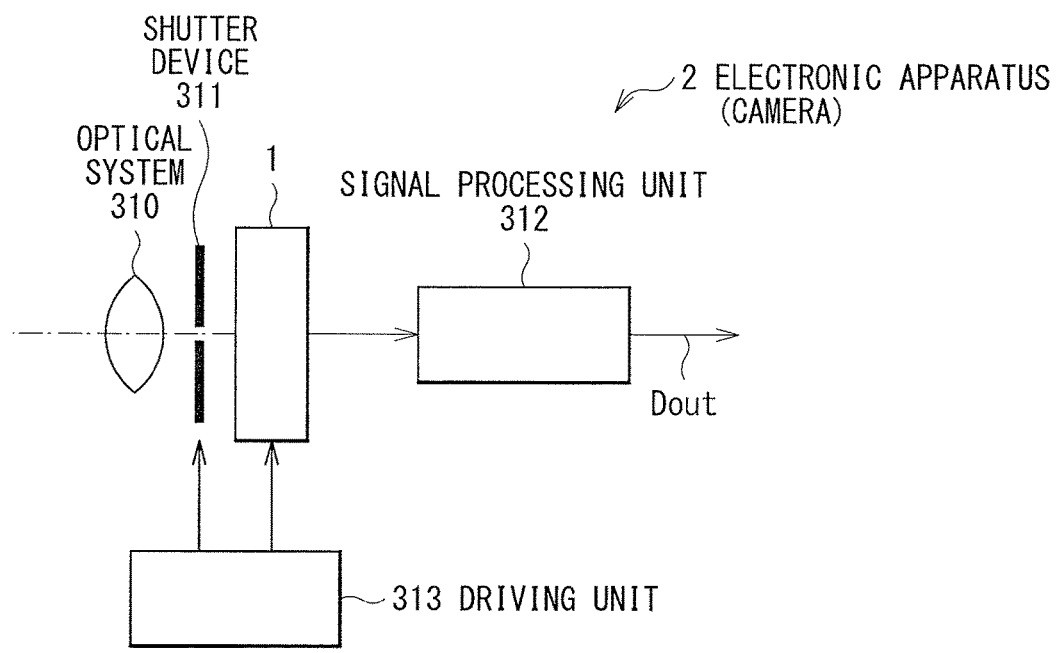

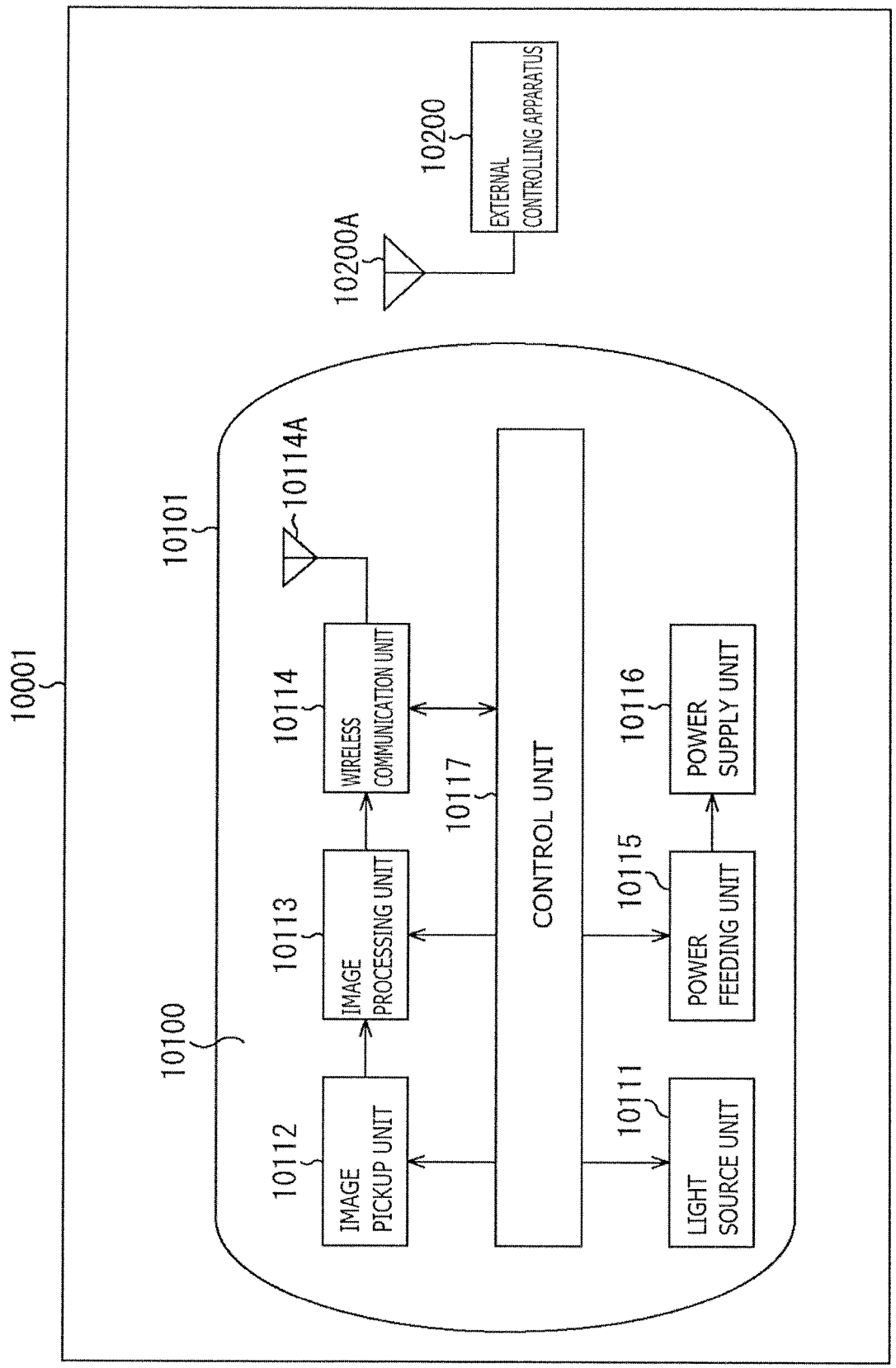

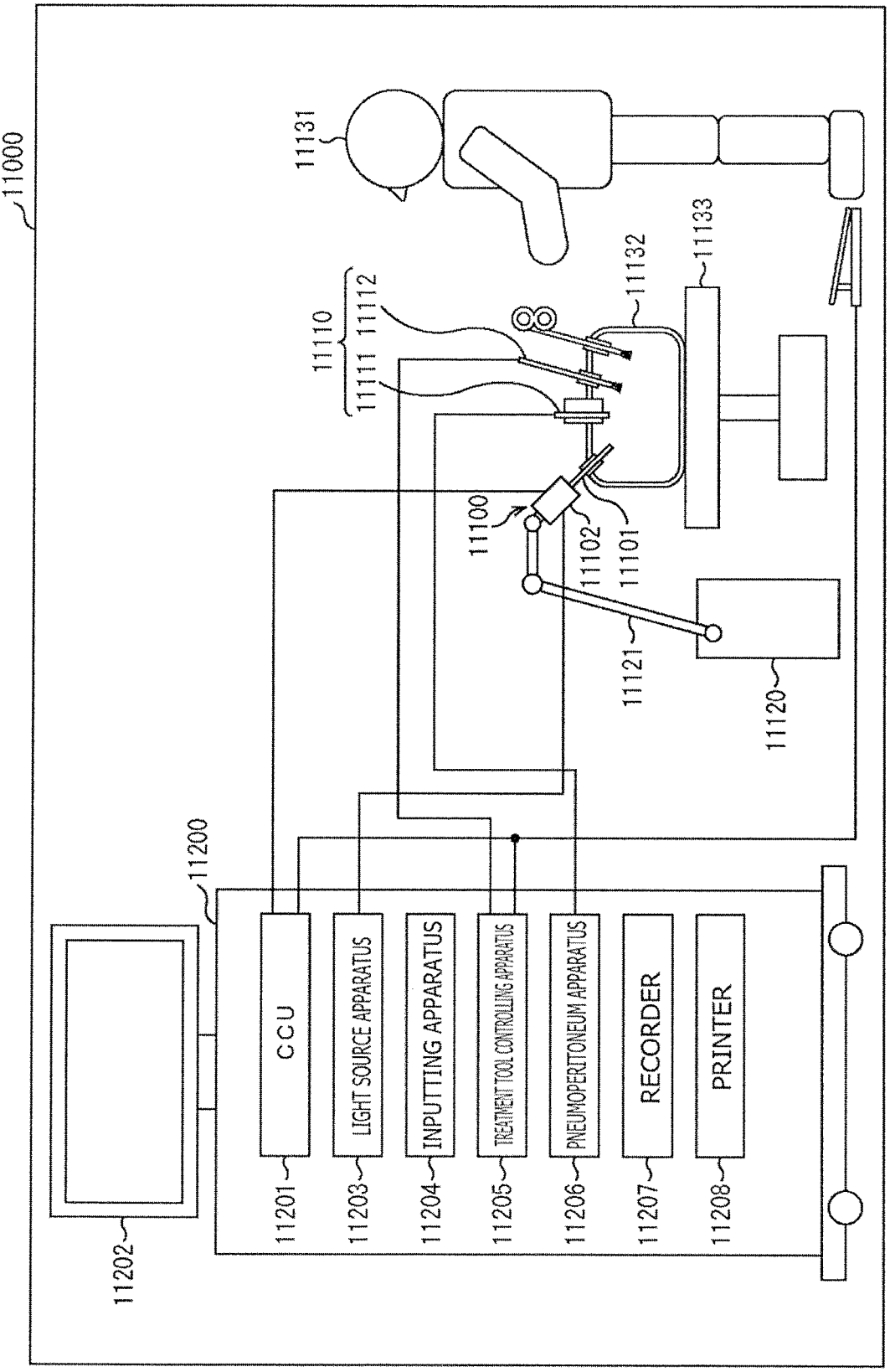
[FIG. 22]

[ FIG. 23 ]
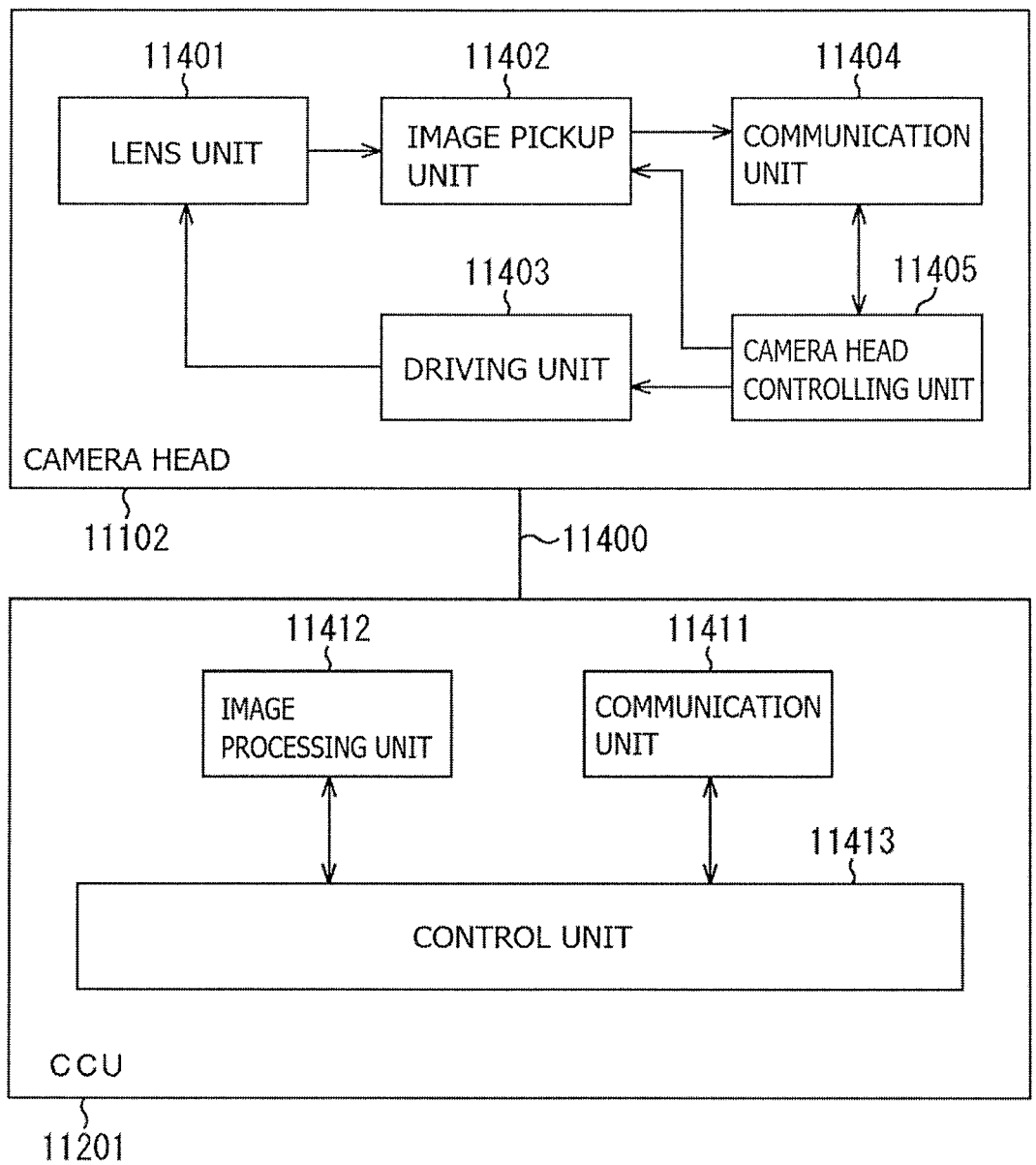

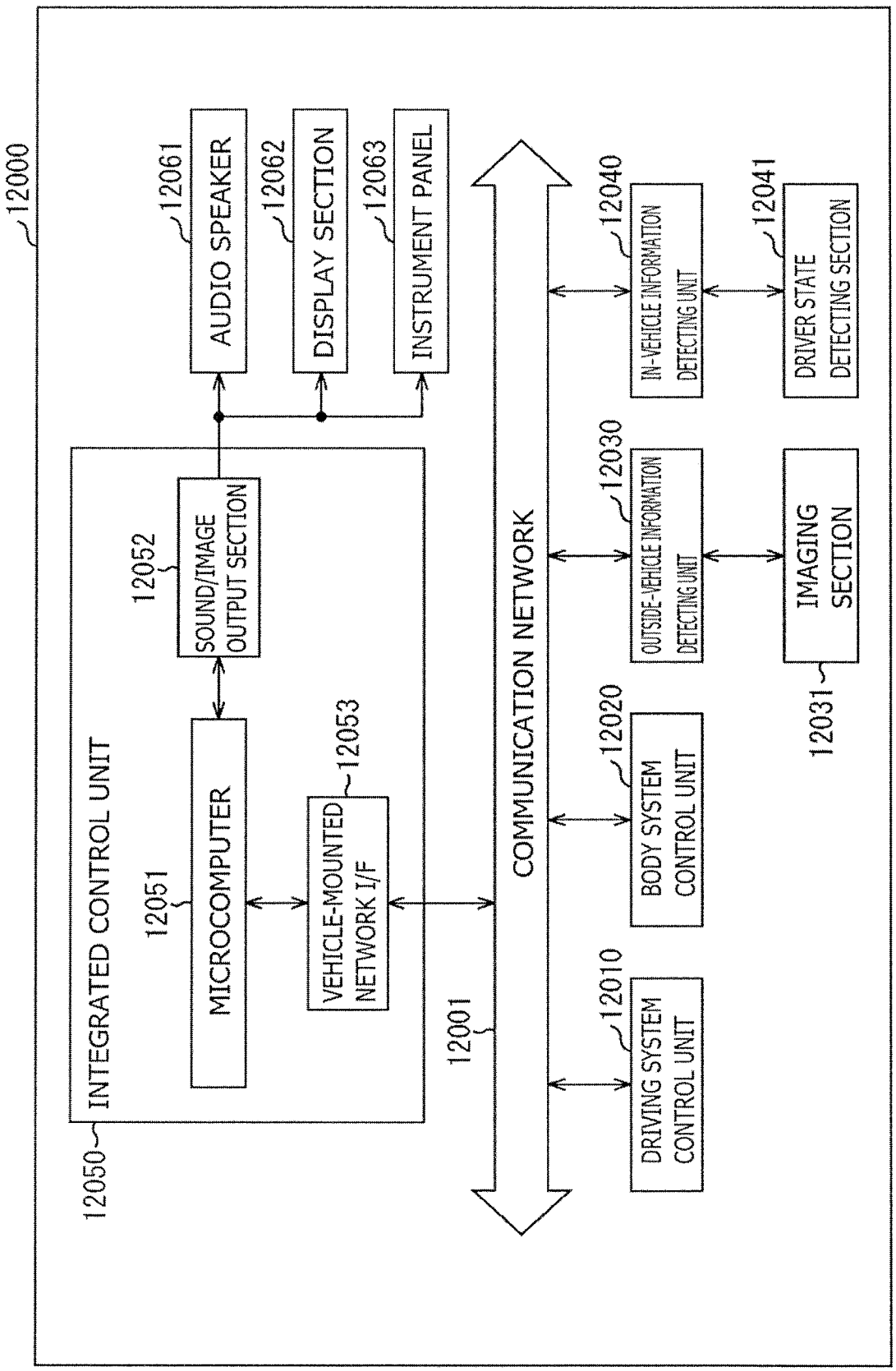

[ FIG. 25 ]
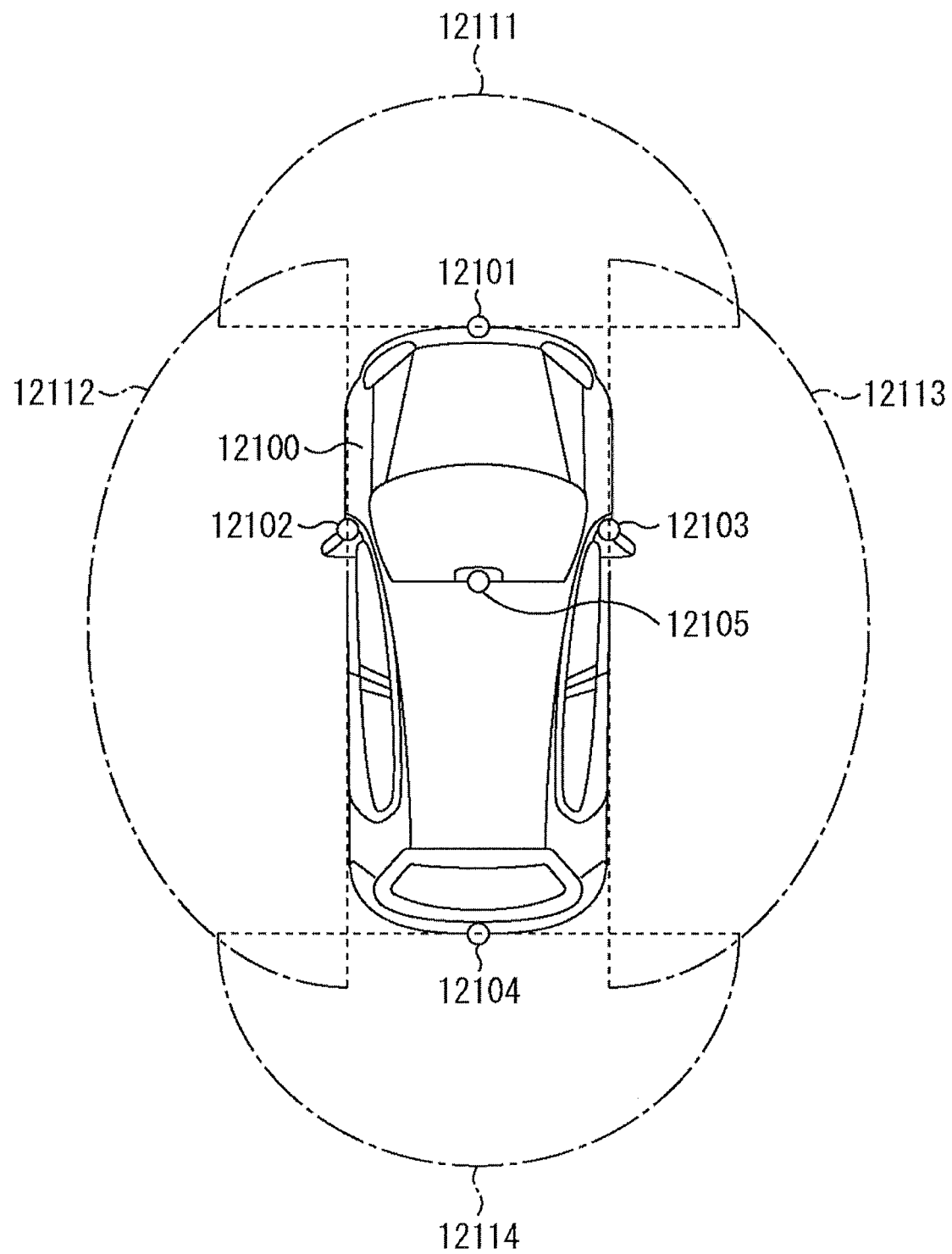

[ FIG. 26 ]
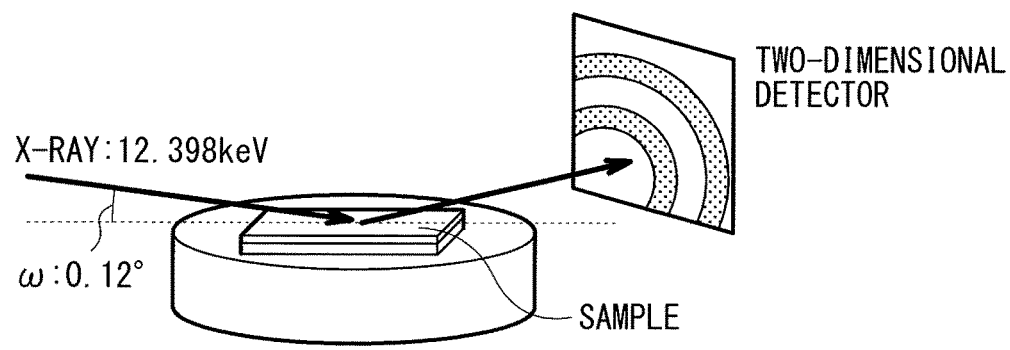
[ FIG. 27 ]
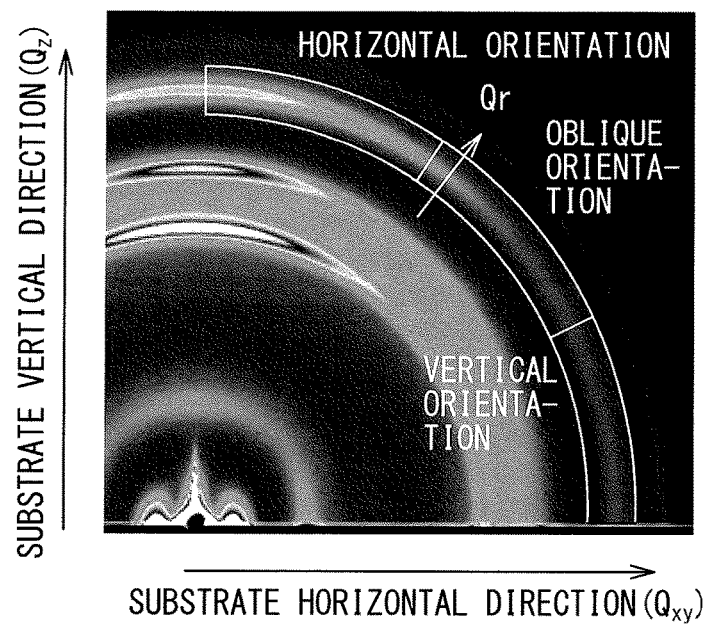

[ FIG. 28 ]
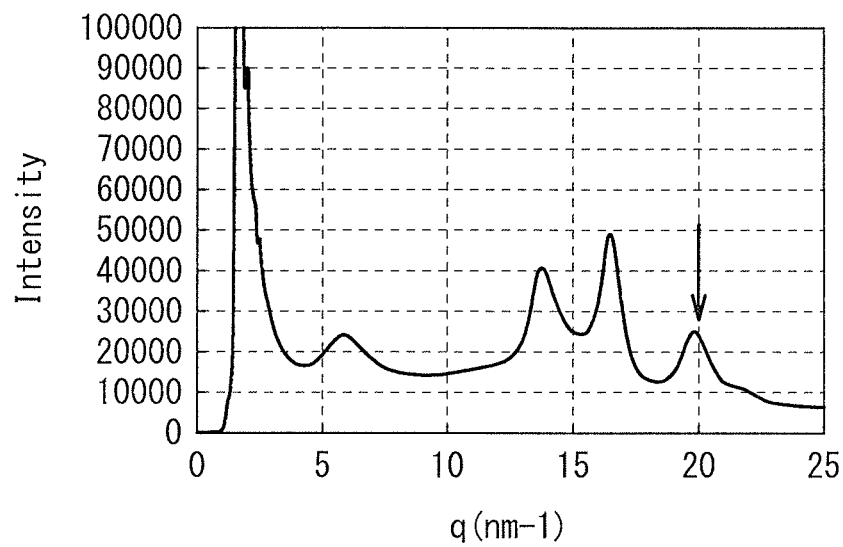
[ FIG. 29 ]
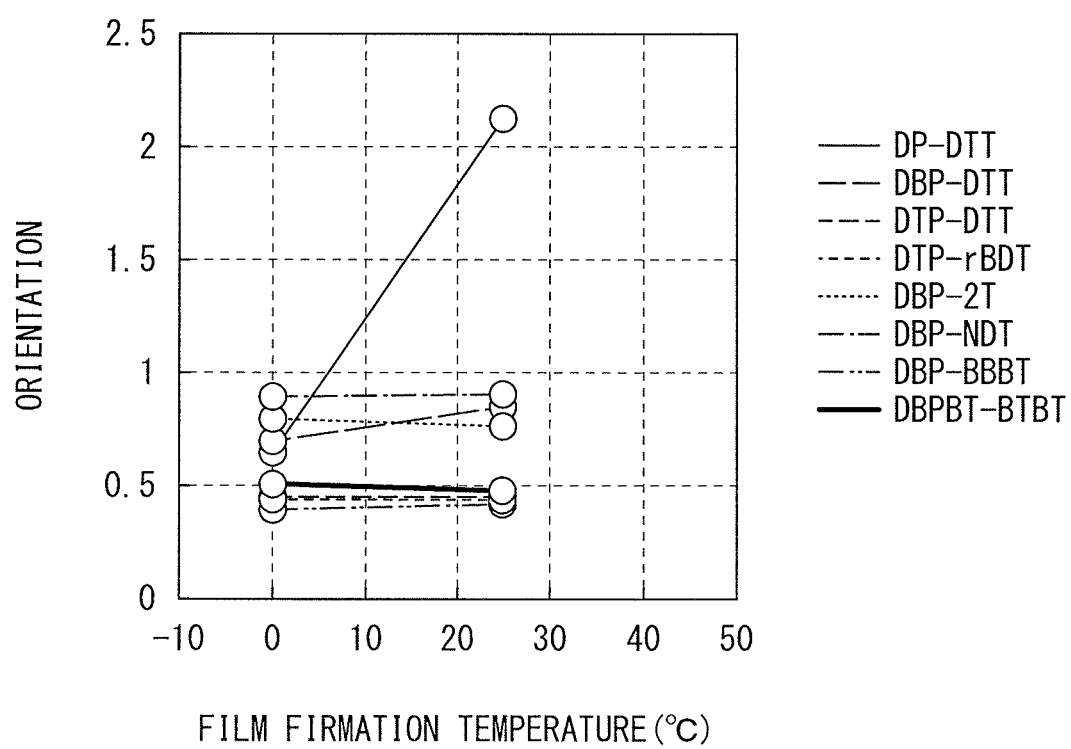

[ FIG. 30 ]
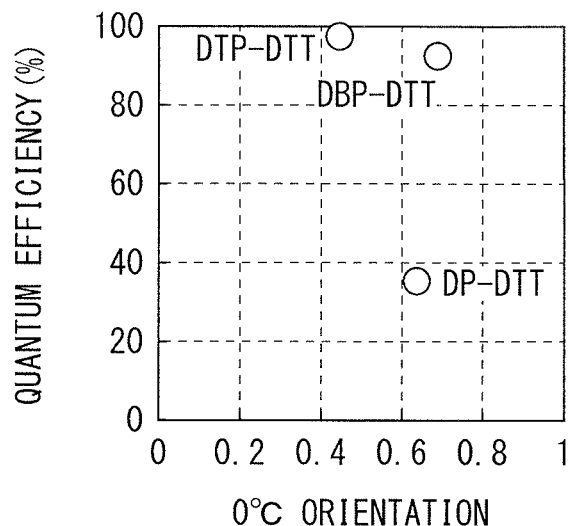
[ FIG. 31 ]
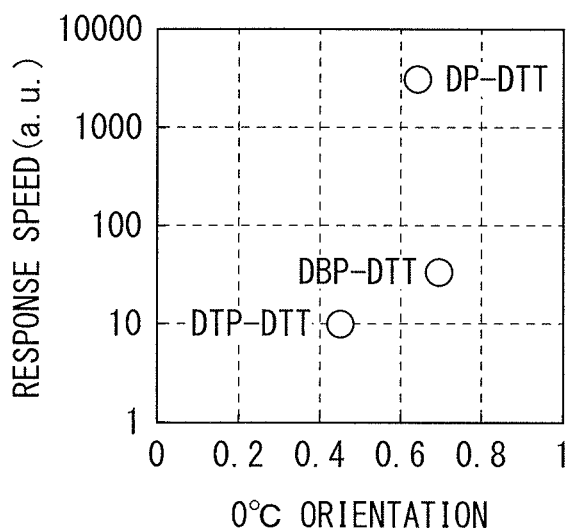

[ FIG. 32 ]
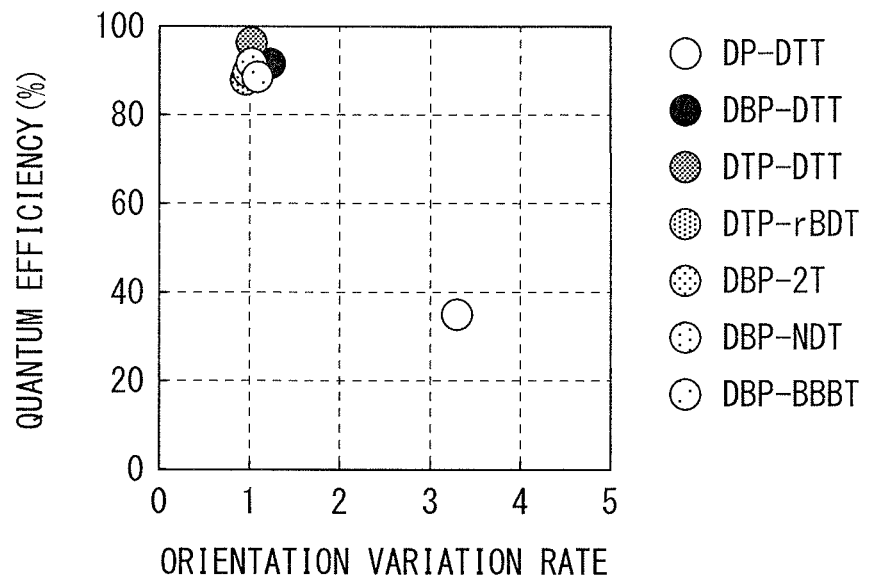
[ FIG. 33 ]
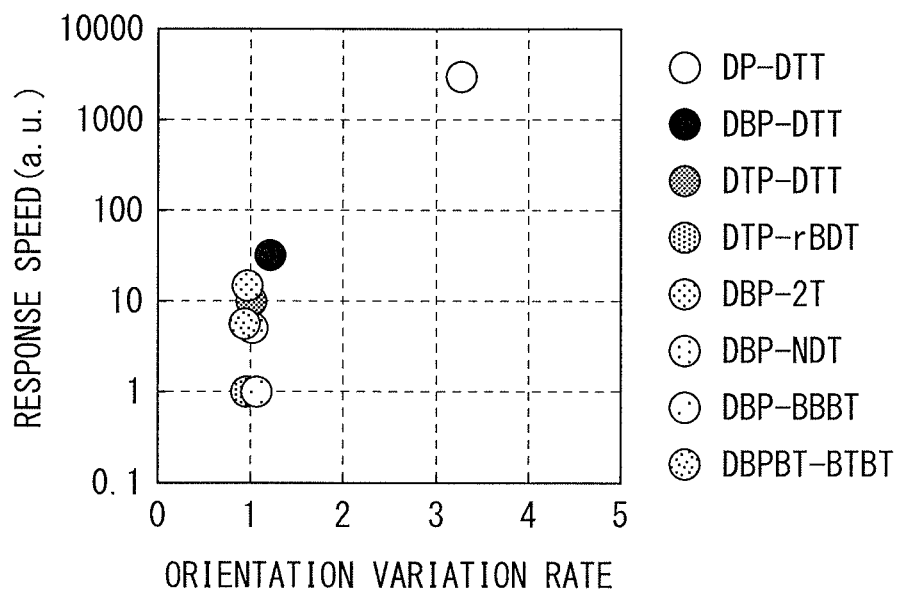

[ FIG. 34 ]
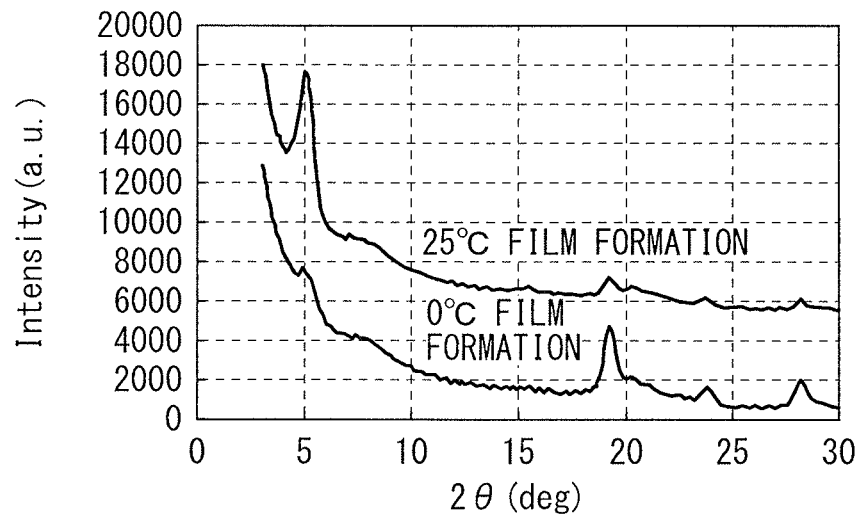
[ FIG. 35 ]
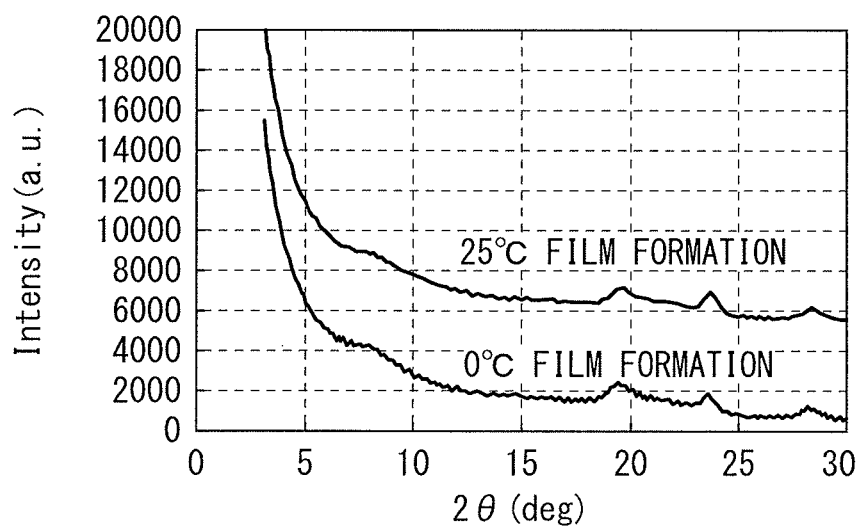

[ FIG. 36 ]
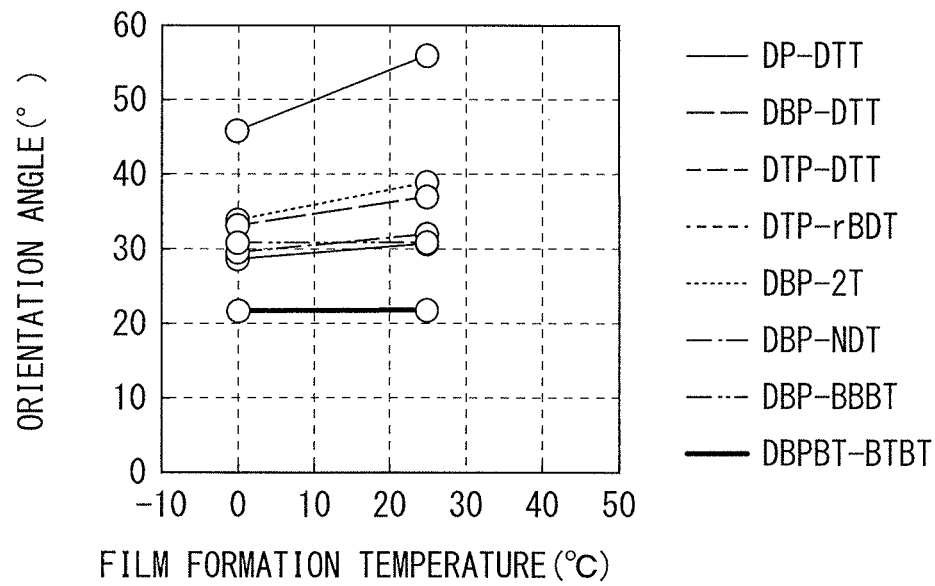
[ FIG. 37 ]
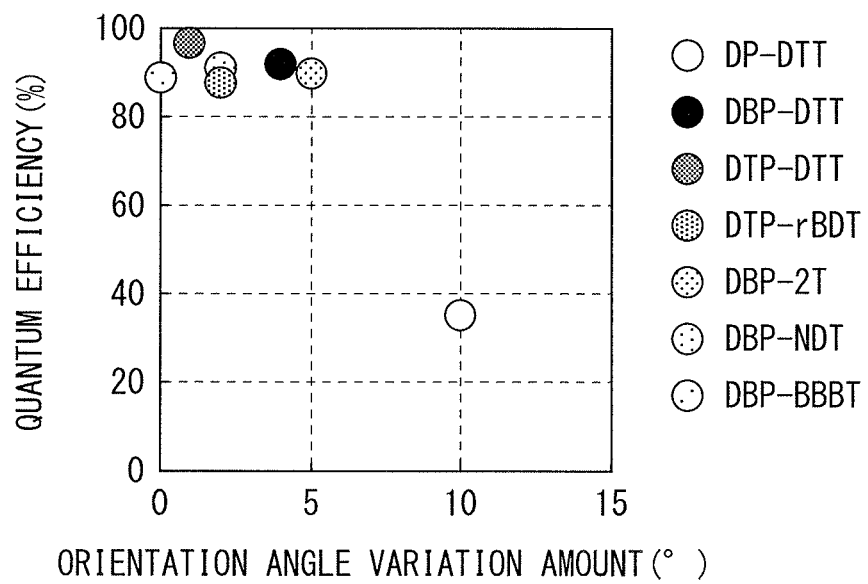

[ FIG. 38 ]
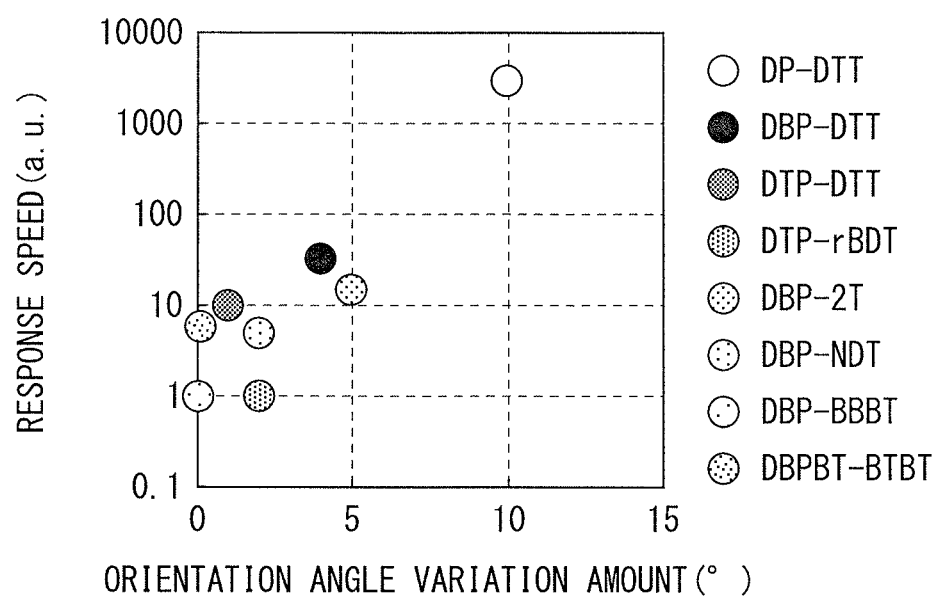

PHOTOELECTRIC CONVERSION DEVICE AND IMAGING APPARATUS

TECHNICAL FIELD

The present disclosure relates to, for example, a photoelectric conversion device using an organic semiconductor material and an imaging apparatus including this.

BACKGROUND ART

In recent years, devices using organic thin films have been developed. One of such devices is an organic photoelectric conversion device. There has been proposed an organic thin-film solar cell, an organic imaging device, or the like using it. In the organic photoelectric conversion device, a bulk heterostructure in which a p-type organic semiconductor and an n-type organic semiconductor are mixed is employed to improve quantum efficiency (for example, see PTL 1). However, the organic photoelectric conversion device has a problem that sufficient quantum efficiency cannot be obtained due to a low conductive characteristic of an organic semiconductor. In addition, the organic imaging device has a problem that an electric output signal is easily delayed with respect to entering light.

In general, it has been found that molecular orientation is important for conduction of an organic semiconductor. This is similarly applicable to an organic photoelectric conversion device having a bulk heterostructure. For this reason, in an organic photoelectric conversion device in which a conduction direction is perpendicular to a substrate, it is preferable that the organic semiconductor be horizontally oriented with respect to the substrate. In contrast, for example, PTL 2 discloses a photoelectric conversion device using an organic semiconductor compound having horizontal orientation. For example, PTL 3 discloses an organic thin-film solar cell in which an orientation control layer is provided in a lower layer of an i-layer. For example, PTL 4 discloses a method of manufacturing an organic photoelectric conversion device that controls orientation of a photoelectric conversion layer by controlling a substrate temperature to form a film.

CITATION LIST

Patent Literature

PTL 1: Japanese Unexamined Patent Application Publication No. 2005-303266
PTL 2: Japanese Unexamined Patent Application Publication No. 2009-60053
PTL 3: Japanese Unexamined Patent Application Publication No. 2007-59457
PTL 4: Japanese Unexamined Patent Application Publication No. 2008-258421

SUMMARY OF THE INVENTION

Problem to be Solved by the Invention

As described above, it is desired to improve quantum efficiency and a response speed of a photoelectric conversion device using an organic semiconductor material.

It is desirable to provide a photoelectric conversion device and an imaging apparatus capable of improving quantum efficiency and a response speed.

Means for Solving the Problem

A first photoelectric conversion device of one embodiment of the present disclosure includes a first electrode, a second electrode opposed to the first electrode, and a photoelectric conversion layer. The photoelectric conversion layer is provided between the first electrode and the second electrode and includes at least one type of one organic semiconductor material having crystallinity. Variation in a ratio between horizontally-oriented crystal and vertically-oriented crystal in the photoelectric conversion layer is three times or less between a case where film formation of the one organic semiconductor material is performed at a first temperature and a case where the film formation of the one organic semiconductor material is performed at a second temperature. The second temperature is higher than the first temperature.

In a first imaging apparatus of one embodiment of the present disclosure, each pixel includes one or a plurality of photoelectric conversion devices. The first imaging apparatus includes the above-described first photoelectric conversion device according to one embodiment of the present disclosure as any of the photoelectric conversion devices.

A second photoelectric conversion device of one embodiment of the present disclosure includes a first electrode, a second electrode opposed to the first electrode, and a photoelectric conversion layer. The photoelectric conversion layer is provided between the first electrode and the second electrode and includes at least one type of one organic semiconductor material having crystallinity. A variation amount of an angle formed with an electrode surface of the first electrode is smaller than 10 degrees between a case where film formation of the one organic semiconductor material is performed at a first temperature and a case where the film formation of the one organic semiconductor material is performed at a second temperature. The second temperature is higher than the first temperature.

In a second imaging apparatus of one embodiment of the present disclosure, each pixel includes one or a plurality of photoelectric conversion devices. The second imaging apparatus includes the above-described second photoelectric conversion device according to one embodiment of the present disclosure as any of the photoelectric conversion devices.

Effects of the Invention

In the first photoelectric conversion device of one embodiment of the present disclosure, the first imaging apparatus of one embodiment of the present disclosure, the second photoelectric conversion device of one embodiment of the present disclosure, and the second imaging apparatus of one embodiment of the present disclosure, a photoelectric conversion layer including at least one type of one organic semiconductor material having crystallinity is provided. The one organic semiconductor material allows variation in a ratio between horizontally-oriented crystal and vertically-oriented crystal in the photoelectric conversion layer to be three times or less between a case where film formation is performed at a first temperature and a case where the film formation is performed at a second temperature higher than the first temperature (first photoelectric conversion device). Alternatively, it allows a variation amount of an angle formed with an electrode surface of the first electrode to be smaller than 10° between a case where film formation is performed at a first temperature and a case where the film formation is performed at a second temperature higher than the first temperature (second photoelectric conversion device). As a result, a mixture state of the organic semiconductor material in the bulk hetero film can be appropriately controlled, and formation of a defect at a grain boundary can be reduced.

According to the first photoelectric conversion device of one embodiment of the present disclosure, the first imaging apparatus of one embodiment of the present disclosure, the second photoelectric conversion device of one embodiment of the present disclosure, and the second imaging apparatus of one embodiment of the present disclosure, the photoelectric conversion layer is provided that includes the one organic semiconductor material that allows variation in a ratio between horizontally-oriented crystal and vertically-oriented crystal in the photoelectric conversion layer to be three times or less between a case where film formation is performed at a first temperature and a case where the film formation is performed at a second temperature higher than the first temperature or allows a variation amount of an angle formed with an electrode surface of the first electrode to be smaller than 10° between the foregoing cases. It is therefore possible to appropriately control the mixture state of the organic semiconductor material in the bulk hetero film. Accordingly, formation of a defect at a grain boundary can be reduced, and quantum efficiency and responsiveness can be improved.

It is to be noted that the effects described here are not necessarily limiting, and any of the effects described in the present disclosure may be provided.

BRIEF DESCRIPTION OF THE DRAWINGS

FIG. 1 is a schematic cross-sectional view illustrating a configuration of a photoelectric conversion device according to a first embodiment of the present disclosure.

FIG. 2 is a diagram explaining a molecular length and a molecular width of an organic semiconductor material used in the photoelectric conversion device illustrated in FIG. 1.

FIG. 3 is a schematic plan view illustrating a configuration of a unit pixel of the photoelectric conversion device illustrated in FIG. 1.

FIG. 4 is a schematic cross-sectional view for explaining a method of manufacturing the photoelectric conversion device illustrated in FIG. 1.

FIG. 5 is a schematic cross-sectional view illustrating a process following FIG. 3.

FIG. 6 is a diagram illustrating orientation and conduction anisotropy of organic molecules.

FIG. 7 schematically illustrates crystal including a plurality of organic molecules oriented as illustrated in FIG. 5.

FIG. 8 is a conceptual diagram describing crystal of organic molecules and conduction of charges within a photoelectric conversion layer.

FIG. 9 is a cross-sectional view illustrating an example of a configuration of a photoelectric conversion device according to a second embodiment of the present disclosure.

FIG. 10 is an equivalent circuit diagram of a photoelectric conversion device illustrated in FIG. 9.

FIG. 11 is a schematic diagram illustrating arrangement of a lower electrode and transistors configuring a control unit of the photoelectric conversion device illustrated in FIG. 9.

FIG. 12 is a cross-sectional view for describing a method of manufacturing the photoelectric conversion device illustrated in FIG. 9.

FIG. 13 is a cross-sectional view illustrating a process following FIG. 12.

FIG. 14 is a cross-sectional view illustrating a process following FIG. 13.

FIG. 15 is a cross-sectional view illustrating a process following FIG. 14.

FIG. 16 is a cross-sectional view illustrating a process following FIG. 15.

FIG. 17 is a cross-sectional view illustrating a process following FIG. 16.

FIG. 18 is a timing chart illustrating an example of operation of the photoelectric conversion device illustrated in FIG. 9.

FIG. 19 is a block diagram illustrating an overall configuration of an imaging device including the photoelectric conversion device illustrated in FIG. 1.

FIG. 20 is a functional block diagram illustrating an example of an imaging apparatus (camera) using the imaging device illustrated in FIG. 19.

FIG. 21 is a block diagram depicting an example of a schematic configuration of an in-vivo information acquisition system.

FIG. 22 is a view depicting an example of a schematic configuration of an endoscopic surgery system.

FIG. 23 is a block diagram depicting an example of a functional configuration of a camera head and a camera control unit (CCU).

FIG. 24 is a block diagram depicting an example of schematic configuration of a vehicle control system.

FIG. 25 is a diagram of assistance in explaining an example of installation positions of an outside-vehicle information detecting section and an imaging section.

FIG. 26 is a schematic diagram illustrating a configuration of an evaluating apparatus (BL46XU).

FIG. 27 is a 2D-GIXD measurement diagram of Sample 1.

FIG. 28 is an intensity profile diagram of a horizontal orientation component of Sample 1.

FIG. 29 is a characteristic diagram illustrating a relationship between a film formation temperature and orientation in each organic semiconductor material obtained by 2D-GIXD.

FIG. 30 is a characteristic diagram illustrating a relationship between orientation and quantum efficiency in each organic semiconductor material obtained by 2D-GIXD.

FIG. 31 is a characteristic diagram illustrating a relationship between orientation and a response speed in each organic semiconductor material obtained by 2D-GIXD.

FIG. 32 is a characteristic diagram illustrating a relationship between an orientation variation rate and quantum efficiency in each organic semiconductor material obtained by 2D-GIXD.

FIG. 33 is a characteristic diagram illustrating a relationship between an orientation variation rate and a response speed in each organic semiconductor material obtained by 2D-GIXD.

FIG. 34 is a scattering spectrum diagram of each film formation temperature of DP-DTT obtained by XRD.

FIG. 35 is a scattering spectrum diagram of each film formation temperature of DBP-DTT obtained by XRD.

FIG. 36 is a characteristic diagram illustrating a relationship between a film formation temperature and an orientation angle in each organic semiconductor material obtained by pMAIRS.

FIG. 37 is a characteristic diagram illustrating a relationship between an orientation angle variation amount and quantum efficiency in each organic semiconductor material obtained by pMAIRS.

FIG. 38 is a characteristic diagram illustrating a relationship between an orientation angle variation amount and a response speed in each organic semiconductor material obtained by pMAIRS.

MODES FOR CARRYING OUT THE INVENTION

The following describes embodiments of the present disclosure in detail with reference to the drawings. The following description is a specific example of the present disclosure, and the present disclosure is not limited to the following embodiments. In addition, the present disclosure is not limited to arrangement, dimensions, dimensional ratios, and the like of the constituent elements illustrated in the drawings. It is to be noted that the description is given in the following order.
1. First Embodiment
(An example of a photoelectric conversion device using an organic semiconductor material whose orientation is difficult to be varied)
   1-1. Configuration of Photoelectric Conversion Device
   1-2. Method of Manufacturing Photoelectric Conversion Device
   1-3. Workings and Effects
2. Second Embodiment
(An example of a photoelectric conversion device with a lower electrode including a plurality of electrodes)
   2-1. Configuration of Photoelectric Conversion Device
   2-2. Method of Manufacturing Photoelectric Conversion Device
   2-3. Workings and Effects
3. Application examples
4. Working Examples

1. FIRST EMBODIMENT

FIG. 1 Illustrates a cross-sectional configuration of a photoelectric conversion device (photoelectric conversion device 10A) according to a first embodiment of the present disclosure. The photoelectric conversion device 10A is, for example, an imaging device that configures a single pixel (unit pixel P) in an imaging apparatus (imaging apparatus 1) such as a CCD (Charge Coupled Device) image sensor or a CMOS (Complementary Metal Oxide Semiconductor) image sensor of a back illumination type (back light receiving type) (see FIG. 19). The photoelectric conversion device 10A is of a so-called vertical spectroscopic type in which a single organic photoelectric conversion section 11G and two inorganic photoelectric conversion sections 11B and 11R are stacked in a vertical direction. The organic photoelectric conversion section 11G and the two inorganic photoelectric conversion sections 11B and 11R selectively detect light in different wavelength ranges to perform photoelectric conversion. The organic photoelectric conversion section 11G has a configuration in which a lower electrode 15, a photoelectric conversion layer 16, and an upper electrode 17 are stacked in this order. In the present embodiment, the photoelectric conversion layer 16 is formed using an organic semiconductor material that allows, for example, variation in a ratio of horizontally-oriented crystal and vertically-oriented crystal in the photoelectric conversion layer 16 to be three times or less between a case where film formation is performed at a first temperature and a case where the film formation is performed at a second temperature higher than the first temperature.

(1-1. Configuration of Photoelectric Conversion Device)

In the photoelectric conversion device 10A, one organic photoelectric conversion section 11G and two inorganic photoelectric conversion sections 11B and 11R are stacked in the vertical direction for each unit pixel P. The organic photoelectric conversion section 11G is provided on back surface (first surface 11S1) side of the semiconductor substrate 11. The inorganic photoelectric conversion sections 11B and 11R are formed to be embedded in the semiconductor substrate 11, and are stacked in a thickness direction of the semiconductor substrate 11. The organic photoelectric conversion section 11G includes a photoelectric conversion layer 16 including a p-type semiconductor and an n-type semiconductor and having a bulk heterojunction structure in the layer. The bulk heterojunction structure has a p/n junction surface formed by mixing of the p-type semiconductor and the n-type semiconductor.

The organic photoelectric conversion section 11G and the inorganic photoelectric conversion sections 11B and 11R selectively detect light in wavelength bands different from each other to perform photoelectric conversion. Specifically, the organic photoelectric conversion section 11G acquires a green (G) color signal. The inorganic photoelectric conversion sections 11B and 11R respectively acquire a blue (B) color signal and a red (R) color signal on the basis of a difference in absorption coefficient. This enables the photoelectric conversion device 10A to acquire a plurality types of color signals in a single pixel without using a color filter.

It is to be noted that, in the present embodiment, a case where a hole is read as a signal charge out of a pair of an electron and a hole generated by photoelectric conversion (a case where a p-type semiconductor region is used as a photoelectric conversion layer) will be described. In addition, in the diagram, "+ (plus)" assigned to "p" or "n" represents that impurity concentration of the p-type or the n-type is high, and "++" represents that the impurity concentration of the p-type or the n-type is even higher than "+".

The semiconductor substrate 11 includes, for example, an n-type silicon (Si) substrate and has a p-well 61 in a predetermined region. A second surface (front surface of the semiconductor substrate 11) 11S2 of the p-well 61 is provided with, for example, various floating diffusions (floating diffusion layers) FD (e.g., FD1, FD2, and FD3), various transistors Tr (e.g., a vertical transistor (transfer transistor) Tr1, a transfer transistor Tr2, an amplifying transistor (modulating device) AMP, and a reset transistor RST), and a multilayer wiring 70. The multilayer wiring 70 has a configuration in which wiring layers 71, 72, and 73 are stacked in an insulating layer 74, for example. In addition, in a peripheral portion of the semiconductor substrate 11, a peripheral circuit (not illustrated) including a logic circuit or the like is provided.

It is to be noted that, in FIG. 1, the first surface 11S1 side of the semiconductor substrate 11 is described as a light entering surface 51, and the second surface 11S2 side is described as wiring layer side S2.

The inorganic photoelectric conversion sections 11B and 11R each include, for example, a PIN (Positive Intrinsic Negative) type photodiode, and each has a p-n junction at a predetermined region of the semiconductor substrate 11. The inorganic photoelectric conversion sections 11B and 11R are capable of performing spectroscopy of light in the vertical direction by using the fact that the wavelength band to be absorbed differs depending on a light entering depth in a silicon substrate.

The inorganic photoelectric conversion section 11B selectively detects blue light to store signal charges corresponding to blue and is provided at a depth that allows for efficient photoelectric conversion of the blue light. The inorganic photoelectric conversion section 11R selectively detects red light to store signal charges corresponding to red and is provided at a depth that allows for efficient photoelectric conversion of the red light. It is to be noted that blue (B) is a color corresponding to a wavelength band of, for example, from 450 nm to 495 nm, and red (R) is a color corresponding to a wavelength band of, for example, from 620 nm to 750 nm. It is sufficient that the inorganic photoelectric conversion sections 11B and 11R are each able to detect light of a wavelength band of a portion or all of each wavelength band.

Specifically, as illustrated in FIG. 1, each of the inorganic photoelectric conversion section 11B and the inorganic photoelectric conversion section 11R has, for example, a p+ region serving as a hole storage layer and an n-region serving as an electron storage layer (has a p-n-p stack structure). The n-region of the inorganic photoelectric conversion section 11B is coupled to a vertical transistor Tr1. The p+ region of the inorganic photoelectric conversion section 11B is bent along the vertical transistor Tr1 and is coupled to the p+ region of the inorganic photoelectric conversion section 11R.

As described above, the second surface 11S2 of the semiconductor substrate 11 is provided with, for example, the floating diffusions (floating diffusion layers) FD1, FD2, and FD3, the vertical transistor (transfer transistor) Tr1, the transfer transistor Tr2, the amplifying transistor (modulating device) AMP, and the reset transistor RST.

The vertical transistor Tr1 is a transfer transistor that transfers, to the floating diffusion FD1, a signal charge (here, a hole) corresponding to blue generated and stored in the inorganic photoelectric conversion section 11B. The inorganic photoelectric conversion section 11B is formed at a deep position from the second surface 11S2 of the semiconductor substrate 11. Therefore, it is preferable that the transfer transistor of the inorganic photoelectric conversion section 11B include the vertical transistor Tr1.

The transfer transistor Tr2 transfers, to the floating diffusion FD2, a signal charge (here, a hole) corresponding to red generated and stored in the inorganic photoelectric conversion section 11R. The transfer transistor Tr2 includes, for example, a MOS transistor.

The amplifying transistor AMP is a modulating device that modulates, into a voltage, an amount of the charges generated in the organic photoelectric conversion section 11G. The amplifying transistor AMP includes a MOS transistor, for example.

The reset transistor RST resets the charges transferred from the organic photoelectric conversion section 11G to the floating diffusion FD3, and includes a MOS transistor, for example.

A lower first contact 75, a lower second contact 76, and an upper contact 13B each include, for example, a doped silicon material such as PDAS (Phosphorus Doped Amorphous Silicon), or a metal material such as aluminum (Al), tungsten (W), titanium (Ti), cobalt (Co), hafnium (Hf), or tantalum (Ta).

The organic photoelectric conversion section 11G is provided on the first surface 11S1 side of the semiconductor substrate 11. The organic photoelectric conversion section 11G has a configuration in which, for example, the lower electrode 15, the photoelectric conversion layer 16, and the upper electrode 17 are stacked in this order from the first surface 51 side of the semiconductor substrate 11. The lower electrode 15 is formed separately for each unit pixel P, for example. The photoelectric conversion layer 16 and the upper electrode 17 are provided as continuous layers shared by a plurality of unit pixels P and provided for each plurality of unit pixels P (for example, a pixel unit 1a of the imaging apparatus 1 illustrated in FIG. 19). The organic photoelectric conversion section 11G is an organic photoelectric conversion device that absorbs green light corresponding to a portion or all of a selective wavelength band (for example, 450 nm or more and 650 nm or less) to generate an electron-hole pair.

Between the first surface 11S1 of the semiconductor substrate 11 and the lower electrode 15, for example, interlayer insulating layers 12 and 14 are stacked in this order from the semiconductor substrate 11 side. The interlayer insulating layer has a configuration in which, for example, a layer (fixed charge layer) 12A having a fixed charge and a dielectric layer 12B having an insulation property are stacked. A protective layer 18 is provided on the upper electrode 17. Above the protective layer 18, an on-chip lens layer 19 is disposed. The on-chip lens layer 19 configures an on-chip lens 19L and also serves as a planarization layer.

A through electrode 63 is provided between the first surface 11S1 and the second surface 11S2 of the semiconductor substrate 11. The organic photoelectric conversion section 11G is coupled to a gate Gamp of the amplifying transistor AMP and the floating diffusion FD3 via this through electrode 63. As a result, in the photoelectric conversion device 10A, the charges generated in the organic photoelectric conversion section 11G on the first surface 11S1 side of the semiconductor substrate 11 can be favorably transferred to the second surface 11S2 side of the semiconductor substrate 11 via the through electrode 63, and the characteristics can be improved.

The through electrode 63 is provided for each organic photoelectric conversion section 11G of the photoelectric conversion device 10A, for example. The through electrode 63 has a function of a connector for the organic photoelectric conversion section 11G and each of the gate Gamp of the amplifying transistor AMP and the floating diffusion FD3. The through electrode 63 also serves as a transmission path of the charges generated in the organic photoelectric conversion section 11G.

A lower end of the through electrode 63 is coupled to a coupling portion 71A in the wiring layer 71, for example. The coupling portion 71A and the gate Gamp of the amplifying transistor AMP are coupled to each other via the lower first contact 75. The coupling portion 71A and the floating diffusion FD3 are coupled to the lower electrode 15 via the lower second contact 76. It is to be noted that, although FIG. 1 illustrates the through electrode 63 in a columnar shape, the through electrode 63 is not limited thereto, and may have a tapered shape, for example.

It is preferable that, as illustrated in FIG. 1, a reset gate Grst of the reset transistor RST be disposed next to the floating diffusion FD3. This makes it possible to reset, by the reset transistor RST, the charges stored in the floating diffusion FD3.

In the photoelectric conversion device 10A of the present embodiment, light entering the organic photoelectric conversion section 11G from the upper electrode 17 side is absorbed by the photoelectric conversion layer 16. An exciton generated thereby moves to an interface between an electron donor and an electron acceptor configuring the photoelectric conversion layer 16, and undergoes exciton dissociation, i.e., is separated into an electron and a hole. The charges (the electron and the hole) generated here are transported to different electrodes by diffusion resulting from a difference in carrier concentration or an inner electric field resulting from a difference in work function between an anode (here, the lower electrode 15) and a cathode (here, the upper electrode 17), and are detected as a photocurrent. In addition, application of a potential between the lower electrode 15 and the upper electrode 17 makes it possible to control a transport direction of the electron and the hole.

In the following, description is given of configurations or materials of respective units.

The organic photoelectric conversion section 11G is an organic photoelectric conversion device that absorbs green light corresponding to a portion or all of a selective wavelength band (450 nm or more and 750 nm or less, for example) to generate an electron-hole pair. As described above, the organic photoelectric conversion section 11G includes, for example, the lower electrode 15 and the upper electrode 17 which are opposed to each other, and the photoelectric conversion layer 16 which is provided between the lower electrode 15 and the upper electrode 17.

The lower electrode 15 is provided in a region that is opposed to light receiving surfaces of the inorganic photoelectric conversion sections 11B and 11R formed in the semiconductor substrate 11 and covers these light receiving surfaces. The lower electrode 15 includes a metal oxide having light transparency. As the metal atom included in the metal oxide used as a material of the lower electrode 15, tin (Sn), zinc (Zn), indium (In), silicon (Si), zirconium (Zr), aluminum (Al), gallium (Ga), tungsten (W), chromium (Cr), cobalt (Co), nickel (Ni), tantalum (Ta), niobium (Nb), and molybdenum (Mo) can be mentioned. As the metal oxide including one or more types of the above-described metal atoms, ITO (indium tin oxide) can be mentioned. However, as the material included in the lower electrode 15, a tin-oxide ($SnO_2$)-based material obtained by adding a dopant or a zinc-oxide-based material formed by adding a dopant to aluminum zinc oxide (ZnO) may be used in addition to this ITO. As the zinc-oxide-based material, aluminum zinc oxide (AZO) in which aluminum (Al) is added as a dopant, gallium zinc oxide (GZO) in which gallium (Ga) is added, and indium zinc oxide (IZO) in which indium (In) is added can be mentioned. In addition, CuI, $InSbO_4$, ZnMgO, $CuInO_2$, $MgIN_2O_4$, CdO, $ZnSnO_3$, or the like may be used other than the above.

The photoelectric conversion layer 16 converts optical energy into electric energy, and includes, for example, two or more types of organic semiconductor materials. In the present embodiment, the photoelectric conversion layer 16 includes an organic semiconductor material (one organic semiconductor material) whose orientation is difficult to be changed in accordance with temperature. As the one organic semiconductor material, for example, a material that allows, for example, variation in a ratio of horizontally-oriented crystal and vertically-oriented crystal in the photoelectric conversion layer 16 to be three times or less between a case where film formation is performed at a first temperature and a case where the film formation is performed at a second temperature higher than the first temperature. Here, a difference between the first temperature and the second temperature is, for example, 5° C. or greater and 35° C. or smaller, preferably 20° C. or greater and 30° C. or smaller, more preferably 20° C. or greater and 25° C. or smaller. As an example of the first temperature, −10° C. or higher and +10° C. or lower can be mentioned. Preferably, it is −5° C. or higher and +5° C. or lower, and more preferably −2° C. or higher and +2° C. or lower. As an example of the second temperature, 15° C. or higher and 35° C. or lower can be mentioned. Preferably, it is 20° C. or higher and 30° C. or lower, and more preferably, 23° C. or higher and 27° C. or lower.

Further, as the one organic semiconductor material, for example, a material can be mentioned that allows a variation amount of an orientation angle to be smaller than 10° between the case where the film formation is performed at the first temperature and the case where the film formation is performed at the second temperature higher than the first temperature. Here, the orientation angle is an angle formed by the one organic semiconductor material in the photoelectric conversion layer 16 with respect to an electrode surface of the lower electrode 15. Further, as the one organic semiconductor material, for example, a material can be mentioned that allows an angle range (orientation angle range) of the orientation angle formed with the electrode surface of the lower electrode 15 to be smaller than 46°. It is to be noted that the lower limits of the orientation variation amount and the orientation angle range are each 0°. The one organic semiconductor material is, for example, a low molecular weight material having a molecular weight of 100 or greater and 3000 or smaller and having a carrier transporting property (a hole transporting property or an electron transporting property).

As the one organic semiconductor material, for example, a molecular length (l) is preferably greater than 1.6 nm and equal to or smaller than 10 nm. More preferably, it is 1.8 nm or greater and 10 nm or smaller, and further more preferably, it is 2.4 nm or greater and 10 nm or smaller. The molecular width (w) is preferably as small as possible. Here, the molecular length (l) is the maximum length of the space occupied by the molecule. Specifically, the molecular length (l) corresponds to a distance from a hydrogen (H) atom at an end of one biphenyl group to a hydrogen (H) atom at an end of the other biphenyl group in two biphenyl groups bonded to a skeleton portion, as illustrated in FIG. 2, for example, in DBP-DTT represented by formula (1-1) to be described later and DBP-NDT represented by formula (17-1), which are examples of the one organic semiconductor material in the present embodiment. The molecular width (w) is a size in a direction orthogonal to the molecular length (l).

As the one organic semiconductor material described above, for example, it is preferable to have in-plane anisotropy and a 7E conjugate plane in the molecule. Specifically, a compound having an aromatic skeleton and an aromatic substituent in the molecule is preferable. As the aromatic substituent configuring the one organic semiconductor material, for example, for example, a biphenyl group, a triphenyl group, a terphenyl group, a stilbene group, a naphthyl group, an anthracenyl group, a phenanthrenyl group, a pyrenyl group, a perylenyl group, a tetracenyl group, a chrysenyl group, a fluorenyl group, an acenaphthasenyl group, a triphenylene group, a fluoranthene group, and the like that have carbon number of 6 or more and 60 or less can be mentioned. Specifically, the following formulae (A-1) to (A-50) and the like can be mentioned.

[Chem. 1]

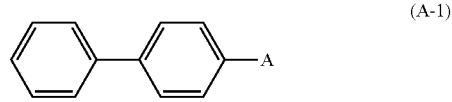

(A-1)

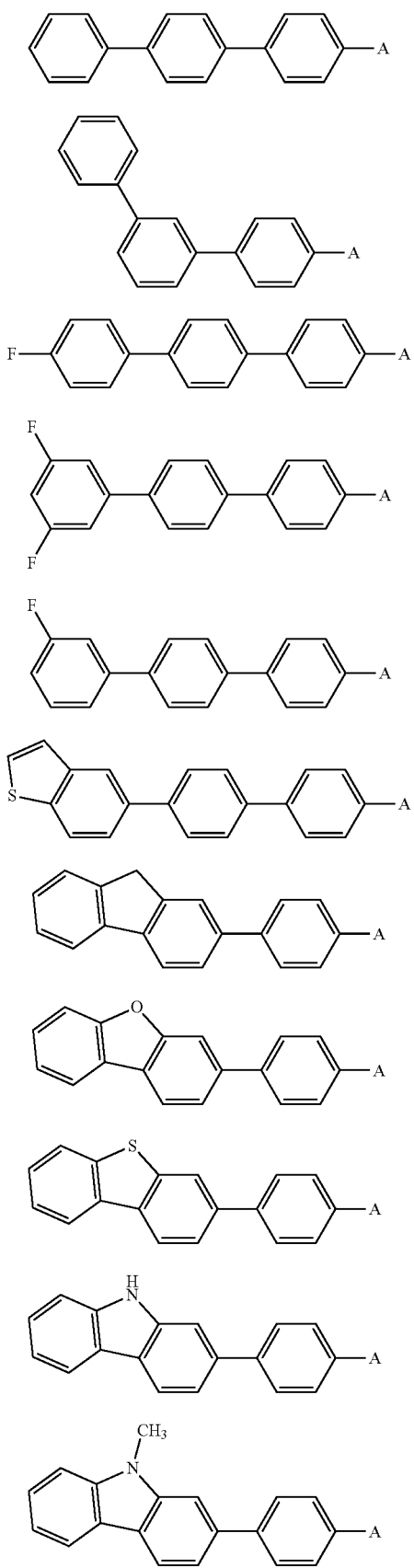
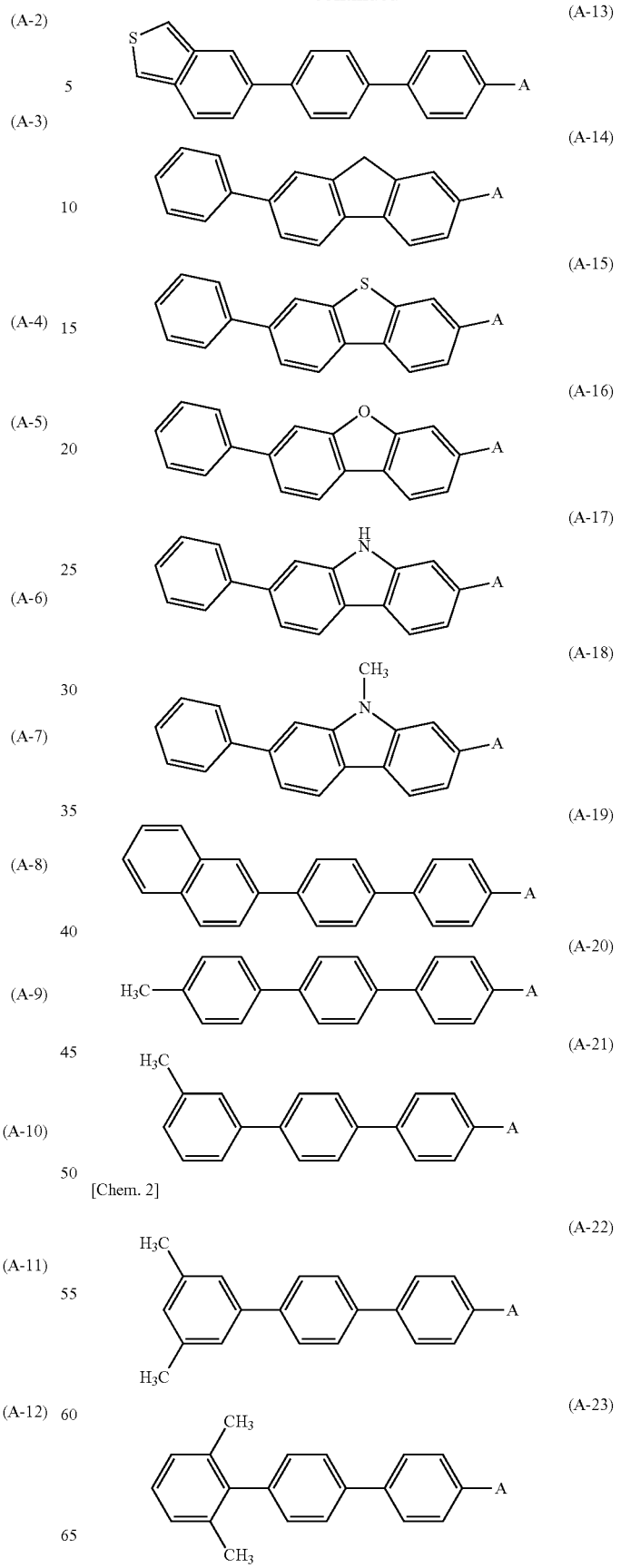
[Chem. 2]

(A-24) 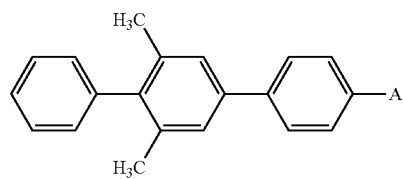
(A-25) 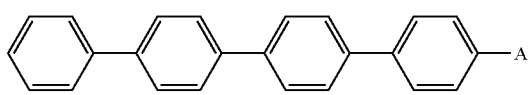
(A-26) 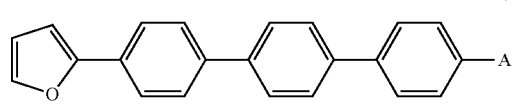
(A-27) 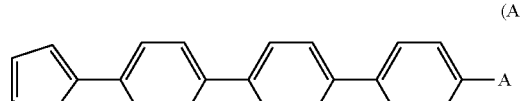
(A-28) 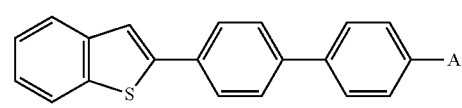
(A-29) 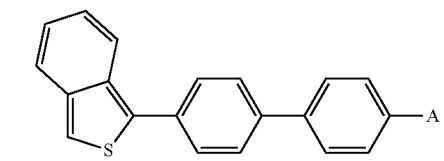
(A-30) 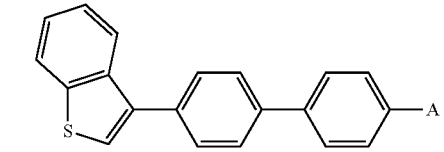
(A-31) 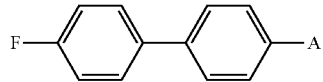
(A-32) 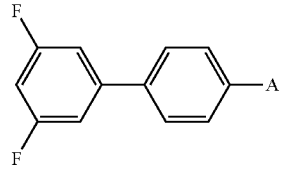
(A-33) 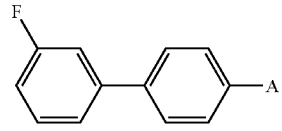
(A-34) 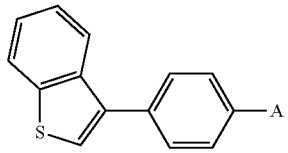
(A-35) 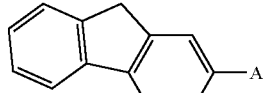
(A-36) 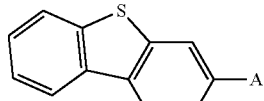
(A-37) 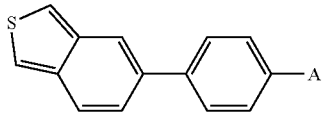
(A-38) 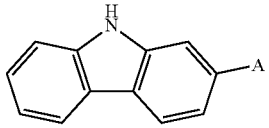
(A-39) 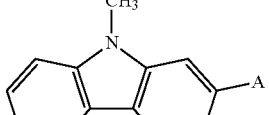
(A-40) 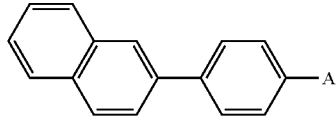
(A-41) 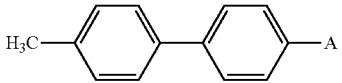
(A-42) 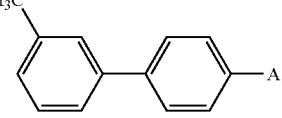
(A-43) 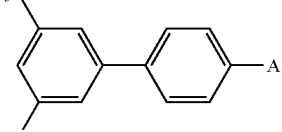
(A-44) 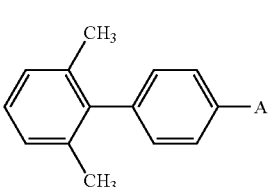
(A-45) 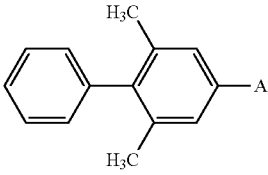

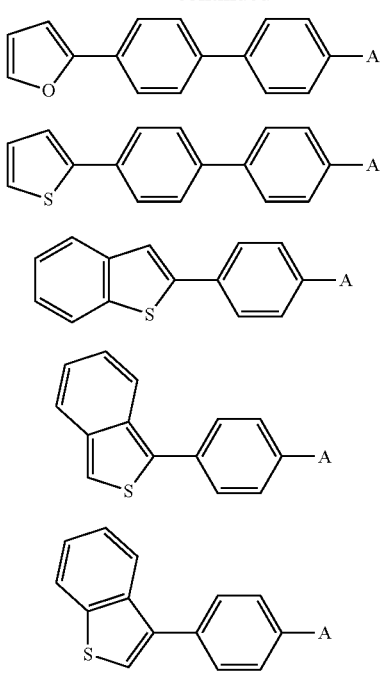

(A-46)

(A-47)

(A-48)

(A-49)

(A-50)

It is preferable that the one organic semiconductor material having a hole transporting property have a HOMO level higher than a HOMO level of at least one type of another organic semiconductor material (described later) included in the photoelectric conversion layer 16. As the one organic semiconductor material described above, a compound having a monocyclic or polycyclic heteroaromatic skeleton can be mentioned. As an example, a compound having a skeleton represented by the following general formula (1) can be mentioned.

[Chem. 3]

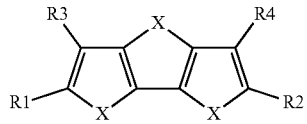

(1)

(X is any of oxygen (O), sulfur (S), selenium (Se), and tellurium (Te).)

The substituents listed in the above formulae (A-1) to (A-30) are introduced into R1 and R2 of the above general formula (1). R3 and R4 are each independently a hydrogen atom, a halogen atom, a straight-chain, branched, or cyclic alkyl group, an aryl group, or a derivative thereof. Any adjacent ones of R1 to R4 may be bonded to each other to form a condensed aliphatic ring or a condensed aromatic ring. The condensed aliphatic ring or condensed aromatic ring may include one or more atoms of oxygen (O), nitrogen (N), sulfur (S), selenium (Se), and tellurium (Te).

As specific examples of the one organic semiconductor material having the skeleton represented by the above general formula (1), for example, a compound of the following formula (1-1) having the above formula (A-1) for each of R1 and R2 and a compound of formula (1-2) having the above formula (A-2) for each of R1 and R2 can be mentioned.

[Chem. 4]

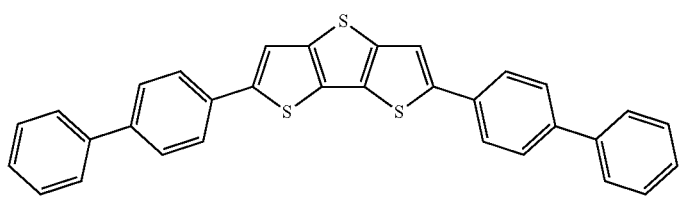

(1-1)

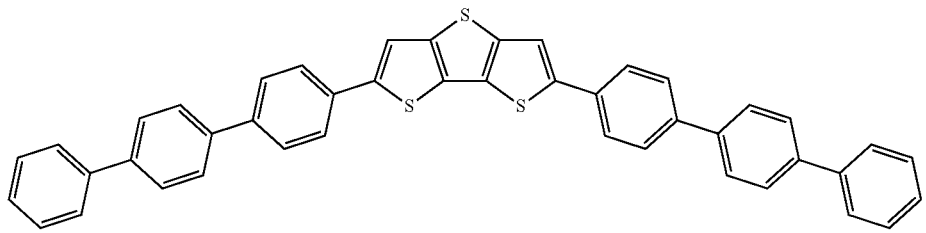

(1-2)

In addition, as the one organic semiconductor material having the hole transporting property, a compound having a skeleton represented by the following general formulae (2) to (17) can be mentioned.
[Chem. 5]
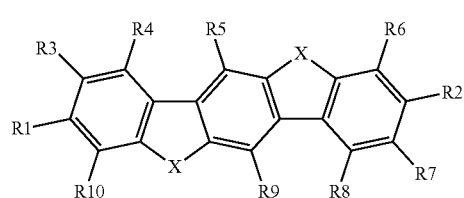 (2)
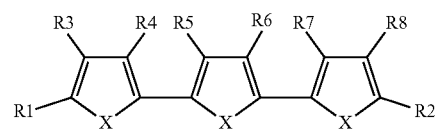 (3)
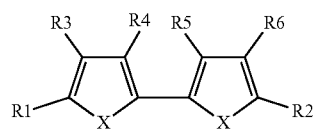 (4)
(5)
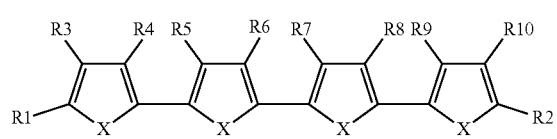 (6)
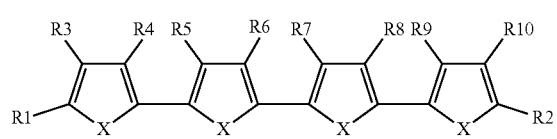 (7)
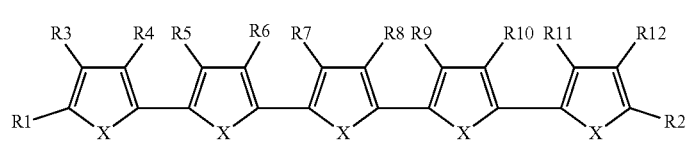 (8)
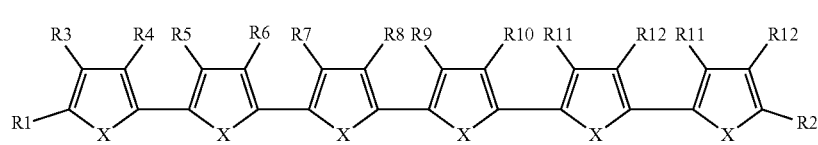
[Chem. 6]
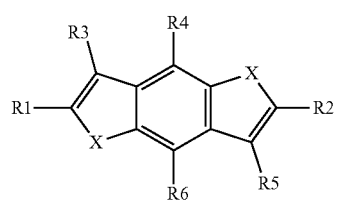 (9)
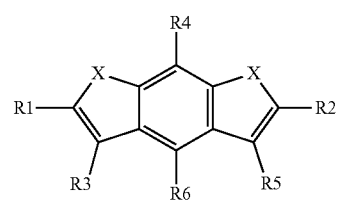 (10)
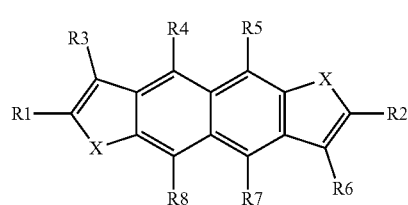 (11)
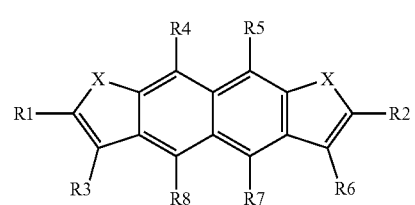 (12)
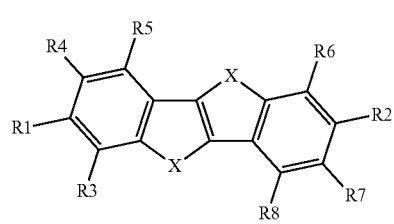 (13)
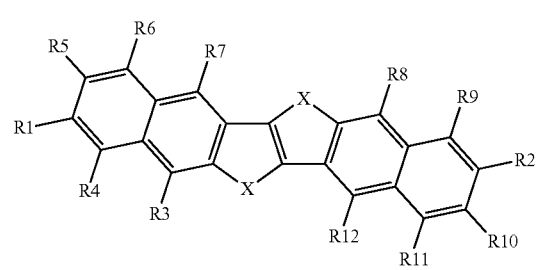 (14)

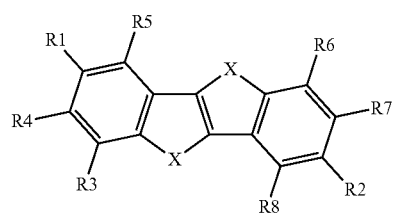
(15)

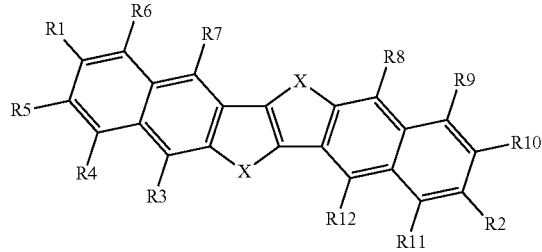
(16)

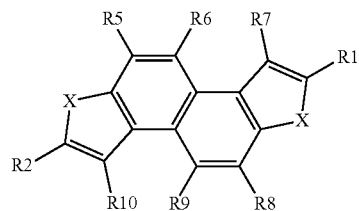
(17)

X in the above general formulae (2) to (17) is any of oxygen (O), sulfur (S), selenium (Se), and tellurium (Te). The substituents listed in the above formulae (A-1) to (A-30) are introduced into R1 and R2. R3 to R14 are each independently a hydrogen atom, a halogen atom, a straight-chain, branched, or cyclic alkyl group, an aryl group, or a derivative thereof. Any adjacent ones of R3 to R14 may be bonded to each other to form a condensed aliphatic ring or a condensed aromatic ring. The condensed aliphatic ring or the condensed aromatic ring may include one or more atoms of oxygen (O), nitrogen (N), sulfur (S), selenium (Se), and tellurium (Te).

As the one organic semiconductor material having the electron transporting property, for example, as with the organic semiconductor material having the hole transporting property, it is preferable to have a π conjugate plane in a molecule together with in-plane anisotropy. In addition, it is preferable that the one organic semiconductor material having the electron transporting property have a LUMO level lower than a LUMO level of at least one type of the other organic semiconductor material included in the photoelectric conversion layer 16. As such a material, a perylenetetracarboxylic acid diimide derivative, a naphthalenetetracarboxylic acid diimide derivative, a fluoropentacene derivative, and the like can be mentioned.

Further, as the other organic semiconductor material, the photoelectric conversion layer 16 includes, for example, a color material having an absorption coefficient of 50000 cm$^{-1}$ or more in a selective wavelength (for example, green light of 400 nm or more and 750 nm or less) of a visible light region. Thereby, the organic photoelectric conversion section 11G can selectively perform photoelectric conversion of green light of 400 nm or more and 750 nm or less, for example. As such another organic semiconductor material, for example, subphthalocyanine or a derivative thereof represented by the following general formula (18) can be mentioned.

[Chem. 7]

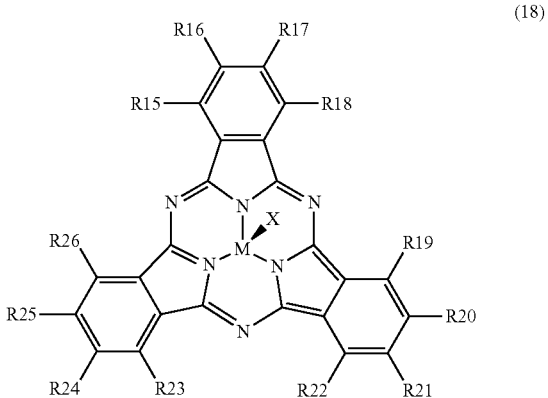
(18)

(R15 to R26 are each independently selected from a group consisting of a hydrogen atom, a halogen atom, a straight-chain, branched, or cyclic alkyl group, a thioalkyl group, a thioaryl group, an arylsulfonyl group, an alkylsulfonyl group, an amino group, an alkylamino group, an arylamino group, a hydroxy group, an alkoxy group, an acylamino group, an acyloxy group, a phenyl group, a carboxy group, a carboxamide group, a carboalkoxy group, an acyl group, a sulfonyl group, a cyano group, and a nitro group, and any adjacent ones of R15 to R26 may be a portion of a condensed aliphatic ring or a condensed aromatic ring. The condensed aliphatic ring or the condensed aromatic ring may include one or more atoms other than carbon. M is boron, divalent metal, or trivalent metal. X is a substituent selected from a group consisting of halogen, a hydroxy group, a thiol group, an imide group, a substituted or unsubstituted alkoxy group, a substituted or unsubstituted aryloxy group, a substituted or unsubstituted alkyl group, a substituted or unsubstituted alkylthio group, and a substituted or unsubstituted arylthio group.)

In addition, as the other organic semiconductor material, it is preferable that the photoelectric conversion layer 16 include an organic semiconductor material which has transparency with respect to visible light and has a carrier transporting property to be paired with the one organic semiconductor material, for example. For example, in a case where the above-mentioned organic semiconductor material having the hole transporting property is used as the one organic semiconductor material, for example, $C_{60}$ fullerene or a derivative thereof represented by the following general formula (19), or $C_{70}$ fullerene or a derivative thereof represented by the following general formula (20) can be mentioned as the material having the electron transporting property. It is to be noted that, here, fullerene is considered as an organic semiconductor.

[Chem. 8]

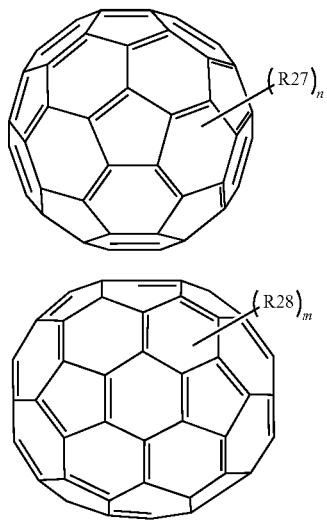

(19)

(20)

(R27 and R28 are each a hydrogen atom, a halogen atom, a straight-chain, branched, or cyclic alkyl group, a phenyl group, a group having a straight-chain or condensed aromatic compound, a group having a halide, a partial fluoroalkyl group, a perfluoroalkyl group, a silylalkyl group, a silylalkoxy group, an arylsilyl group, an arylsulfanyl group, an alkylsulfanyl group, an arylsulfonyl group, an alkylsulfonyl group, an arylsulfide group, an alkylsulfide group, an amino group, an alkylamino group, an arylamino group, a hydroxy group, an alkoxy group, an acylamino group, an acyloxy group, a carbonyl group, a carboxy group, an carboxyamino group, a carboalkoxy group, an acyl group, a sulfonyl group, a cyano group, a nitro group, a group having a chalcogenide, a phosphine group, a phosphone group, or a derivative thereof. "n" and "m" are each an integer of 0 or greater.)

The photoelectric conversion layer 16 has a junction surface (p/n junction surface) between a p-type semiconductor and an n-type semiconductor in the layer. The p-type semiconductor relatively functions as an electron donor (donor) and the n-type semiconductor relatively functions as an electron acceptor (acceptor). The photoelectric conversion layer 16 provides a field in which excitons generated when absorbing light are separated into electrons and holes. The excitons are separated into electrons and holes at an interface (p/n junction surface) between the electron donor and the electron acceptor. A thickness of the photoelectric conversion layer 16 is, for example, 50 nm to 500 nm.

As with the lower electrode 15, the upper electrode 17 includes a conducting film having light transparency. In the photoelectric conversion device 10A, the upper electrode 17 may be separated for each unit pixel P, or may be formed as a shared electrode for each unit pixel P. A thickness of the upper electrode 17 is 10 nm to 200 nm, for example.

It is to be noted that other layers may be provided between the photoelectric conversion layer 16 and the lower electrode 15 and between the photoelectric conversion layer 16 and the upper electrode 17. Specifically, for example, an undercoat layer, a hole transport layer, an electron block layer, the photoelectric conversion layer 16, a hole block layer, a buffer layer, an electron transport layer, a work function adjusting layer, and the like may be stacked in order from the lower electrode 15 side.

The fixed charge layer 12A may be a film having a positive fixed charge or a film having a negative fixed charge. As a material of the film having the negative fixed charge, hafnium oxide ($HfO_2$), aluminum oxide ($Al_2O_3$), zirconium oxide ($ZrO_2$), tantalum oxide ($Ta_2O_5$), titanium oxide ($TiO_2$), and the like can be mentioned. In addition, as materials other than the aforementioned materials, lanthanum oxide, praseodymium oxide, cerium oxide, neodymium oxide, promethium oxide, samarium oxide, europium oxide, gadolinium oxide, terbium oxide, dysprosium oxide, holmium oxide, thulium oxide, ytterbium oxide, lutetium oxide, yttrium oxide, an aluminum nitride film, a hafnium oxynitride film, an aluminum oxynitride film, or the like may be used.

The fixed charge layer 12A may have a configuration in which two or more types of films are stacked. This makes it possible to further improve a function as a hole storage layer in a case of the film having the negative fixed charge, for example.

A material of the dielectric layer 12B is not particularly limited. For example, it is formed of a silicon oxide film, a TEOS film, a silicon nitride film, a silicon oxynitride film, or the like.

The interlayer insulating layer 14 includes, for example, a single-layer film including one type of silicon oxide (SiO), silicon nitride (SiN), silicon oxynitride (SiON), and the like, or a laminated film including two or more types thereof.

The protective layer 18 includes a material having light transparency. The protective layer 18 includes, for example, a single-layer film including any of silicon oxide, silicon nitride, silicon oxynitride, and the like, or a laminated film including two or more types thereof. This protective layer 18 has a thickness of 100 nm to 30000 nm, for example.

On the protective layer 18, the on-chip lens layer 19 is so formed as to cover the entire surface thereof. A plurality of on-chip lenses 19L (micro-lenses) is provided on a surface of the on-chip lens layer 19. The on-chip lenses 19L collect light entering from the above on each of the light receiving surfaces of the organic photoelectric conversion section 11G, and the inorganic photoelectric conversion sections 11B and 11R. In the present embodiment, since the multilayer wiring 70 is formed on the second surface 11S2 side of the semiconductor substrate 11, the light receiving surfaces of the organic photoelectric conversion section 11G and the inorganic photoelectric conversion sections 11B and 11R can be disposed close to each other. Therefore, it is possible to reduce variation, in sensitivity between the colors, which occurs depending on the F-values of the on-chip lenses 19L.

FIG. 3 is a plan view illustrating a configuration example of the photoelectric conversion device 10A in which a plurality of photoelectric conversion sections (e.g., the inorganic photoelectric conversion sections 11B and 11R and the organic photoelectric conversion section 11G described above) to which the technology according to the present disclosure can be applied are stacked. That is, FIG. 3 illustrates an example of a planar configuration of the unit pixel P configuring the pixel unit 1a illustrated in FIG. 19, for example.

The unit pixel P includes a photoelectric conversion region 1100 in which a red photoelectric conversion section (the inorganic photoelectric conversion section 11R in FIG. 1), a blue photoelectric conversion section (the inorganic photoelectric conversion section 11B in FIG. 1), and a green photoelectric conversion section (the organic photoelectric conversion section 11G in FIG. 1) (neither of which is illustrated in FIG. 3) are stacked in three layers in order of the green photoelectric conversion section, the blue photoelectric conversion section, and the red photoelectric conversion section from the light receiving surface (the light entering surface S1 in FIG. 1) side. The red photoelectric conversion section, the blue photoelectric conversion section, and the green photoelectric conversion section perform photoelectric conversion on light having wavelengths of R (Red), G (Green), and B (Blue), respectively. Further, the unit pixel P includes a Tr group 1110, a Tr group 1120, and a Tr group 1130 as charge reading sections that read out charges corresponding to light of wavelengths of R, G, and B from the red photoelectric conversion section, the green photoelectric conversion section, and the blue photoelectric conversion section, respectively. In the imaging apparatus 1, in one unit pixel P, vertical spectroscopy, that is, spectroscopy of light of R, G, and B is performed in layers staked in the photoelectric conversion region 1100 and serving as the red photoelectric conversion section, the green photoelectric conversion section, and the blue photoelectric conversion section, respectively.

The Tr group 1110, the Tr group 1120, and the Tr group 1130 are formed around the photoelectric conversion region 1100. The Tr group 1110 outputs, as a pixel signal, a signal charge corresponding to the R light generated and stored in the red photoelectric conversion section. The Tr group 1110 includes a transfer Tr (MOS FET) 1111, a reset Tr 1112, an amplifying Tr 1113, and a selection Tr 1114. The Tr group 1120 outputs, as a pixel signal, a signal charge corresponding to the B light generated and stored in the blue photoelectric conversion section. The Tr group 1120 includes a transfer Tr 1121, a reset Tr 1122, an amplifying Tr 1123, and a selection Tr 1124. The Tr group 1130 outputs, as a pixel signal, a signal charge corresponding to the G light generated and stored in the green photoelectric conversion section. The Tr group 1130 includes a transfer Tr 1131, a reset Tr 1132, an amplifying Tr 1133, and a selection Tr 1134.

The transfer Tr 1111 includes a gate G, a source/drain region S/D, and (a source/drain region serving as) a FD (floating diffusion) 1115. The transfer Tr 1121 includes a gate G, a source/drain region S/D, and a FD 1125. The transfer Tr 1131 includes a gate G, (a source/drain region S/D coupled to) the green photoelectric conversion section in the photoelectric conversion region 1100, and a FD 1135. It is to be noted that the source/drain region of the transfer Tr 1111 is coupled to the red photoelectric conversion section of the photoelectric conversion region 1100, and the source/drain region S/D of the transfer Tr 1121 is coupled to the blue photoelectric conversion section of the photoelectric conversion region 1100.

Each of the reset Trs 1112, 1132, and 1122, the amplifying Trs 1113, 1133, and 1123, and the selection Trs 1114, 1134, and 1124 includes a gate G and a pair of source/drain regions S/D so disposed as to sandwich the gate G The FDs 1115, 1135, and 1125 are coupled to the source/drain regions S/D, which are the sources of the reset Trs 1112, 1132, and 1122, respectively, and are coupled to the gates G of the amplifying Trs 1113, 1133, and 1123, respectively. A power supply Vdd is coupled to each of the source/drain region S/D shared by the reset Tr 1112 and the amplifying Tr 1113, the source/drain region S/D shared by the reset Tr1132 and the amplifying Tr1133, and the source/drain region S/D shared by the reset Tr 1122 and the amplifying Tr 1123. A VSL (vertical signal line) is coupled to the source/drain regions S/D serving as sources of the respective selection Trs 1114, 1134, and 1124.

The technology according to the present disclosure can be applied to the above-described photoelectric conversion device.

(1-2. Method of Manufacturing Photoelectric Conversion Device)

It is possible to manufacture the photoelectric conversion device 10A of the present embodiment, for example, in the following manner.

FIG. 4 and FIG. 5 illustrate the method of manufacturing the photoelectric conversion device 10A in order of process. First, as illustrated in FIG. 4, for example, the p-well 61, is formed as a well of a first conductivity type in the semiconductor substrate 11 and the inorganic photoelectric conversion sections 11B and 11R of the second conductivity type (for example, n-type) are formed in this p-well 61. The p+ region is formed in the vicinity of the first surface 11S1 of the semiconductor substrate 11.

As also illustrated in FIG. 4, n+regions to serve as the floating diffusions FD1 to FD3 are formed on the second surface 11 S2 of the semiconductor substrate 11. Thereafter, a gate insulating layer 62 and a gate wiring layer 64 are formed. The gate wiring layer 64 includes gates of the vertical transistor Tr1, the transfer transistor Tr2, the amplifying transistor AMP, and the reset transistor RST. Thereby, the vertical transistor Tr1, the transfer transistor Tr2, the amplifying transistor AMP, and the reset transistor RST are formed. Further, the lower first contact 75, the lower second contact 76, and the multilayer wiring 70 are formed on the second surface 11S2 of the semiconductor substrate 11. The multilayer wiring 70 includes the insulating layer 74 and the wiring layers 71 to 73 including the coupling portion 71A.

As a base of the semiconductor substrate 11, for example, an SOI (Silicon on Insulator) substrate is used in which the semiconductor substrate 11, an embedded oxide film (not illustrated), and a holding substrate (not illustrated) are stacked. Although not illustrated in FIG. 4, the embedded oxide film and the holding substrate are joined to the first substrate surface 11S1 of the semiconductor substrate 11. After ion implantation, an annealing process is performed.

Thereafter, a support substrate (not illustrated), another semiconductor substrate, or the like is joined to the second surface 11S2 side (the multilayer wiring 70 side) of the semiconductor substrate 11 and flipped vertically. Subsequently, the semiconductor substrate 11 is separated from the embedded oxide film and the holding substrate of the SOI substrate to cause the first surface 11S1 of the semiconductor substrate 11 to be exposed. It is possible to perform the aforementioned processes by a technique used in a usual CMOS process such as ion implantation or CVD (Chemical Vapor Deposition).

Thereafter, as illustrated in FIG. 5, the semiconductor substrate 11 is processed from the first surface 11S1 side, for example, by dry etching to form an annular opening 63H. The opening 63H has a depth penetrating from the first surface 11S1 to the second surface 11S2 of the semiconductor substrate 11 as illustrated in FIG. 5, and reaching the coupling portion 71A, for example.

Subsequently, as illustrated in FIG. 5, for example, the negative fixed charge layer 12A is formed on the first surface 11S1 of the semiconductor substrate 11 and a side surface of the opening 63H. Two or more types of films may be stacked as the negative fixed charge layer 12A. This makes it possible to further improve the function as the hole storage layer. The dielectric layer 12B is formed after the negative fixed charge layer 12A is formed.

Next, an electric conductor is buried in the opening 63H to form the through electrode 63. As the electric conductor, for example, a metal material such as aluminum (Al), tungsten (W), titanium (Ti), cobalt (Co), hafnium (Hf), or tantalum (Ta) is usable in addition to the doped silicon material such as PDAS (Phosphorus Doped Amorphous Silicon).

Subsequently, after a pad portion 13A is formed on the through electrode 63, the interlayer insulating layer 14 is formed on the dielectric layer 12B and the pad portion 13A. In the interlayer insulating layer 14, an upper contact 13B and a pad portion 13C are provided on the pad portion 13A. The upper contact 13B and the pad portion 13C electrically couple the lower electrode 15 and the through electrode 63 (specifically, the pad portion 13A on the through electrode 63).

Next, the lower electrode 15, the photoelectric conversion layer 16, the upper electrode 17, and the protective layer 18 are formed in this order on the interlayer insulating layer 14. The photoelectric conversion layer 16 is formed by, for example, depositing the above-mentioned three types of organic semiconductor materials by, for example, a vacuum evaporation method. Finally, the on-chip lens layer 19 having the plurality of on-chip lenses 19L on its surface is disposed. Thereby, the photoelectric conversion device 10A illustrated in FIG. 1 is completed.

It is to be noted that, as described above, in a case where another organic layer (e.g., an electron blocking layer or the like) is formed as an upper layer or a lower layer of the photoelectric conversion layer 16, it is desirable to form them continuously (by a vacuum consistent process) in the vacuum process. Further, the method of depositing the photoelectric conversion layer 16 is not necessarily limited to a method using a vacuum evaporation method, and another method, for example, a spin coating technique, a printing technique, or the like may be used.

In the photoelectric conversion device 10A, when light enters the organic photoelectric conversion section 11G via the on-chip lens 19L, the light passes through the organic photoelectric conversion section 11G, and the inorganic photoelectric conversion sections 11B and 11R in this order, and in the course of the passage, the light is subjected to the photoelectric conversion for each of the green, blue, and red light. In the following, description is given of an acquisition operation of each color signal.

(Acquisition of Green Signal by Organic Photoelectric Conversion Section 11G)

Of the light entering the photoelectric conversion device 10A, first, green light is selectively detected (absorbed) and photoelectrically converted by the organic photoelectric conversion section 11G.

The organic photoelectric conversion section 11G is coupled to the gate Gamp of the amplifying transistor AMP and the floating diffusion FD3 via the through electrode 63. Therefore, holes of the electron-hole pair generated in the organic photoelectric conversion section 11G are taken out from the lower electrode 15 side, transferred to the second surface 11S2 side of the semiconductor substrate 11 via the through electrode 63, and stored in the floating diffusion FD3. Simultaneously with this, the amplifying transistor AMP modulates the amount of the charges generated in the organic photoelectric conversion section 11G into a voltage.

In addition, the reset gate Grst of the reset transistor RST is disposed next to the floating diffusion FD3. This causes the reset transistor RST to reset the charges stored in the floating diffusion FD3.

Here, the organic photoelectric conversion section 11G is coupled to not only the amplifying transistor AMP, but also to the floating diffusion FD3 via the through electrode 63. Therefore, it is possible for the reset transistor RST to easily reset the charges stored in the floating diffusion FD3.

In contrast to this, in a case where the through electrode 63 and the floating diffusion FD3 are not coupled to each other, it is difficult to reset the charges stored in the floating diffusion FD3 and the charges are pulled out to the upper electrode 17 side by application of a large voltage. Therefore, the photoelectric conversion layer 16 may be damaged. Moreover, a structure that enables resetting in a short period of time leads to increased dark-time noise and results in a trade-off. Therefore, this structure is difficult.

(Acquisition of Blue Signal and Red Signal by Inorganic Photoelectric Conversion Sections 11B and 11R)

Subsequently, of the light passing through the organic photoelectric conversion section 11G, the blue light and the red light are absorbed in order and photoelectrically converted in the inorganic photoelectric conversion section 11B and the inorganic photoelectric conversion section 11R, respectively. In the inorganic photoelectric conversion section 11B, electrons corresponding to the entering blue light are stored in the n-region of the inorganic photoelectric conversion section 11B and the stored electrons are transferred to the floating diffusion FD1 by the vertical transistor Tr1. Similarly, in the inorganic photoelectric conversion section 11R, electrons corresponding to the entering red light are stored in the n-region of the inorganic photoelectric conversion section 11R and the stored electrons are transferred to the floating diffusion FD2 by the transfer transistor Tr2.

(1-3. Workings and Effects)

As described above, in an organic photoelectric conversion device used in an organic thin film solar cell, an organic imaging device, or the like, a bulk heterostructure in which a p-type organic semiconductor and an n-type organic semiconductor are mixed is employed. However, since organic semiconductors have low conductivity characteristics, the organic photoelectric conversion device cannot obtain sufficient quantum efficiency. Therefore, there is a problem that an electric output signal tends to be delayed with respect to the entering light.

Generally, it is known that molecular orientation is important for conduction of organic semiconductors. This is similarly applicable to an organic photoelectric conversion device having a bulk heterostructure. FIG. 6 illustrates orientation and anisotropy of conduction of organic molecules. (A) of FIG. 6 illustrates a state in which a plurality of organic molecules is vertically oriented with respect to the substrate 100. (B) of FIG. 6 illustrates a state in which a plurality of organic molecules is horizontally oriented with respect to the substrate 100. The conduction of the organic molecules has anisotropy. As illustrated in FIG. 6, the conductivity is higher in the direction in which the 7E conjugate system is stacked (arrow direction) and lower in the direction orthogonal to the arrow direction. Therefore, in the organic photoelectric conversion device, as illustrated in (B) of FIG. 6, it is preferable that the π conjugate system is stacked horizontally with respect to the substrate.

However, if the organic molecules are only simply oriented horizontally with respect to the substrate, the conduction property of the organic photoelectric conversion device may not be sufficiently improved, and the quantum efficiency and responsiveness may not be sufficiently improved in some cases. In a photoelectric conversion device having a bulk heterostructure, it is desired that each material configuring the bulk heterostructure in the layer forms an appropriate grain. For example, in a case where a large defect is present at the grain boundary, the conduction property is greatly degraded. One reason for this is that charge is trapped at a trap level of the defect or the defect becomes an energy barrier to inhibit charge transfer between grains when the charge conduct at the grain boundary. This is considered to lead to deterioration in quantum efficiency and response speed.

In contrast, in the present embodiment, the photoelectric conversion layer 16 is formed using at least one type of organic semiconductor material having crystallinity. This organic semiconductor material allows variation in a ratio between horizontally-oriented crystal and vertically-oriented crystal in the photoelectric conversion layer 16 to be three times or less between the case where film formation is performed at the first temperature and the case where the film formation is performed at the second temperature higher than the first temperature.

FIG. 7 schematically illustrates crystals of the plurality of organic molecules oriented as illustrated in FIG. 6 ((A) of FIG. 6 and (B) of FIG. 6). FIG. 8 schematically illustrates crystals of the above-mentioned organic semiconductor material in the photoelectric conversion layer 16 of the present embodiment, and also illustrates conduction of charges (e.g., holes (h$^+$)). As illustrated in FIG. 8, when the number of horizontally-oriented crystals is large, holes (h$^+$) generated in the photoelectric conversion layer 16 by light application advantageously conduct in the vertical direction (arrow direction) of the substrate 100. In the present embodiment, by using the organic semiconductor material having the above-mentioned property as the material of the photoelectric conversion layer 16, the ratio of the horizontally-oriented crystal and the vertically-oriented crystal of the above-mentioned organic semiconductor material in the bulk heterostructure configuring the photoelectric conversion layer 16 can be appropriately controlled. Therefore, formation of a defect at the grain boundary can be reduced.

As described above, in the photoelectric conversion device 10A of the present embodiment, the photoelectric conversion layer 16 is formed using the organic semiconductor material that allows variation in the ratio between the horizontally-oriented crystal and the vertically-oriented crystal in the layer to be three times or less between the case where film formation is performed at the first temperature and the case where the film formation is performed at the second temperature higher than the first temperature, or using the organic semiconductor material that allows the variation amount of the angle formed with the electrode surface of the lower electrode 15 to be smaller than 10° between the foregoing cases. This reduces the formation of a defect at the grain boundary of the bulk heterostructure configuring the photoelectric conversion layer 16 and enables improvement in quantum efficiency and responsiveness.

In addition, in the photoelectric conversion device 10A of the present embodiment, by using, as the one organic semiconductor material, for example, the above-described material that allows the variation amount of the orientation angle to be smaller than 10° between the case where film formation is performed at the first temperature and the case where the film formation is performed at the second temperature higher than the first temperature and also allows the orientation angle range to be smaller than 46° between the case where film formation is performed at the first temperature and the case where the film formation is performed at the second temperature higher than the first temperature, it is possible to further improve a response speed. In addition, robustness (durability) to the film formation temperature of the photoelectric conversion layer 16 can be improved.

Next, the second embodiment will be described. Hereinafter, the similar components to those of the first embodiment described above are denoted by the same reference numerals, and description thereof is omitted as appropriate.

2. SECOND EMBODIMENT

FIG. 9 illustrates a cross-sectional configuration of a photoelectric conversion device (photoelectric conversion device 10B) of a second embodiment of the present disclosure. FIG. 10 is an equivalent circuit diagram of the photoelectric conversion device 10B illustrated in FIG. 9. FIG. 11 schematically shows arrangement of the lower electrode 21 and transistors configuring the control unit of the photoelectric conversion device 10B illustrated in FIG. 9. As with the photoelectric conversion device 10A, the photoelectric conversion device 10B is an imaging device that configures one pixel (unit pixel P) in an imaging apparatus (imaging apparatus 1) such as a CCD image sensor or a CMOS image sensor of a back illumination type (back surface light receiving type), for example. The photoelectric conversion device 10B is of a so-called vertical spectroscopic type in which a single organic photoelectric conversion section 20 and two inorganic photoelectric conversion sections 32B and 32R are stacked in the vertical direction. The organic photoelectric conversion section 20 and the inorganic photoelectric conversion sections 32B and 32R selectively detect light in different wavelength ranges to perform photoelectric conversion.

(2-1. Configuration of Photoelectric Conversion Device)

The organic photoelectric conversion section 20 is provided on first surface (back surface) 30A side of a semiconductor substrate 30. The inorganic photoelectric conversion sections 32B and 32R are formed to be embedded in the semiconductor substrate 30, and are stacked in a thickness direction of the semiconductor substrate 30. In the organic photoelectric conversion section 20 of the present embodiment, the lower electrode 21 includes a plurality of electrodes (a read electrode 21A and a storage electrode 21B) and a charge storage layer 23 is provided between the lower electrode 21 and the photoelectric conversion layer 24.

The organic photoelectric conversion section 20 and the inorganic photoelectric conversion sections 32B and 32R selectively detect light of wavelength ranges different from each other to perform photoelectric conversion. For example, the organic photoelectric conversion section 20 acquires a color signal of green (G). The inorganic photoelectric conversion sections 32B and 32R respectively acquire a color signal of blue (B) and a color signal of red (R), on the basis of a difference in absorption coefficient. This enables the photoelectric conversion device 10B to acquire a plurality types of color signals in a single pixel without using a color filter.

A second surface (front surface) 30B of the semiconductor substrate 30 is provided with, for example, a floating diffusion FD1 (a region 36B in the semiconductor substrate 30), a floating diffusion FD2 (a region 37C in the semiconductor substrate 30), a floating diffusion FD3 (a region 38C in the semiconductor substrate 30), transfer transistors Tr2 and Tr3, an amplifying transistor AMP, a reset transistor RST, a selection transistor SEL, and a multilayer wiring 40. The multilayer wiring 40 has a configuration in which, for example, wiring layers 41, 42, and 43 are stacked in an insulating layer 44.

It is to be noted that, in FIG. 9, the first surface 30A side of the semiconductor substrate 30 is described as light entering side S1, and the second surface 30B side is described as wiring layer side S2.

The organic photoelectric conversion section 20 has a configuration in which, for example, the lower electrode 21, the charge storage layer 23, the photoelectric conversion layer 24, and the upper electrode 25 are stacked in this order from the first surface 30A side of the semiconductor substrate 30. It is to be noted that an insulating layer 22 is provided between the lower electrode 21 and the charge storage layer 23. The lower electrode 21 is formed separately for each photoelectric conversion device 10B, for example, and has a read electrode 21A and a storage electrode 21B separated from each other by the insulating layer 22, which will be described later in detail. The insulating layer 22 on the read electrode 21A is provided with an opening 22H, and the read electrode 21A and the charge storage layer 23 are electrically coupled to each other via the opening 22H. It is to be noted that, although FIG. 9 illustrates an example in which the charge storage layer 23, the photoelectric conversion layer 24, and the upper electrode 25 are formed separately for each photoelectric conversion device 10B, for example, they may be provided as continuous layers shared by a plurality of photoelectric conversion devices 10B. As in the first embodiment, for example, a fixed charge layer 51, a dielectric layer 52, and an interlayer insulating layer 26 are provided between the first surface 30A of the semiconductor substrate 30 and the lower electrode 21. On the upper electrode 25, the protective layer 18 including a light shielding film 28 is provided. An optical member such as the on-chip lens layer 19 having the on-chip lens 19L is disposed on the protective layer 18.

A through electrode 53 is provided between the first surface 30A and the second surface 30B of the semiconductor substrate 30. The organic photoelectric conversion section 20 is coupled to the gate Gamp of the amplifying transistor AMP and one source/drain region 36B of the reset transistor RST (reset transistor Tr1rst) also serving as the floating diffusion FD1 via the through electrode 53. As a result, in the photoelectric conversion device 10B, charges (e.g., electrons) generated in the organic photoelectric conversion section 20 on the first surface 30A side of the semiconductor substrate 30 can be favorably transferred to the second surface 30B side of the semiconductor substrate 30 via the through electrode 53. It is thereby possible to improve the property.

A lower end of the through electrode 53 is coupled to a coupling portion 41A in a wiring layer 41. The coupling portion 41A and the gate Gamp of the amplifying transistor AMP are coupled to each other via a lower first contact 45. The coupling portion 41A and the floating diffusion FD1 (the region 36B) are coupled to each other via a lower second contact 46, for example. An upper end of the through electrode 53 is coupled to the read electrode 21A via a pad portion 39A and an upper first contact 27A, for example.

A reset gate Grst of the reset transistor RST is disposed next to the floating diffusion FD1 (one source/drain region 36B of the reset transistor RST). This makes it possible to reset, by the reset transistor RST, the charges stored in the floating diffusion FD1.

In the photoelectric conversion device 10B of the present embodiment, as with the photoelectric conversion device 10A, the light entering the organic photoelectric conversion section 20 from the upper electrode 25 side is absorbed by the photoelectric conversion layer 24. An exciton generated thereby moves to an interface between an electron donor and an electron acceptor configuring the photoelectric conversion layer 24, and undergoes exciton dissociation, i.e., is separated into an electron and a hole. The charges (the electron and the hole) generated here are transported to different electrodes by diffusion resulting from a difference in carrier concentration or an inner electric field resulting from a difference in work function between an anode and a cathode, and are detected as a photocurrent. In addition, application of a potential between the lower electrode 21 and the upper electrode 25 makes it possible to control a transport direction of the electron and the hole.

In the following, description is given of configurations, materials, and the like of respective units.

The organic photoelectric conversion section 20 is an organic photoelectric conversion device that absorbs green light corresponding to a portion or all of a selective wavelength band (450 nm or more and 650 nm or less, for example) to generate an electron-hole pair.

As described above, the lower electrode 21 includes the read electrode 21A and the storage electrode 21B which are formed separately. The read electrode 21A is directed to transferring of charges (here, electrons) generated in the photoelectric conversion layer 24 to the floating diffusion FD1. The read electrode 21A is coupled to the floating diffusion FD1 (36B) via, for example, the upper first contact 27A, the pad portion 39A, the through electrode 53, the coupling portion 41A, and the lower second contact 46. The storage electrode 21B is directed to storing electrons as signal charges in the charge storage layer 23 among the charges generated in the photoelectric conversion layer 24, and directed to transferring the stored electrons to the read electrode 21A. The storage electrode 21B is provided in a region that is opposed to the light receiving surfaces of the inorganic photoelectric conversion sections 32B and 32R formed in the semiconductor substrate 30 and cover the light receiving surfaces. The storage electrode 21B is preferably larger than the read electrode 21A. This allows more charges to be stored in the charge storage layer 23.

The lower electrode 21 includes a conducting film having light transparency and includes, for example, ITO (indium-tin oxide). However, as a material included in the lower electrode 21, a tin-oxide ($SnO_2$)-based material obtained by adding a dopant or a zinc-oxide-based material formed by adding a dopant to aluminum zinc oxide (ZnO) may be used in addition to this ITO. As the zinc-oxide-based material, for example, aluminum zinc oxide (AZO) in which aluminum (Al) is added as a dopant, gallium zinc oxide (GZO) in which gallium (Ga) is added, and indium zinc oxide (IZO) in which indium (In) is added can be mentioned. In addition, CuI, $InSbO_4$, ZnMgO, $CuInO_2$, $MgIn_2O_4$, CdO, $ZnSnO_3$, or the like may be used.

The insulating layer 22 is directed to electrically isolating the storage electrode 21B and the charge storage layer 23 from each other. The insulating layer 22 is so provided, for example, on the interlayer insulating layer 26 as to cover the lower electrode 21. Further, the insulating layer 22 is provided with an opening 22H on the read electrode 21A of the lower electrode 21. The read electrode 21A and the charge storage layer 23 are electrically coupled to each other via the opening 22H. The insulating layer 22 can be formed using, for example, a material similar to that of the interlayer insulating layer 26. The insulating layer 22 includes, for example, a single-layer film including one type of silicon oxide, silicon nitride, silicon oxynitride (SiON), and the like, or a laminated film including two or more types thereof. A thickness of the insulating layer 22 is, for example, 20 nm to 500 nm.

The charge storage layer 23 is provided in a lower layer of the photoelectric conversion layer 24, specifically, between the insulating layer 22 and the photoelectric conversion layer 24. The charge storage layer 23 is directed to storing signal charges (here, electrons) generated in the photoelectric conversion layer 24. As the charge storage layer 23, an oxide semiconductor material, an organic semiconductor material, and the like can be mentioned. A thickness of the charge storage layer 23 is, for example, 10 nm or greater and 300 nm or smaller.

The photoelectric conversion layer 24 converts optical energy into electric energy, and includes, for example, two or more types of organic semiconductor materials. As with the photoelectric conversion layer 16 in the first embodiment described above, the photoelectric conversion layer 24 includes the organic semiconductor material (the one organic semiconductor material) whose orientation is not easily varied in accordance with temperature. As the one organic semiconductor material, for example, a material can be mentioned that allows, for example, variation in a ratio of horizontally-oriented crystal and vertically-oriented crystal in the photoelectric conversion layer 16 to be three times or less between a case where film formation is performed at a first temperature (for example, −10° or higher and +10° or lower) and a case where the film formation is performed at a second temperature (for example, 15° or higher and 35° or lower) higher than the first temperature.

Further, as the one organic semiconductor material, for example, a material can be mentioned that allows a variation amount of an orientation angle is smaller than 10° between the case where the film formation is performed at the first temperature and the case where the film formation is performed at the second temperature higher than the first temperature. Further, as the one organic semiconductor material, for example, a material can be mentioned that an angle range (orientation angle range) of the orientation angle formed with the electrode surface of the lower electrode 21 is smaller than 46°. It is to be noted that the lower limits of the orientation variation amount and the orientation angle range are each 0°. The one organic semiconductor material is, for example, a low molecular weight material having a molecular weight of 100 or greater and 3000 or smaller and having a carrier transporting property (a hole transporting property or an electron transporting property).

As the one organic semiconductor material, as described above, for example, the molecular length (l) is preferably greater than 1.6 nm and equal to or smaller than 10 nm. More preferably, it is 1.8 nm or greater and 10 nm or smaller, and still more preferably, it is 2.4 nm or greater and 10 nm or smaller. The molecular width (w) is preferably as small as possible.

As the one organic semiconductor material described above, for example, it is preferable to have in-plane anisotropy and a π conjugate plane in the molecule. Specifically, a compound having an aromatic skeleton and an aromatic substituent in the molecule is preferable. As the aromatic substituent configuring the one organic semiconductor material, for example, for example, a phenyl group, a biphenyl group, a triphenyl group, a terphenyl group, a stilbene group, a naphthyl group, an anthracenyl group, a phenanthrenyl group, a pyrenyl group, a perylenyl group, a tetracenyl group, a chrysenyl group, a fluorenyl group, an acenaphthasenyl group, a triphenylene group, a fluoranthene group, and the like having carbon number of 6 or more and 60 or less can be mentioned. Specifically, the above formulae (A-1) to (A-30) and the like can be mentioned.

It is preferable that the one organic semiconductor material having a hole transporting property have a HOMO level higher than a HOMO level of at least one type of another organic semiconductor material included in the photoelectric conversion layer 16. As the one organic semiconductor material described above, a compound having a monocyclic or polycyclic heteroaromatic skeleton can be mentioned, and for one example, a compound having a skeleton represented by the above general formula (1) can be mentioned.

The substituents listed in the above formulae (A-1) to (A-30) are introduced into R1 and R2 of the above general formula (1). R3 and R4 are each independently a hydrogen atom, a halogen atom, a straight-chain, branched, or cyclic alkyl group, an aryl group, or a derivative thereof. Any adjacent ones of R1 to R4 may be bonded to each other to form a condensed aliphatic ring or a condensed aromatic ring. The condensed aliphatic ring or the condensed aromatic ring may include one or more atoms of oxygen (O), nitrogen (N), sulfur (S), selenium (Se), and tellurium (Te).

As specific examples of the one organic semiconductor material having a skeleton represented by the above general formula (1), for example, a compound of the following formula (1-1) having the above formula (A-1) for each of R1 and R2 and a compound of formula (1-2) having the above formula (A-2) for each of R1 and R2.

In addition, as the one organic semiconductor material having the hole transporting property, a compound having a skeleton represented by the foregoing general formulae (2) to (17) can be mentioned.

As with the first embodiment, X in the above general formulae (2) to (17) is any of oxygen (O), sulfur (S), selenium (Se), and tellurium (Te). The substituents listed in the above formulae (A-1) to (A-30) are introduced into R1 and R2. R3 to R14 are each independently a hydrogen atom, a halogen atom, a straight-chain, branched, or cyclic alkyl group, an aryl group, or a derivative thereof. Any adjacent ones of R3 to R14 may be bonded to each other to form a condensed aliphatic ring or a condensed aromatic ring. The condensed aliphatic ring or the condensed aromatic ring may include one or more atoms of oxygen (O), nitrogen (N), sulfur (S), selenium (Se), and tellurium (Te).

As the one organic semiconductor material having the electron transporting property, for example, as with the organic semiconductor material having the hole transporting property described above, it is preferable to have a π conjugate plane in a molecule together with in-plane anisotropy. In addition, it is preferable that the one organic semiconductor material having the electron transporting property have a LUMO level lower than a LUMO level of at least one type of the other organic semiconductor material included in the photoelectric conversion layer 24. As such a material, a perylenetetracarboxylic acid diimide derivative, a naphthalenetetracarboxylic acid diimide derivative, a fluoropentacene derivative, and the like can be mentioned.

Further, as the other organic semiconductor material, the photoelectric conversion layer 24 includes, for example, a color material having an absorption coefficient of 50000 $cm^{-1}$ or more in a selective wavelength (for example, green light of 400 nm or more and 750 nm or less) of a visible light region. Thereby, the organic photoelectric conversion section 11G can selectively perform photoelectric conversion of green light of 400 nm or more and 750 nm or less, for example. As such another organic semiconductor material, for example, subphthalocyanine or a derivative thereof represented by the foregoing general formula (18) can be mentioned.

In addition, as the other organic semiconductor material, it is preferable that the photoelectric conversion layer 16 include an organic semiconductor material which has transparency with respect to visible light and has a carrier transporting property to be paired with the one organic semiconductor material, for example. For example, in a case where the above-mentioned organic semiconductor material having the hole transporting property is used as the one organic semiconductor material, for example, $C_{60}$ fullerene or a derivative thereof represented by the foregoing general formula (19), or $C_{70}$ fullerene or a derivative thereof represented by the following general formula (20) can be mentioned as the material having the electron transporting property. It is to be noted that, here, fullerene is considered as an organic semiconductor.

As with the first embodiment, the upper electrode 25 includes a conducting film having light transparency. In the photoelectric conversion device 10B, the upper electrode 25 may be separated for each unit pixel P, or may be formed as a shared electrode for each unit pixel P. The upper electrode 25 has a thickness of 10 nm to 200 nm, for example.

It is to be noted that other layers may be provided between the photoelectric conversion layer 24 and the lower electrode 21 and between the photoelectric conversion layer 24 and the upper electrode 25, as with the photoelectric conversion device 10A.

In the present embodiment, for example, the light shielding film 28 is provided on the read electrode 21A in the protective layer 18. It is sufficient that the light shielding film 28 is so provided as not to cover at least the storage electrode 21B and cover at least a region of the read electrode 21A that is directly in contact with the charge storage layer 23. For example, it is preferable to so provide it with a size slightly larger than the conductive film 21a which is formed in the same layer as the storage electrode 21B. On the protective layer 18, the on-chip lens layer 19 is so formed as to cover the entire surface thereof, as with the above-described photoelectric conversion device 10A. A plurality of on-chip lenses 19L (micro-lenses) is provided on a surface of the on-chip lens layer 19.

The semiconductor substrate 30 includes, for example, an n-type silicon (Si) substrate and has a p-well 31 in a predetermined region. The second surface 30B of the p-well 31 is provided with the above-described transfer transistors Tr2 and Tr3, the amplifying transistor AMP, the reset transistor RST, the selection transistor SEL, and the like. In addition, in a peripheral portion of the semiconductor substrate 30, a peripheral circuit (not illustrated) including a logic circuit or the like is provided.

The reset transistor RST (reset transistor Tr1rst) resets charges transferred from the organic photoelectric conversion section 20 to the floating diffusion FD1, and includes, for example, a MOS transistor. More specifically, the reset transistor Tr1rst includes a reset gate Grst, a channel formation region 36A, and source/drain regions 36B and 36C. The reset gate Grst is coupled to a reset line RST1. One source/drain region 36B of the reset transistor also serves as the floating diffusion FD1. The other source/drain region 36C configuring the reset transistor Tr1rst is coupled to the power supply VDD.

The amplifying transistor AMP is a modulator that modulates, into a voltage, an amount of the charges generated in the organic photoelectric conversion section 20, and includes a MOS transistor, for example. Specifically, the amplifying transistor AMP includes a gate Gamp, a channel formation region 35A, and source/drain regions 35B and 35C. The gate Gamp is coupled to the read electrode 21A and the one source/drain region 36B (floating diffusion FD1) of the reset transistor Tr1rst via the lower first contact 45, the coupling portion 41A, the lower second contact 46, the through electrode 53, and the like. Further, one source/drain region 35B shares a region with the other source/drain region 36C configuring the reset transistor Tr1rst, and is coupled to the power supply VDD.

The selection transistor SEL (selection transistor TR1sel) includes a gate Gsel, a channel formation region 34A, and source/drain regions 34B and 34C. The gate Gsel is coupled to the select line SEL1 Further, one source/drain region 34B shares a region with the other source/drain region 35C configuring the amplifying transistor AMP, and the other source/drain region 34C is coupled to a signal line (data output line) VSL1.

Each of the inorganic photoelectric conversion sections 32B and 32R has a p-n junction in a predetermined region of the semiconductor substrate 30. The inorganic photoelectric conversion sections 32B and 32R make it possible to perform spectroscopy of light in the vertical direction by utilizing the fact that wavelengths of light to be absorbed vary depending on a depth of light entering the silicon substrate. The inorganic photoelectric conversion section 32B selectively detects the blue light to store the signal charge corresponding to blue and is installed at a depth at which efficient photoelectric conversion of the blue light is possible. The inorganic photoelectric conversion section 32R selectively detects red light to store a signal charge corresponding to red and is provided at a depth that allows for efficient photoelectric conversion of the red light. It is to be noted that blue (B) is a color corresponding to a wavelength range of, for example, from 450 nm to 495 nm, and red (R) is a color corresponding to a wavelength range of, for example, from 620 nm to 750 nm. It is sufficient that the inorganic photoelectric conversion sections 32B and 32R are able to detect light of a wavelength range of a portion or all of the respective wavelength ranges.

The inorganic photoelectric conversion section 32B has, for example, a p+ region that is to be a hole storage layer, and an n-region that is to be an electron storage layer. The inorganic photoelectric conversion section 32R has, for example, a p+ region that is to be a hole storage layer, and an n-region that is to be an electron storage layer (has a p-n-p stacked structure). The n-region of the inorganic photoelectric conversion section 32B is coupled to the vertical transfer transistor Tr2. The p+ region of the inorganic photoelectric conversion section 32B is bent along the transfer transistor Tr2 and is coupled to the p+ region of the inorganic photoelectric conversion section 32R.

The transfer transistor Tr2 (transfer transistor TR2trs) is directed to transferring, to the floating diffusion FD2, the signal charges corresponding to blue, which are generated and stored in the inorganic photoelectric conversion section 32B. The inorganic photoelectric conversion section 32B is formed at a deep position from the second surface 30B of the semiconductor substrate 30. Therefore, it is preferable that the transfer transistor TR2trs of the inorganic photoelectric conversion section 32B include a vertical transistor. Further, the transfer transistor TR2trs is coupled to the transfer gate line TG2. Further, the floating diffusion FD2 is provided in the region 37C in the vicinity of the gate Gtrs2 of the transfer transistor TR2trs. The charges stored in the inorganic photoelectric conversion section 32B are read out to the floating diffusion FD2 via the transmission channel formed along the gate Gtrs2.

The transfer transistor Tr3 (transfer transistor TR3trs) transfers, to the floating diffusion FD3, the signal charges corresponding to red which are generated and stored in the inorganic photoelectric conversion section 32R. The transfer transistor Tr3 includes, for example, a MOS transistor. Further, the transfer transistor TR3trs is coupled to the transfer gate line TG3. Further, a floating diffusion FD3 is provided in the region 38C in the vicinity of the gate Gtrs3 of the transfer transistor TR3trs. The charges stored in the inorganic photoelectric conversion section 32R are read out to the floating diffusion FD3 via the transmission channel formed along the gate Gtrs3.

The second surface 30B side of the semiconductor substrate 30 is further provided with a reset transistor TR2rst, an amplifying transistor TR2amp, and a selection transistor TR2sel which configure a control unit of the inorganic photoelectric conversion section 32B. In addition, a reset transistor TR3rst, an amplifying transistor TR3amp, and a selection transistor TR3sel which configure a control unit of the inorganic photoelectric conversion section 32R are provided.

The reset transistor TR2rst includes a gate, a channel formation region, and a source/drain region. The gate of the reset transistor TR2rst is coupled to the reset line RST2, and one source/drain region of the reset transistor TR2rst is coupled to the power supply VDD. The other source/drain region of the reset transistor TR2rst also serves as the floating diffusion FD2.

The amplifying transistor TR2amp includes a gate, a channel formation region, and a source/drain region. The gate is coupled to the other source/drain region (floating diffusion FD2) of the reset transistor TR2rst. Further, the one source/drain region configuring the amplifying transistor TR2amp shares a region with the one source/drain region configuring the reset transistor TR2rst, and is coupled to the power supply VDD.

The selection transistor TR2sel includes a gate, a channel formation region, and a source/drain region. The gate is coupled to the select line SEL2. Further, one source/drain region configuring the selection transistor TR2sel shares a region with the other source/drain region configuring the amplifying transistor TR2amp. The other source/drain region of the selection transistor TR2sel is coupled to a signal line (data output line) VSL2.

The reset transistor TR3rst includes a gate, a channel formation region, and a source/drain region. The gate of the reset transistor TR3rst is coupled to the reset line RST3, and one source/drain region configuring the reset transistor TR3rst is coupled to the power supply VDD. The other source/drain region configuring the reset transistor TR3rst also serves as the floating diffusion FD3.

The amplifying transistor TR3amp includes a gate, a channel formation region, and a source/drain region. The gate is coupled to the other source/drain region (floating diffusion FD3) configuring the reset transistor TR3rst. Further, one source/drain region configuring the amplifying transistor TR3amp shares a region with one source/drain region configuring the reset transistor TR3rst, and is coupled to the power supply VDD.

The selection transistor TR3sel includes a gate, a channel formation region, and a source/drain region. The gate is coupled to the select line SEL3. Further, one source/drain region configuring the selection transistor TR3sel shares a region with the other source/drain region configuring the amplifying transistor TR3amp. The other source/drain region of the selection transistor TR3sel is coupled to a signal line (data output line) VSL3.

The reset lines RST1, RST2, and RST3, the select lines SEL1, SEL2, and SEL3, and the transfer gate lines TG2 and TG3 are coupled to a vertical drive circuit 112 that configures a drive circuit. The signal lines (data output lines) VSL1, VSL2, and VSL3 are coupled to a column signal processing circuit 113 that configures a drive circuit.

The lower first contact 45, the lower second contact 46, and the upper first contact 27A, and the upper second contact 27B each include, for example, a doped silicon material such as PDAS (Phosphorus Doped Amorphous Silicon), or a metal material such as aluminum (Al), tungsten (W), titanium (Ti), cobalt (Co), hafnium (Hf), or tantalum (Ta).

(2-2. Method of Manufacturing Photoelectric Conversion Device)

It is possible to manufacture the photoelectric conversion device 10B of the present embodiment, for example, in the following manner.

FIG. 12 to FIG. 17 illustrate the method of manufacturing the photoelectric conversion device 10B in order of process. First, as illustrated in FIG. 12, for example, the p-well 31, is formed as a well of a first conductivity type in the semiconductor substrate 30 and the inorganic photoelectric conversion sections 32B and 32R of the second conductivity type (for example, n-type) are formed in this p-well 31. A p+ region is formed in the vicinity of the first surface 30A of the semiconductor substrate 30.

As also illustrated in FIG. 12, n+regions to serve as the floating diffusions FD1 to FD3 are formed on the second surface 30B of the semiconductor substrate 30, for example. Thereafter, a gate insulating layer 33 and a gate wiring layer 47 are formed. The gate wiring layer 47 includes gates of the transfer transistor Tr2, the transfer transistor Tr3, the selection transistor SEL, the amplifying transistor AMP, and the reset transistor RST. Thereby, the transfer transistor Tr2, the transfer transistor Tr3, the selection transistor SEL, the amplifying transistor AMP, and the reset transistor RST are formed. Further, the lower first contact 45, the lower second contact 46, and the multilayer wiring 40 are formed on the second surface 30B of the semiconductor substrate 30. The multilayer wiring 40 includes the insulating layer 44 and the wiring layers 41 to 43 including the coupling portion 41A.

As a base of the semiconductor substrate 30, for example, an SOI (Silicon on Insulator) substrate is used in which the semiconductor substrate 30, an embedded oxide film (not illustrated), and a holding substrate (not illustrated) are stacked. Although not illustrated in FIG. 12, the embedded oxide film and the holding substrate are joined to the first surface 30A of the semiconductor substrate 30. After ion implantation, an annealing process is performed.

Thereafter, a support substrate (not illustrated), another semiconductor substrate, or the like is joined to the second surface 30B side (the multilayer wiring 40 side) of the semiconductor substrate 30 and flipped vertically. Subsequently, the semiconductor substrate 30 is separated from the embedded oxide film and the holding substrate of the SOI substrate to cause the first surface 30A of the semiconductor substrate 30 to be exposed. It is possible to perform the aforementioned processes with a technique used in a usual CMOS process such as ion implantation or CVD Chemical Vapor Deposition).

Thereafter, as illustrated in FIG. 13, the semiconductor substrate 30 is processed from the first surface 30A side, for example, by dry etching to form an annular opening 53H. The opening 53H has a depth penetrating from the first surface 30A to the second surface 30B of the semiconductor substrate 30 as illustrated in FIG. 13, and reaching the coupling portion 41A, for example.

Subsequently, for example, a negative fixed charge layer 51 is formed on the first surface 30A of the semiconductor substrate 30 and a side surface of the opening 53H. Two or more types of films may be stacked as the negative fixed charge layer 51. This makes it possible to further improve the function as the hole storage layer. The dielectric layer 52 is formed after the negative fixed charge layer 51 is formed. Next, after pad portions 39A and 39B are formed at predetermined positions on the dielectric layer 52, the interlayer insulating layer 26 is formed on the dielectric layer 52 and the pad portions 39A and 39B, and the surface of the interlayer insulating layer 26 is planarized by, for example, a CMP (Chemical Mechanical Polishing) method.

Subsequently, as illustrated in FIG. 14, openings 26H1 and 26H2 penetrating to the pad portions 39A and 39B are formed in the interlayer insulating layer 26. Next, a conductive material such as Al is buried in the openings 26H1 and 26H2 to form the upper first contact 27A and the upper second contact 27B, respectively, for example. Subsequently, as illustrated in FIG. 15, after the conductive layer 21x is formed on the interlayer insulating layer 26, a photoresist PR is deposited at a predetermined position of the conductive layer 21x (for example, between the pad portion 39A and the pad portion 39B). Thereafter, the read electrode 21A and the storage electrode 21B illustrated in FIG. 16 are patterned by etching and removing the photoresist PR.

Next, as illustrated in FIG. 17, after the insulating layer 22 is formed on the interlayer insulating layer 26, the read electrode 21A, and the storage electrode 21B, the opening 22H is provided on the read electrode 21A. Thereafter, the charge storage layer 23, the photoelectric conversion layer 24, the upper electrode 25, the protective layer 18, and the light shielding film 28 are formed on the insulating layer 22. It is to be noted that, as described above, in a case where another organic layer is formed in an upper layer or a lower layer of the photoelectric conversion layer 24, it is desirable to form it continuously (by a vacuum consistent process) in the vacuum process. Further, the method of depositing the photoelectric conversion layer 24 is not necessarily limited to a method using a vacuum evaporation method, and another method, for example, a spin coating technique, a printing technique, or the like may be used. Finally, an optical member such as a planarization layer and the on-chip lens layer 19 are provided. Thereby, the photoelectric conversion device 10B illustrated in FIG. 9 is completed.

In the photoelectric conversion device 10B, when light enters the organic photoelectric conversion section 20 via the on-chip lens19L, the light passes through the organic photoelectric conversion section 20, the inorganic photoelectric conversion sections 32B and 32R in this order, and is subjected to photoelectric conversion for each of green, blue, and red color light in the passing process, as in the photoelectric conversion device 10A of the first embodiment described above.

FIG. 18 illustrates an operation example of the photoelectric conversion device 10B. (A) illustrates a potential at the storage electrode 21B, (B) illustrates a potential at the floating diffusion FD1 (read electrode 21A), and (C) illustrates a potential at the gate (Gsel) of the reset transistor TR1rst. In the photoelectric conversion device 10B, voltages are individually applied to the read electrode 21A and the storage electrode 21B.

In the photoelectric conversion device 10B, in the storage period, a potential V1 is applied to the read electrode 21A from the drive circuit, and a potential V2 is applied to the storage electrode 21B. Here, it is assumed that the potentials V1 and V2 satisfy V2>V1. As a result, charges (here, electrons) generated by photoelectric conversion are attracted to the storage electrode 21B and stored in the region of the photoelectric conversion layer 24 opposed to the storage electrode 21B (storage period). Incidentally, a potential of the region of the photoelectric conversion layer 24 opposed to the storage electrode 21B becomes a value that is more negative with the passage of time of photoelectric conversion. It is to be noted that the electrons are transmitted from the upper electrode 25 to the drive circuit.

In the photoelectric conversion device 10B, a resetting operation is performed at a later stage of the storage period. Specifically, at a timing t1, the scanning unit varies the voltage of the reset signal RST from a low level to a high level. Accordingly, in the unit pixel P, the reset transistor TR1rst is turned on. As a result, the voltage of the floating diffusion FD1 is set to the power supply voltage VDD, and the voltage of the floating diffusion FD1 is reset (reset period).

After the reset operation is completed, the charge is read out. Specifically, at a timing t2, a potential V3 is applied to the read electrode 21A from the drive circuit, and a potential V4 is applied to the storage electrode 21B. Here, the potentials V3 and V4 satisfy V3<V4. As a result, the charges (here, electrons) stored in the region corresponding to the storage electrode 21B are read out from the read electrode 21A to the floating diffusion FD1. That is, the charges stored in the photoelectric conversion layer 24 are read out to the control unit (transfer period).

After the read operation is completed, the potential V1 is applied from the drive circuit to the read electrode 21A, and the potential V2 is applied to the storage electrode 21B. As a result, charges (here, electrons) generated by photoelectric conversion are attracted to the storage electrode 21B and stored in the region of the photoelectric conversion layer 24 opposed to the storage electrode 21B (storage period).

(2-3. Workings and Effects)

As described above, in the photoelectric conversion device 10B of the present embodiment, the photoelectric conversion layer 124 is formed using the organic semiconductor material that allows variation in the ratio between the horizontally-oriented crystal and the vertically-oriented crystal in the layer to be three times or less between the case where film formation is performed at the first temperature and the case where the film formation is performed at the second temperature higher than the first temperature, or using the organic semiconductor material that allows the variation amount of the angle formed with the electrode surface of the lower electrode 21 to be smaller than 10° between the foregoing cases. This reduces the formation of a defect at the grain boundary of the bulk heterostructure configuring the photoelectric conversion layer 24 and enables improvement in quantum efficiency and responsiveness.

In addition, in the photoelectric conversion device 10B of the present embodiment, by using, as the one organic semiconductor material, for example, the above-described material that allows the variation amount of the orientation angle to be smaller than 10° between the case where film formation is performed at the first temperature and the case where the film formation is performed at the second temperature higher than the first temperature and also allows the orientation angle range to be smaller than 46° between the case where film formation is performed at the first temperature and the case where the film formation is performed at the second temperature higher than the first temperature, it is possible to further improve the response speed. In addition, robustness (durability) to the film formation temperature of the photoelectric conversion layer 24 can be improved.

3. APPLICATION EXAMPLES

Application Example 1

FIG. 19 illustrates, for example, an overall configuration of the imaging apparatus 1 in which the photoelectric conversion device 10A (or the photoelectric conversion device 10B) described in the embodiment described above is used for each pixel. This imaging apparatus 1 is a CMOS image sensor. The imaging apparatus 1 includes a pixel unit 1*a* as an imaging region on the semiconductor substrate 11. The imaging apparatus 1 also includes a peripheral circuit unit 130 in a surrounding region of the pixel unit 1*a*. The peripheral circuit unit 130 includes, for example, a row scanning unit 131, a horizontal selecting unit 133, a column scanning unit 134, and a system control unit 132.

The pixel unit 1*a* includes a plurality of unit pixels P (corresponding to the photoelectric conversion section 10, for example) two-dimensionally disposed in matrix, for example. In the unit pixel P, a pixel drive line Lread (specifically, a row select line and a reset control line) is wired for each pixel row, and a vertical signal line Lsig is wired for each pixel column, for example. The pixel drive line Lread is directed to transmitting a drive signal for reading a signal from a pixel. One end of the pixel drive line Lread is coupled to an output end of the row scanning unit 131 corresponding to each row.

The row scanning unit 131 includes a shift register, an address recorder, and the like, and is a pixel drive unit that drives the respective unit pixels P of the pixel unit 1*a* on a row basis, for example. A signal outputted from each unit pixel P of the pixel row selected and scanned by the row scanning unit 131 is supplied to the horizontal selecting unit 133 through each of the vertical signal lines Lsig. The horizontal selecting unit 133 includes an amplifier, a horizontal selection switch, and the like provided for each vertical signal line Lsig.

The column scanning unit 134 includes a shift register, an address decoder, and the like, and drives the respective horizontal selection switches of the horizontal selecting unit 133 in order while scanning the respective horizontal selection switches of the horizontal selecting unit 133. By selective scanning by this column scanning unit 134, signals of the respective pixels transmitted through the respective vertical signal lines Lsig are outputted to a horizontal signal line 135 in order, and are transmitted to outside of the semiconductor substrate 11 through the horizontal signal line 135.

A circuit portion including the row scanning unit 131, the horizontal selecting unit 133, the column scanning unit 134, and the horizontal signal line 135 may be formed directly on the semiconductor substrate 11 or may be disposed on an external control IC. In addition, those circuit portions may be formed on another substrate coupled by a cable or the like.

The system control unit 132 receives a clock supplied from outside of the semiconductor substrate 11, data instructing an operation mode, and the like, and outputs data such as inside information of the imaging apparatus 1. The system control unit 132 further includes a timing generator that generates various timing signals, and controls the driving of the peripheral circuit such as the row scanning unit 131, the horizontal selecting unit 133, the column scanning unit 134, and the like on the basis of various timing signals generated by the timing generator.

Application Example 2

The aforementioned imaging apparatus 1 is applicable to any type of electronic apparatuses with an imaging function including, for example, a camera system such as a digital still camera or a video camera, a mobile phone having the imaging function, and the like. FIG. 20 illustrates an outline configuration of a camera 2 as an example thereof. The camera 2 is, for example, a video camera capable of capturing a still image or a moving image. The camera 2 includes the imaging apparatus 1, an optical system (optical lens) 310, a shutter device 311, a driving unit 313 driving the imaging apparatus 1 and the shutter device 311, and a signal processing unit 312.

The optical system 310 guides image light (entering light) from a subject to the pixel unit 1*a* of the imaging apparatus 1. This optical system 310 may include a plurality of optical lenses. The shutter device 311 controls a light application period and a light shielding period of the imaging apparatus 1. The driving unit 313 controls a transferring operation of the imaging apparatus 1 and a shutter operation of the shutter device 311. The signal processing unit 312 performs various signal processes on the signal outputted from the imaging apparatus 1. An image signal Dout after the signal process is stored in a storage medium such as a memory or outputted to a monitor or the like.

Application Example 3

<Example of Application to In-Vivo Information Acquisition System>

Furthermore, the technology (the present technology) according to the present disclosure can be applied to various products. For example, the technology according to the present disclosure may be applied to an endoscopic surgery system.

FIG. 21 is a block diagram depicting an example of a schematic configuration of an in-vivo information acquisition system of a patient using a capsule type endoscope, to which the technology according to an embodiment of the present disclosure (present technology) can be applied.

The in-vivo information acquisition system 10001 includes a capsule type endoscope 10100 and an external controlling apparatus 10200.

The capsule type endoscope 10100 is swallowed by a patient at the time of inspection. The capsule type endoscope 10100 has an image pickup function and a wireless communication function and successively picks up an image of the inside of an organ such as the stomach or an intestine (hereinafter referred to as in-vivo image) at predetermined intervals while it moves inside of the organ by peristaltic motion for a period of time until it is naturally discharged from the patient. Then, the capsule type endoscope 10100 successively transmits information of the in-vivo image to the external controlling apparatus 10200 outside the body by wireless transmission.

The external controlling apparatus 10200 integrally controls operation of the in-vivo information acquisition system 10001. Further, the external controlling apparatus 10200 receives information of an in-vivo image transmitted thereto from the capsule type endoscope 10100 and generates image data for displaying the in-vivo image on a display apparatus (not depicted) on the basis of the received information of the in-vivo image.

In the in-vivo information acquisition system 10001, an in-vivo image imaged a state of the inside of the body of a patient can be acquired at any time in this manner for a period of time until the capsule type endoscope 10100 is discharged after it is swallowed.

A configuration and functions of the capsule type endoscope 10100 and the external controlling apparatus 10200 are described in more detail below.

The capsule type endoscope 10100 includes a housing 10101 of the capsule type, in which a light source unit 10111, an image pickup unit 10112, an image processing unit 10113, a wireless communication unit 10114, a power feeding unit 10115, a power supply unit 10116 and a control unit 10117 are accommodated.

The light source unit 10111 includes a light source such as, for example, a light emitting diode (LED) and irradiates light on an image pickup field-of-view of the image pickup unit 10112.

The image pickup unit 10112 includes an image pickup element and an optical system including a plurality of lenses provided at a preceding stage to the image pickup element. Reflected light (hereinafter referred to as observation light) of light irradiated on a body tissue which is an observation target is condensed by the optical system and introduced into the image pickup element. In the image pickup unit 10112, the incident observation light is photoelectrically converted by the image pickup element, by which an image signal corresponding to the observation light is generated. The image signal generated by the image pickup unit 10112 is provided to the image processing unit 10113.

The image processing unit 10113 includes a processor such as a central processing unit (CPU) or a graphics processing unit (GPU) and performs various signal processes for an image signal generated by the image pickup unit 10112. The image processing unit 10113 provides the image signal for which the signal processes have been performed thereby as RAW data to the wireless communication unit 10114.

The wireless communication unit 10114 performs a predetermined process such as a modulation process for the image signal for which the signal processes have been performed by the image processing unit 10113 and transmits the resulting image signal to the external controlling apparatus 10200 through an antenna 10114A. Further, the wireless communication unit 10114 receives a control signal relating to driving control of the capsule type endoscope 10100 from the external controlling apparatus 10200 through the antenna 10114A. The wireless communication unit 10114 provides the control signal received from the external controlling apparatus 10200 to the control unit 10117.

The power feeding unit 10115 includes an antenna coil for power reception, a power regeneration circuit for regenerating electric power from current generated in the antenna coil, a voltage booster circuit and so forth. The power feeding unit 10115 generates electric power using the principle of non-contact charging.

The power supply unit 10116 includes a secondary battery and stores electric power generated by the power feeding unit 10115. In FIG. 21, in order to avoid complicated illustration, an arrow mark indicative of a supply destination of electric power from the power supply unit 10116 and so forth are omitted. However, electric power stored in the power supply unit 10116 is supplied to and can be used to drive the light source unit 10111, the image pickup unit 10112, the image processing unit 10113, the wireless communication unit 10114 and the control unit 10117.

The control unit 10117 includes a processor such as a CPU and suitably controls driving of the light source unit 10111, the image pickup unit 10112, the image processing unit 10113, the wireless communication unit 10114 and the power feeding unit 10115 in accordance with a control signal transmitted thereto from the external controlling apparatus 10200.

The external controlling apparatus 10200 includes a processor such as a CPU or a GPU, a microcomputer, a control board or the like in which a processor and a storage element such as a memory are mixedly incorporated. The external controlling apparatus 10200 transmits a control signal to the control unit 10117 of the capsule type endoscope 10100 through an antenna 10200A to control operation of the capsule type endoscope 10100. In the capsule type endoscope 10100, an irradiation condition of light upon an observation target of the light source unit 10111 can be changed, for example, in accordance with a control signal from the external controlling apparatus 10200. Further, an image pickup condition (for example, a frame rate, an exposure value or the like of the image pickup unit 10112) can be changed in accordance with a control signal from the external controlling apparatus 10200. Further, the substance of processing by the image processing unit 10113 or a condition for transmitting an image signal from the wireless communication unit 10114 (for example, a transmission interval, a transmission image number or the like) may be changed in accordance with a control signal from the external controlling apparatus 10200.

Further, the external controlling apparatus 10200 performs various image processes for an image signal transmitted thereto from the capsule type endoscope 10100 to generate image data for displaying a picked up in-vivo image on the display apparatus. As the image processes, various signal processes can be performed such as, for example, a development process (demosaic process), an image quality improving process (bandwidth enhancement process, a super-resolution process, a noise reduction (NR) process and/or image stabilization process) and/or an enlargement process (electronic zooming process). The external controlling apparatus 10200 controls driving of the display apparatus to cause the display apparatus to display a picked up in-vivo image on the basis of generated image data. Alternatively, the external controlling apparatus 10200 may also control a recording apparatus (not depicted) to record generated image data or control a printing apparatus (not depicted) to output generated image data by printing.

Description has been given above of an example of an in-vivo information acquisition system to which the technology of the present disclosure is applicable. The technology according to the present disclosure is applicable, for example, to the image pickup unit 10112 of the above-described configuration. This improves detection accuracy.

Application Example 4

<4. Example of Application to Endoscopic Surgery System>

The technology (the present technology) according to the present disclosure is applicable to various products. For example, the technology according to the present disclosure may be applied to an endoscopic surgery system.

FIG. 22 is a view depicting an example of a schematic configuration of an endoscopic surgery system to which the technology according to an embodiment of the present disclosure (present technology) can be applied.

In FIG. 22, a state is illustrated in which a surgeon (medical doctor) 11131 is using an endoscopic surgery system 11000 to perform surgery for a patient 11132 on a patient bed 11133. As depicted, the endoscopic surgery system 11000 includes an endoscope 11100, other surgical tools 11110 such as a pneumoperitoneum tube 11111 and an energy device 11112, a supporting arm apparatus 11120 which supports the endoscope 11100 thereon, and a cart 11200 on which various apparatus for endoscopic surgery are mounted.

The endoscope 11100 includes a lens barrel 11101 having a region of a predetermined length from a distal end thereof to be inserted into a body cavity of the patient 11132, and a camera head 11102 connected to a proximal end of the lens barrel 11101. In the example depicted, the endoscope 11100 is depicted which includes as a rigid endoscope having the lens barrel 11101 of the hard type. However, the endoscope 11100 may otherwise be included as a flexible endoscope having the lens barrel 11101 of the flexible type.

The lens barrel 11101 has, at a distal end thereof, an opening in which an objective lens is fitted. A light source apparatus 11203 is connected to the endoscope 11100 such that light generated by the light source apparatus 11203 is introduced to a distal end of the lens barrel 11101 by a light guide extending in the inside of the lens barrel 11101 and is irradiated toward an observation target in a body cavity of the patient 11132 through the objective lens. It is to be noted that the endoscope 11100 may be a forward-viewing endoscope or may be an oblique-viewing endoscope or a side-viewing endoscope.

An optical system and an image pickup element are provided in the inside of the camera head 11102 such that reflected light (observation light) from the observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 11201.

The CCU 11201 includes a central processing unit (CPU), a graphics processing unit (GPU) or the like and integrally controls operation of the endoscope 11100 and a display apparatus 11202. Further, the CCU 11201 receives an image signal from the camera head 11102 and performs, for the image signal, various image processes for displaying an image based on the image signal such as, for example, a development process (demosaic process).

The display apparatus 11202 displays thereon an image based on an image signal, for which the image processes have been performed by the CCU 11201, under the control of the CCU 11201.

The light source apparatus 11203 includes a light source such as, for example, a light emitting diode (LED) and supplies irradiation light upon imaging of a surgical region to the endoscope 11100.

An inputting apparatus 11204 is an input interface for the endoscopic surgery system 11000. A user can perform inputting of various kinds of information or instruction inputting to the endoscopic surgery system 11000 through the inputting apparatus 11204. For example, the user would input an instruction or a like to change an image pickup condition (type of irradiation light, magnification, focal distance or the like) by the endoscope 11100.

A treatment tool controlling apparatus 11205 controls driving of the energy device 11112 for cautery or incision of a tissue, sealing of a blood vessel or the like. A pneumoperitoneum apparatus 11206 feeds gas into a body cavity of the patient 11132 through the pneumoperitoneum tube 11111 to inflate the body cavity in order to secure the field of view of the endoscope 11100 and secure the working space for the surgeon. A recorder 11207 is an apparatus capable of recording various kinds of information relating to surgery. A printer 11208 is an apparatus capable of printing various kinds of information relating to surgery in various forms such as a text, an image or a graph.

It is to be noted that the light source apparatus 11203 which supplies irradiation light when a surgical region is to be imaged to the endoscope 11100 may include a white light source which includes, for example, an LED, a laser light source or a combination of them. Where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 11203. Further, in this case, if laser beams from the respective RGB laser light sources are irradiated time-divisionally on an observation target and driving of the image pickup elements of the camera head 11102 are controlled in synchronism with the irradiation timings. Then images individually corresponding to the R, G and B colors can be also picked up time-divisionally. According to this method, a color image can be obtained even if color filters are not provided for the image pickup element.

Further, the light source apparatus 11203 may be controlled such that the intensity of light to be outputted is changed for each predetermined time. By controlling driving of the image pickup element of the camera head 11102 in synchronism with the timing of the change of the intensity of light to acquire images time-divisionally and synthesizing the images, an image of a high dynamic range free from underexposed blocked up shadows and overexposed highlights can be created.

Further, the light source apparatus 11203 may be configured to supply light of a predetermined wavelength band ready for special light observation. In special light observation, for example, by utilizing the wavelength dependency of absorption of light in a body tissue to irradiate light of a narrow band in comparison with irradiation light upon ordinary observation (namely, white light), narrow band observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 11203 can be configured to supply such narrow-band light and/or excitation light suitable for special light observation as described above.

FIG. 23 is a block diagram depicting an example of a functional configuration of the camera head 11102 and the CCU 11201 depicted in FIG. 22.

The camera head 11102 includes a lens unit 11401, an image pickup unit 11402, a driving unit 11403, a communication unit 11404 and a camera head controlling unit 11405. The CCU 11201 includes a communication unit 11411, an image processing unit 11412 and a control unit 11413. The camera head 11102 and the CCU 11201 are connected for communication to each other by a transmission cable 11400.

The lens unit 11401 is an optical system, provided at a connecting location to the lens barrel 11101. Observation light taken in from a distal end of the lens barrel 11101 is guided to the camera head 11102 and introduced into the lens unit 11401. The lens unit 11401 includes a combination of a plurality of lenses including a zoom lens and a focusing lens.

The number of image pickup elements which is included by the image pickup unit 11402 may be one (single-plate type) or a plural number (multi-plate type). Where the image pickup unit 11402 is configured as that of the multi-plate type, for example, image signals corresponding to respective R, G and B are generated by the image pickup elements, and the image signals may be synthesized to obtain a color image. The image pickup unit 11402 may also be configured so as to have a pair of image pickup elements for acquiring respective image signals for the right eye and the left eye ready for three dimensional (3D) display. If 3D display is performed, then the depth of a living body tissue in a surgical region can be comprehended more accurately by the surgeon 11131. It is to be noted that, where the image pickup unit 11402 is configured as that of stereoscopic type, a plurality of systems of lens units 11401 are provided corresponding to the individual image pickup elements.

Further, the image pickup unit 11402 may not necessarily be provided on the camera head 11102. For example, the image pickup unit 11402 may be provided immediately behind the objective lens in the inside of the lens barrel 11101.

The driving unit 11403 includes an actuator and moves the zoom lens and the focusing lens of the lens unit 11401 by a predetermined distance along an optical axis under the control of the camera head controlling unit 11405. Consequently, the magnification and the focal point of a picked up image by the image pickup unit 11402 can be adjusted suitably.

The communication unit 11404 includes a communication apparatus for transmitting and receiving various kinds of information to and from the CCU 11201. The communication unit 11404 transmits an image signal acquired from the image pickup unit 11402 as RAW data to the CCU 11201 through the transmission cable 11400.

In addition, the communication unit 11404 receives a control signal for controlling driving of the camera head 11102 from the CCU 11201 and supplies the control signal to the camera head controlling unit 11405. The control signal includes information relating to image pickup conditions such as, for example, information that a frame rate of a picked up image is designated, information that an exposure value upon image picking up is designated and/or information that a magnification and a focal point of a picked up image are designated.

It is to be noted that the image pickup conditions such as the frame rate, exposure value, magnification or focal point may be designated by the user or may be set automatically by the control unit 11413 of the CCU 11201 on the basis of an acquired image signal. In the latter case, an auto exposure (AE) function, an auto focus (AF) function and an auto white balance (AWB) function are incorporated in the endoscope 11100.

The camera head controlling unit 11405 controls driving of the camera head 11102 on the basis of a control signal from the CCU 11201 received through the communication unit 11404.

The communication unit 11411 includes a communication apparatus for transmitting and receiving various kinds of information to and from the camera head 11102. The communication unit 11411 receives an image signal transmitted thereto from the camera head 11102 through the transmission cable 11400.

Further, the communication unit 11411 transmits a control signal for controlling driving of the camera head 11102 to the camera head 11102. The image signal and the control signal can be transmitted by electrical communication, optical communication or the like.

The image processing unit 11412 performs various image processes for an image signal in the form of RAW data transmitted thereto from the camera head 11102.

The control unit 11413 performs various kinds of control relating to image picking up of a surgical region or the like by the endoscope 11100 and display of a picked up image obtained by image picking up of the surgical region or the like. For example, the control unit 11413 creates a control signal for controlling driving of the camera head 11102.

Further, the control unit 11413 controls, on the basis of an image signal for which image processes have been performed by the image processing unit 11412, the display apparatus 11202 to display a picked up image in which the surgical region or the like is imaged. Thereupon, the control unit 11413 may recognize various objects in the picked up image using various image recognition technologies. For example, the control unit 11413 can recognize a surgical tool such as forceps, a particular living body region, bleeding, mist when the energy device 11112 is used and so forth by detecting the shape, color and so forth of edges of objects included in a picked up image. The control unit 11413 may cause, when it controls the display apparatus 11202 to display a picked up image, various kinds of surgery supporting information to be displayed in an overlapping manner with an image of the surgical region using a result of the recognition. Where surgery supporting information is displayed in an overlapping manner and presented to the surgeon 11131, the burden on the surgeon 11131 can be reduced and the surgeon 11131 can proceed with the surgery with certainty.

The transmission cable 11400 which connects the camera head 11102 and the CCU 11201 to each other is an electric signal cable ready for communication of an electric signal, an optical fiber ready for optical communication or a composite cable ready for both of electrical and optical communications.

Here, while, in the example depicted, communication is performed by wired communication using the transmission cable 11400, the communication between the camera head 11102 and the CCU 11201 may be performed by wireless communication.

Description has been given above of an example of an endoscopic surgery system to which the technology according to the present disclosure is applicable. The technology according to the present disclosure is applicable, for example, to the image pickup unit 11402 of the above-described configuration. By applying the technology according to the present disclosure to the image pickup unit 11402, detection accuracy is improved.

It is to be noted that, here, description has been given of an endoscopic surgery system as an example; however, the technology according to the present disclosure may be applied to a micrographic surgery system or the like other than the above.

Application Example 5

<Example of Application to Mobile Body>

The technology according to the present disclosure is applicable to various products. For example, the technology according to the present disclosure may be implemented as an apparatus mounted on any type of movable body such as an automobile, an electric vehicle, a hybrid electric vehicle, a motorcycle, a bicycle, a personal mobility, an airplane, a drone, a vessel, a robot, a construction machine, an agricultural machine (tractor), etc.

FIG. 24 is a block diagram depicting an example of schematic configuration of a vehicle control system as an example of a mobile body control system to which the technology according to an embodiment of the present disclosure can be applied.

The vehicle control system 12000 includes a plurality of electronic control units connected to each other via a communication network 12001. In the example depicted in FIG. 24, the vehicle control system 12000 includes a driving system control unit 12010, a body system control unit 12020, an outside-vehicle information detecting unit 12030, an in-vehicle information detecting unit 12040, and an integrated control unit 12050. In addition, a microcomputer 12051, a sound/image output section 12052, and a vehicle-mounted network interface (I/F) 12053 are illustrated as a functional configuration of the integrated control unit 12050.

The driving system control unit 12010 controls the operation of devices related to the driving system of the vehicle in accordance with various kinds of programs. For example, the driving system control unit 12010 functions as a control device for a driving force generating device for generating the driving force of the vehicle, such as an internal combustion engine, a driving motor, or the like, a driving force transmitting mechanism for transmitting the driving force to wheels, a steering mechanism for adjusting the steering angle of the vehicle, a braking device for generating the braking force of the vehicle, and the like.

The body system control unit 12020 controls the operation of various kinds of devices provided to a vehicle body in accordance with various kinds of programs. For example, the body system control unit 12020 functions as a control device for a keyless entry system, a smart key system, a power window device, or various kinds of lamps such as a headlamp, a backup lamp, a brake lamp, a turn signal, a fog lamp, or the like. In this case, radio waves transmitted from a mobile device as an alternative to a key or signals of various kinds of switches can be input to the body system control unit 12020. The body system control unit 12020 receives these input radio waves or signals, and controls a door lock device, the power window device, the lamps, or the like of the vehicle.

The outside-vehicle information detecting unit 12030 detects information about the outside of the vehicle including the vehicle control system 12000. For example, the outside-vehicle information detecting unit 12030 is connected with an imaging section 12031. The outside-vehicle information detecting unit 12030 makes the imaging section 12031 image an image of the outside of the vehicle, and receives the imaged image. On the basis of the received image, the outside-vehicle information detecting unit 12030 may perform processing of detecting an object such as a human, a vehicle, an obstacle, a sign, a character on a road surface, or the like, or processing of detecting a distance thereto.

The imaging section 12031 is an optical sensor that receives light, and which outputs an electric signal corresponding to a received light amount of the light. The imaging section 12031 can output the electric signal as an image, or can output the electric signal as information about a measured distance. In addition, the light received by the imaging section 12031 may be visible light, or may be invisible light such as infrared rays or the like.

The in-vehicle information detecting unit 12040 detects information about the inside of the vehicle. The in-vehicle information detecting unit 12040 is, for example, connected with a driver state detecting section 12041 that detects the state of a driver. The driver state detecting section 12041, for example, includes a camera that images the driver. On the basis of detection information input from the driver state detecting section 12041, the in-vehicle information detecting unit 12040 may calculate a degree of fatigue of the driver or a degree of concentration of the driver, or may determine whether the driver is dozing.

The microcomputer 12051 can calculate a control target value for the driving force generating device, the steering mechanism, or the braking device on the basis of the information about the inside or outside of the vehicle which information is obtained by the outside-vehicle information detecting unit 12030 or the in-vehicle information detecting unit 12040, and output a control command to the driving system control unit 12010. For example, the microcomputer 12051 can perform cooperative control intended to implement functions of an advanced driver assistance system (ADAS) which functions include collision avoidance or shock mitigation for the vehicle, following driving based on a following distance, vehicle speed maintaining driving, a warning of collision of the vehicle, a warning of deviation of the vehicle from a lane, or the like.

In addition, the microcomputer 12051 can perform cooperative control intended for automatic driving, which makes the vehicle to travel autonomously without depending on the operation of the driver, or the like, by controlling the driving force generating device, the steering mechanism, the braking device, or the like on the basis of the information about the outside or inside of the vehicle which information is obtained by the outside-vehicle information detecting unit 12030 or the in-vehicle information detecting unit 12040.

In addition, the microcomputer 12051 can output a control command to the body system control unit 12020 on the basis of the information about the outside of the vehicle which information is obtained by the outside-vehicle information detecting unit 12030. For example, the microcomputer 12051 can perform cooperative control intended to prevent a glare by controlling the headlamp so as to change from a high beam to a low beam, for example, in accordance with the position of a preceding vehicle or an oncoming vehicle detected by the outside-vehicle information detecting unit 12030.

The sound/image output section 12052 transmits an output signal of at least one of a sound and an image to an output device capable of visually or auditorily notifying information to an occupant of the vehicle or the outside of the vehicle. In the example of FIG. 24, an audio speaker 12061, a display section 12062, and an instrument panel 12063 are illustrated as the output device. The display section 12062 may, for example, include at least one of an on-board display and a head-up display.

FIG. 25 is a diagram depicting an example of the installation position of the imaging section 12031.

In FIG. 25, the imaging section 12031 includes imaging sections 12101, 12102, 12103, 12104, and 12105.

The imaging sections 12101, 12102, 12103, 12104, and 12105 are, for example, disposed at positions on a front nose, sideview mirrors, a rear bumper, and a back door of the vehicle 12100 as well as a position on an upper portion of a windshield within the interior of the vehicle. The imaging section 12101 provided to the front nose and the imaging section 12105 provided to the upper portion of the windshield within the interior of the vehicle obtain mainly an image of the front of the vehicle 12100. The imaging sections 12102 and 12103 provided to the sideview mirrors obtain mainly an image of the sides of the vehicle 12100. The imaging section 12104 provided to the rear bumper or the back door obtains mainly an image of the rear of the vehicle 12100. The imaging section 12105 provided to the upper portion of the windshield within the interior of the vehicle is used mainly to detect a preceding vehicle, a pedestrian, an obstacle, a signal, a traffic sign, a lane, or the like.

Incidentally, FIG. 25 depicts an example of photographing ranges of the imaging sections 12101 to 12104. An imaging range 12111 represents the imaging range of the imaging section 12101 provided to the front nose. Imaging ranges 12112 and 12113 respectively represent the imaging ranges of the imaging sections 12102 and 12103 provided to the sideview mirrors. An imaging range 12114 represents the imaging range of the imaging section 12104 provided to the rear bumper or the back door. A bird's-eye image of the vehicle 12100 as viewed from above is obtained by superimposing image data imaged by the imaging sections 12101 to 12104, for example.

At least one of the imaging sections 12101 to 12104 may have a function of obtaining distance information. For example, at least one of the imaging sections 12101 to 12104 may be a stereo camera constituted of a plurality of imaging elements, or may be an imaging element having pixels for phase difference detection.

For example, the microcomputer 12051 can determine a distance to each three-dimensional object within the imaging ranges 12111 to 12114 and a temporal change in the distance (relative speed with respect to the vehicle 12100) on the basis of the distance information obtained from the imaging sections 12101 to 12104, and thereby extract, as a preceding vehicle, a nearest three-dimensional object in particular that is present on a traveling path of the vehicle 12100 and which travels in substantially the same direction as the vehicle 12100 at a predetermined speed (for example, equal to or more than 0 km/hour). Further, the microcomputer 12051 can set a following distance to be maintained in front of a preceding vehicle in advance, and perform automatic brake control (including following stop control), automatic acceleration control (including following start control), or the like. It is thus possible to perform cooperative control intended for automatic driving that makes the vehicle travel autonomously without depending on the operation of the driver or the like.

For example, the microcomputer 12051 can classify three-dimensional object data on three-dimensional objects into three-dimensional object data of a two-wheeled vehicle, a standard-sized vehicle, a large-sized vehicle, a pedestrian, a utility pole, and other three-dimensional objects on the basis of the distance information obtained from the imaging sections 12101 to 12104, extract the classified three-dimensional object data, and use the extracted three-dimensional object data for automatic avoidance of an obstacle. For example, the microcomputer 12051 identifies obstacles around the vehicle 12100 as obstacles that the driver of the vehicle 12100 can recognize visually and obstacles that are difficult for the driver of the vehicle 12100 to recognize visually. Then, the microcomputer 12051 determines a collision risk indicating a risk of collision with each obstacle. In a situation in which the collision risk is equal to or higher than a set value and there is thus a possibility of collision, the microcomputer 12051 outputs a warning to the driver via the audio speaker 12061 or the display section 12062, and performs forced deceleration or avoidance steering via the driving system control unit 12010. The microcomputer 12051 can thereby assist in driving to avoid collision.

At least one of the imaging sections 12101 to 12104 may be an infrared camera that detects infrared rays. The microcomputer 12051 can, for example, recognize a pedestrian by determining whether or not there is a pedestrian in imaged images of the imaging sections 12101 to 12104. Such recognition of a pedestrian is, for example, performed by a procedure of extracting characteristic points in the imaged images of the imaging sections 12101 to 12104 as infrared cameras and a procedure of determining whether or not it is the pedestrian by performing pattern matching processing on a series of characteristic points representing the contour of the object. When the microcomputer 12051 determines that there is a pedestrian in the imaged images of the imaging sections 12101 to 12104, and thus recognizes the pedestrian, the sound/image output section 12052 controls the display section 12062 so that a square contour line for emphasis is displayed so as to be superimposed on the recognized pedestrian. The sound/image output section 12052 may also control the display section 12062 so that an icon or the like representing the pedestrian is displayed at a desired position.

4. Working Examples

Next, working examples of the present disclosure will be described in detail. In Experiment 1, the orientation of the organic semiconductor material was evaluated. In Experiment 2, a photoelectric conversion device was fabricated and its electric characteristics were evaluated.

[Experiment 1; Evaluation of Orientation]

First, a sample for 2D-GIXD evaluation was fabricated. After a glass substrate with an ITO electrode (lower electrode) having a thickness of 50 nm was cleaned by a UV/ozone process, a photoelectric conversion layer was deposited at a substrate temperature of 0° C. by a resistance heating method while rotating a substrate holder in vacuum of $1 \times 10^{-5}$ Pa or less. As a material of the photoelectric conversion layer, DTP-DTT represented by the above formula (1-2) as the one organic semiconductor material (hole transporting material), and a $F_6$-SubPc-$OC_6F_5$ represented by the following formula (18-1) and $C_{60}$ represented by the following formula (19-1) as the other organic semiconductor material were used, and these were simultaneously deposited. A ratio of a deposition speed was DTP-DTT: $F_6$-SubPc-$OC_6F_5$: $C_{60}$=2:2:1. Film formation was so performed that the total film thickness was 230 nm. Subsequently, B4PyMPM represented by the following formula (21) was deposited with a thickness of 5 nm by a vacuum evaporation method at a substrate temperature of 0° C. as a buffer layer on the photoelectric conversion layer. This was used as a sample (Sample 1) for 2D-GIXD evaluation.

[Chem. 9]

(18-1)

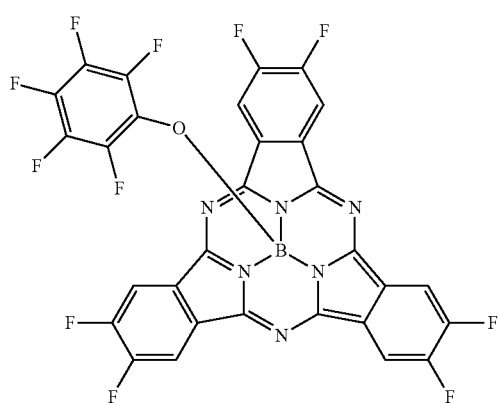

(19-1)

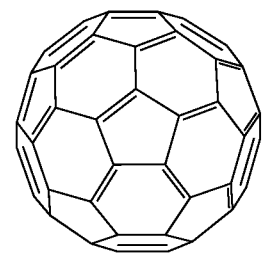

(21)

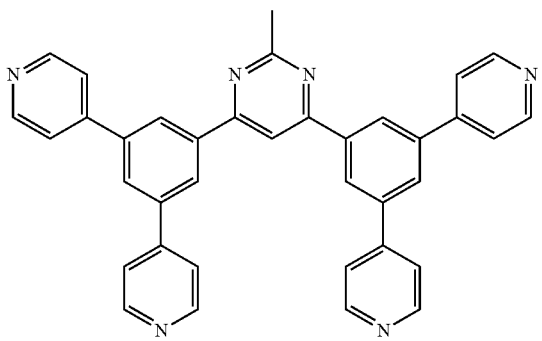

In addition, samples (Samples 1 and 2) for 2D-GIXD evaluation were fabricated using the DBP-DTT represented by the above formula (1-1) and the DP-DTT represented by the following formula (22), respectively, instead of DTP-DTT. Further, samples (Samples 4 to 6) for 2D-GIXD evaluation were fabricated with the film formation temperature of the photoelectric conversion layer being varied from the substrate temperature 0° C. to 25° C. Table 1 summarizes the hole transporting materials and film formation temperatures used in respective Samples 1 to 6.

[Chem. 10]

(22)

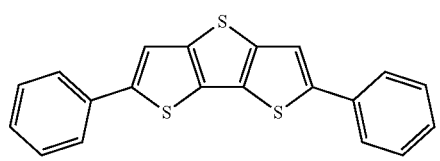

TABLE 1

| | Hole transporting material | Film formation temperature (° C.) |
|---|---|---|
| Sample 1 | Formula (1-2) | 0 |
| Sample 2 | Formula (1-1) | 0 |
| Sample 3 | Formula (21) | 0 |
| Sample 4 | Formula (1-2) | 25 |
| Sample 5 | Formula (1-1) | 25 |
| Sample 6 | Formula (21) | 25 |

The orientation of the photoelectric conversion layer using the above hole transporting material was evaluated by grazing incident X-ray diffraction method (Grazing Incident X-ray Diffraction; GIXD) using a two-dimensional detector with the use of BL46XU of SPring-8. FIG. 26 schematically illustrates a configuration of an evaluating apparatus (BL46XU). Table 2 summarizes measurement conditions.

TABLE 2

| Measurement conditions | |
|---|---|
| X-ray energy (wavelength) | 12.398 keV(1 Å) |
| Beam size | about 30 μm (vertical) × 200 μm (horizontal) |
| Camera length | about 175 mm |
| Exposure time | 1 second to 5 seconds |
| Angle of deviation | 0.12° |

First, a peak obtained by 2D-GIXD was divided into three components (a vertical orientation component, an oblique orientation component, and a horizontal orientation component), a background component was removed, and diffraction intensity was analyzed for each component. Thereafter, the ratio of each component was calculated, and an intensity ratio (vertical orientation component/horizontal orientation component) between the vertical orientation component and the horizontal orientation component was calculated, and this was defined as an index of orientation.

FIG. 27 illustrates a result of 2D-GIXD measurement of Sample 1. Using a direct beam position as an origin, it was divided in the azimuthal direction into three orientation components (the vertical orientation component (3° to 32°), the oblique orientation component (32° to 61°), and the horizontal orientation component (61° to 90°)). An intensity profile in a q-direction was obtained for each orientation component. FIG. 28 illustrates, as an example, the intensity profile of the horizontal orientation component of Sample 1. As the horizontal orientation component, the peak in the vicinity of 20 nm$^{-1}$ in FIG. 28 was analyzed. "q" on the horizontal axis was converted into θ from a relational expression between a scattering vector and a diffraction angle, and the background was removed. Thereafter, peak fitting was performed and the peak intensity was calculated. Here, the peak intensity refers to the area of the peak. The intensity of each of the oblique orientation component and the vertical orientation component was obtained by using a similar method. Thereafter, an intensity ratio (vertical orientation component/horizontal orientation component) between the vertical orientation component and the horizontal orientation component was calculated, and an orientation index of Sample 1 was obtained. For Samples 2 to 6, the orientation index was obtained by using a similar method. It is to be noted that the smaller the value of the orientation index obtained by the above method is, the stronger the horizontal orientation is.

[Experiment 2; Evaluation of Electric Characteristics]

Experiment Example 1

As Experiment example 1, a photoelectric conversion device was fabricated by depositing layers up to the buffer layer using a similar method and a similar material to those used in the method of fabricating Sample 1 for 2D-GIXD evaluation described above, and thereafter depositing an upper electrode.

First, after a glass substrate with an ITO electrode (lower electrode) having a thickness of 50 nm was cleaned by a UV/ozone process, a photoelectric conversion layer was deposited at a substrate temperature of 0° C. by a resistance heating method while rotating a substrate holder in vacuum of $1 \times 10^{-5}$ Pa or less. As a material of the photoelectric conversion layer, DTP-DTT represented by the above formula (1-2) as the one organic semiconductor material (hole transporting material), a $F_6$-SubPc-$OC_6F_5$ represented by the above formula (18-1) and a $C_{60}$ represented by the above formula (19-1) were used as the other organic semiconductor material, and these were simultaneously deposited. A ratio of a deposition speed was DTP-DTT: $F_6$-SubPc-$OC_6F_5$:$C_{60}$=2:2:1. Film formation was so performed that the total film thickness was 230 nm. Subsequently, $B_4$PyMPM represented by the foregoing formula (21) was deposited with a thickness of 5 nm by a vacuum evaporation method at a substrate temperature of 0° C. as a buffer layer on the photoelectric conversion layer. Finally, AlSiCu alloy was deposited to a thickness of 100 nm by a vapor deposition method as an upper electrode. Thereby, a photoelectric conversion device (Experiment example 1) having a photoelectric conversion region of 1 mm×1 mm was fabricated.

Experiment Example 2

A photoelectric conversion device (Experiment example 2) was fabricated by a method similar to that in Experiment example 1 except that DBT-DTT represented by the above formula (1-1) was used as the hole transporting material.

Experimental Example 3

A photoelectric conversion device (Experiment example 3) was fabricated by a method similar to that in Experiment example 1 except that DTP-rBDT represented by the following formula (9-2) was used as the hole transporting material. In addition, a sample for 2D-GIXD evaluation was also created by a method similar to the method of fabricating Sample 1 for 2D-GIXD evaluation described above.

Experiment Example 4

A photoelectric conversion device (Experiment example 4) was fabricated by a method similar to that in Experiment example 1 except that DBP-2T represented by the following formula (4-1) was used as the hole transporting material. In addition, a sample for 2D-GIXD evaluation was also created by a method similar to the method of fabricating Sample 1 for 2D-GIXD evaluation described above.

Experiment Example 5

A photoelectric conversion device (Experiment example 5) was fabricated by a method similar to that in Experiment example 1 except that DBP-NDT represented by the following formula (17-1) was used as the hole transporting material. In addition, a sample for 2D-GIXD evaluation was also created by a method similar to the method of fabricating Sample 1 for 2D-GIXD evaluation described above.

Experiment Example 6

A photoelectric conversion device (Experiment example 6) was fabricated by a method similar to that in Experiment example 1 except that DBP-BBBT represented by the following formula (2-1) was used as the hole transporting material. In addition, a sample for 2D-GIXD evaluation was also created by a method similar to the method of fabricating Sample 1 for 2D-GIXD evaluation described above.

Experimental Example 7

A photoelectric conversion device (Experiment example 7) was fabricated by a method similar to that in Experiment example 1 except that DP-DTT represented by the foregoing formula (22) was used as the hole transporting material.

Experiment Example 8

A photoelectric conversion device (Experiment example 7) was fabricated by a method similar to that in Experiment example 1 except that DBPBT-BTBT represented by the foregoing formula (13-30) was used as the hole transporting material.

[Chem. 11]

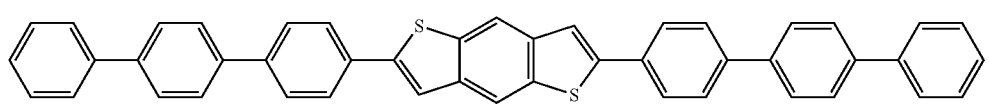

(9-2)

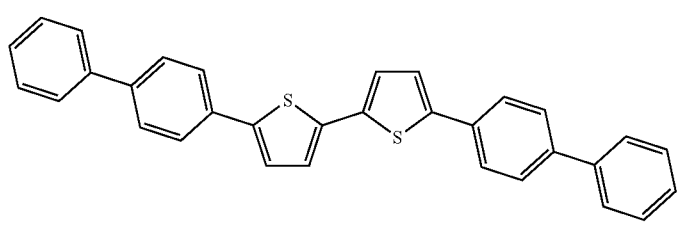

(4-1)

-continued

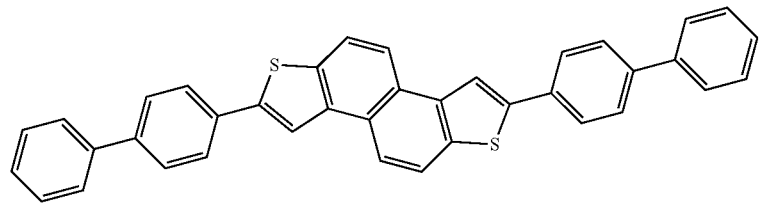

(17-1)

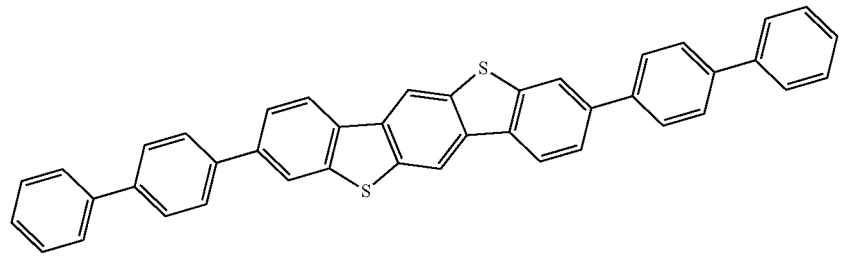

(2-1)

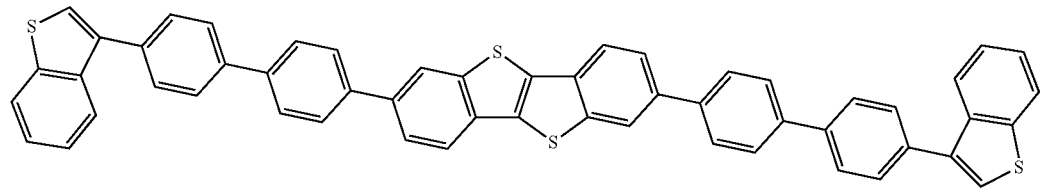

(13-20)

Quantum efficiency (external quantum efficiency; EQE) of Experiment examples 1 to 8 was evaluated using a semiconducting parameter analyzer. Specifically, external photoelectric conversion efficiency was calculated from a light current value and a dark current value in a case where an amount of light (LED light having a wavelength of 560 nm) applied from the light source to the photoelectric conversion device through a filter was set to 1.62 µW/cm$^2$, and a bias voltage applied between the electrodes was −2.6 V.

Further, responsiveness of Experiment examples 1 to 8 was also evaluated. The responsiveness was evaluated by measuring a speed at which the light current value observed by the semiconductor parameter analyzer at the time of light application was fallen after the light application was stopped. Specifically, the amount of light applied from the light source to the photoelectric conversion device through the filter was set to 1.62 µW/cm$^2$, and the bias voltage applied between the electrodes was set to −2.6 V. After a steady current was observed in this state, the light application was stopped and a state of attenuation of the current was observed. Subsequently, the area surrounded by a current-time curve and the dark current was considered to be 100%, and a time until this area corresponds to 3% was used as an index of the responsiveness. All the evaluations were performed at a room temperature.

Further, the orientation was evaluated using a method similar to that in Experiment 1 described above for the respective samples for 2D-GIXD evaluation fabricated in Experiment examples 3 to 6 and 8.

Table 3 summarizes the hole transporting materials used in Experiment examples 1 to 8 and results of the quantum efficiency and response speed of Experiment examples 1 to 8 obtained by the above methods. Further, a composition of the photoelectric conversion layer of Experiment examples 1, 2, and 7 fabricated in Experiment 2 has a configuration similar to that of Samples 1 to 6 created in Experiment 1. That is, the photoelectric conversion layer of Experiment example 1 has a composition similar to that of Samples 1 and 4 in Experiment 1, the photoelectric conversion layer of Experiment example 2 has a composition similar to that of Samples 2 and 5, and the photoelectric conversion layer of Experiment example 7 has a composition similar to that of Samples 3 and 6. Therefore, the orientations of Samples 1 to 6 obtained in Experiment 1 are also summarized in Table 3.

TABLE 3

| | | Orientation | | | | |
| | Hole transporting material | 0° C. film formation | 25° C. film formation | Variation rate (25° C. film formation/ 0° C. film formation) | Quantum efficiency (%) | Response speed (a.u.) |
| --- | --- | --- | --- | --- | --- | --- |
| Experiment example 1 | Formula (1-2) | 0.45 | 0.45 | 1.00 | 97 | 9.9 |

TABLE 3-continued

|  | Hole transporting material | Orientation | | | Quantum efficiency (%) | Response speed (a.u.) |
|---|---|---|---|---|---|---|
|  |  | 0° C. film formation | 25° C. film formation | Variation rate (25° C. film formation/ 0° C. film formation) |  |  |
| Experiment example 2 | Formula (1-1) | 0.69 | 0.84 | 1.21 | 92 | 33 |
| Experiment example 3 | Formula (9-2) | 0.44 | 0.42 | 0.94 | 88 | 1 |
| Experiment example 4 | Formula (4-1) | 0.79 | 0.76 | 0.96 | 90 | 15 |
| Experiment example 5 | Formula (17-1) | 0.89 | 0.90 | 1.01 | 92 | 5 |
| Experiment example 6 | Formula (2-1) | 0.39 | 0.42 | 1.07 | 89 | 1 |
| Experiment example 7 | Formula (22) | 0.64 | 2.11 | 3.28 | 35 | 3000 |
| Experiment example 8 | Formula (13-30) | 0.50 | 0.47 | 0.94 | 23 | 6 |

From Table 3, it was found that DP-DTT (formula (22)), DBP-DTT (formula (1-1)), DTP-DTT (formula (1-2)), DTP-rBDT (formula (9-2)), DBP-2T (formula (4-1)), DBP-NDT (formula (17-1)), DBP-BBBT (formula (2-1)), and DBPBT-BTBT (formula (13-30)) all exhibited horizontal orientation in a case where the film formation was performed at the substrate temperature 0° C. Further, in Experiment example 7 using DP-DTT (formula (22)), the quantum efficiency and the response speed were remarkably decreased as compared with Experiment example 1 using DTP-DTT (formula (1-2)), Experiment example 2 using DBP-DTT (formula (1-1)), Experiment example 3 using DTP-rBDT (formula (9-2)), Experiment example 4 using DBP-2T (formula (4-1)), Experiment example 5 using DBP-NDT (formula (17-1)), and Experiment example 6 using DBP-BBBT (formula (2-1)). This is considered to be related to the fact that, in a case where the film formation was performed at the substrate temperature of 25° C., the value of the orientation index of DP-DTT (formula (22)) was greatly varied as compared with that of DBP-DTT (formula (1-1)), DTP-DTT (formula (1-2)), and the like. That is, in order to obtain high quantum efficiency and a high response speed, it is considered preferable to use a material having orientation that varies less in accordance with a film formation temperature. It is to be noted that, in Experiment example 8 using DBPBT-BTBT (formula (13-30)), a decrease in quantum efficiency was confirmed as in Experiment example 7. However, this is considered to be a result of inconsistency of energy level with the material used with DBPBT-BTBT (formula (13-30)). However, since the response speed is high, it is understood that the conduction property is favorable.

FIG. 29 illustrates a relationship between the film formation temperature of the photoelectric conversion layer using each organic semiconductor material obtained by 2D-GIXD and the orientation in the photoelectric conversion layer. It was found that all of the organic semiconductor materials were horizontally oriented at the film formation temperature of 0° C., whereas a ratio of the vertical orientation of DP-DTT (formula (22)) was higher at the film formation temperature of 25° C. It is considered that the DP-DTT (formula (22)) has a strong intermolecular interaction, and the orientation deteriorated with crystallization.

FIG. 30 illustrates a relationship between the orientation in the photoelectric conversion layer at the film formation temperature of 0° C. and the quantum efficiency of the photoelectric conversion layer using each organic semiconductor material obtained by 2D-GIXD. FIG. 31 illustrates a relationship between the orientation of each organic semiconductor material in the photoelectric conversion layer at the film formation temperature of 0° C. and the response speed of the photoelectric conversion layer using each organic semiconductor material obtained by 2D-GIXD. Although DP-DTT (formula (22)), DBP-DTT (formula (1-1)), and DTP-DTT (formula (1-2)) were horizontally oriented at the film formation temperature of 0° C., the photoelectric conversion device using DP-DTT (formula (22)) exhibited significantly deteriorated quantum efficiency and response speed compared to the photoelectric conversion devices using DBP-DTT (formula (1-1)) and DTP-DTT (formula (1-2)). Since DP-DTT (formula (22)) has a property of easily causing crystallization, it is easy for a large defect to be generated at the grain boundary. This is considered to have inhibited conduction. Further, it is also considered that large variation in orientation resulting from the film formation temperature of DP-DTT (Expression (22)) is caused by the strength of the intermolecular interaction and the high crystallinity. Such molecules result in poor grain-to-grain bonding at the grain boundary formed within the photoelectric conversion layer. This is considered to increase resistance and deteriorate a conduction property.

FIG. 32 illustrates a relationship between a rate of variation in orientation resulting from a film formation temperature of each organic semiconductor material obtained by 2D-GIXD and quantum efficiency at the film formation temperature of 0° C. FIG. 33 illustrates a relationship between the rate of variation in orientation resulting from the film formation temperature of each organic semiconductor material obtained by 2D-GIXD and a response speed at the film formation temperature of 0° C. Focusing on variation in orientation in accordance with temperature, it was found that the photoelectric conversion device using the organic semiconductor material whose orientation is remarkably varied by the variation in film formation temperature as DP-DTT (formula (22)) has low electric characteristics, and favorable electric characteristics can be obtained in the photoelectric conversion device using the organic semiconductor material whose orientation is difficult to be varied by the variation in film formation temperature as DBP-DTT (formula (1-1)), DTP-DTT (formula (1-2)), DTP-rBDT (formula (9-2)), DBP-2T (formula (4-1)), DBP-NDT (formula (17-1)), DBP-BBBT (formula (2-1)), and DBPBT-BTBT (formula (13-30)).

In addition, from FIG. 32, it was found that the rate of variation in orientation, of each organic semiconductor material in the photoelectric conversion layer, of each film formation temperature (the first temperature and the second temperature) was in the following ranges. For example, it was found that, in order to obtain quantum efficiency of 50% or higher, the variation rate of orientation is preferably 2.7 times or less, and in order to obtain quantum efficiency of 80% or higher, the variation rate of orientation is preferably 1.6 times or less. Further, for example, it was found that 1.3 times or less is preferable in order to obtain quantum efficiency equivalent to that of DBP-DTT. Further, since it is unlikely that the orientation is improved when the film formation temperature is increased, the lower limit is set to, for example, 0.9 times or more.

FIG. 34 is a scattering spectrum diagram for each film formation temperature of Sample 3 obtained by XRD (X-ray diffraction). FIG. 35 is a scattering spectrum diagram for each film formation temperature of Sample 2 obtained by XRD. In the photoelectric conversion layer (Sample 3) using DP-DTT represented by formula (22) as the hole transporting material, a peak on the low angle side near 5.1° and a peak on the high angle side near 19.1°, 23.8°, and 28.2° were confirmed. When compared between the film formation temperature of 0° C. and the film formation temperature of 25° C., the peak intensity on the low angle side increased and the peak intensity on the high angle side decreased when the film formation temperature was increased. From this, it was qualitatively found that DP-DTT (formula (22)) had a decrease in horizontally-oriented crystal and an increase in vertically-oriented crystal as a result of an increase in film formation temperature. In contrast, in the photoelectric conversion layer (Sample 2) in which DBP-DTT represented by the formula (1-1) was used as the hole transporting material, even if the film formation temperature was increased, the peak on the low angle side (a peak which is difficult to confirm in the bulk hetero film and appears near 3.6° in a single film) did not appear, and a decrease in peak on the high angle side was not observed. As described above, the orientation can be qualitatively confirmed by a thin film method, and it can be said that a material in which the low-angle peak intensity increases remarkably or the high-angle peak intensity decreases remarkably at the time of high-temperature film formation is not preferable from the viewpoint of orientation.

[Experiment 3: Evaluation of Orientation Angle Range and Orientation Variation Amount]

Next, the orientation angle range and the orientation variation amount were evaluated. Samples for orientation angle evaluation were fabricated using the following method.

Experiment Example 9

As Experimental example 9, DTP-DTT represented by the foregoing formula (1-2) as the one organic semiconductor material (hole transporting material) and $F_6$-SubPc-$OC_6F_5$ represented by the foregoing formula (18-1) and $C_{60}$ represented by the foregoing formula (19-1) as the other organic semiconductor material were used and they were simultaneously deposited on a silicon (Si) substrate having mirror surfaces on both sides. A ratio of deposition speed was DTP-DTT:$F_6$-SubPc-$OC_6F_5$: $C_{60}$=2:2:1, and the film formation was so performed that the total film thickness was 100 nm.

Experiment Examples 10 to 16

Photoelectric conversion devices (Experiment examples 10 to 16) having a configuration similar to that in Experiment example 9 were fabricated by a method similar to that in Experiment example 9 except that the materials listed in Experiment examples 2 to 8 above were used as the hole transporting materials.

For Experiment examples 9 to 16, the orientation angle of the hole transporting material at film formation temperatures of 0° C. and 25° C. were measured, and a variation amount (orientation variation amount) thereof was calculated. The following measurement conditions and calculation methods were used for each orientation angle.

Apparatus: Thermo-Fisher scientific Nicolet 8700 FT-IR spectrometer with pMAIRS equipment
Detector: MCT
Entering angle condition: 9-44° (5° step)
Number of times of integration: 300 times
Wavenumber resolution: 8 cm$^{-1}$ Multi-angle incidence resolution spectrometry (pMAIRS) performs measurement on the substrate by an infrared transmission method at a plurality of incident angles, and from the obtained results, obtains an in-plane (IP) spectrum and an out-of-plane (OP) spectrum by a CLS regression formula. When attention is paid to a peak assigned to a certain transition dipole moment, an orientation angle Φ of the transition dipole moment from the electrode plane can be obtained by the following mathematical expression (1) from the peak intensity ratio between the IP spectrum and the OP spectrum of the peak. As the peak for calculating the orientation angle, a transition dipole moment in a molecule major-axis direction is preferable, but a transition dipole moment in a direction perpendicular to the molecular plane may be used. In a case where the transition dipole moment in the direction perpendicular to the molecular plane is used, an angle between the major axis direction of the molecule and the substrate is calculated by using the following mathematical expression (2). In the present experiment example, the angle formed with the substrate was calculated as the orientation angle by the mathematical expression (1) using the peak attributed to the transition dipole moment in the major axis direction of the molecule.

[Math. 1]

$$\phi = 90° - \tan^{-1}\sqrt{\frac{2I_{IP}}{I_{OP}}} \quad (1)$$

$$\phi = \tan^{-1}\sqrt{\frac{2I_{IP}}{I_{OP}}} \quad (2)$$

$I_{IP}$: peak intensity in the IP spectrum, $I_{OP}$: peak intensity in the OP spectrum)

Table 4 summarizes the hole transporting materials used in Experiment examples 9 to 16 and the orientation angles (°) with the electrode plane and orientation variation amounts at respective film formation temperatures in Experiment examples 9 to 16 obtained by the above method. In addition, Table 4 also describes results of quantum efficiency and response speed obtained in Experiment 2 of Experiment examples 1 to 8 having a material configuration similar to that of the photoelectric conversion layer of Experiment examples 9 to 16.

TABLE 4

| | | Orientation angle with electrode plane (°) | | | | |
|---|---|---|---|---|---|---|
| | Hole transporting material | 0° C. film formation (B) | 25° C. film formation (a) | Orientation variation amount Δ(A − B) | Quantum efficiency (%) | Response speed (a.u.) |
| Experiment example 9 | Formula (1-2) | 30 | 97 | 1 | 97 | 9.9 |
| Experiment example 10 | Formula (1-1) | 33 | 92 | 4 | 92 | 33 |
| Experiment example 11 | Formula (9-2) | 29 | 88 | 2 | 88 | 1 |
| Experiment example 12 | Formula (4-1) | 34 | 90 | 5 | 90 | 15 |
| Experiment example 13 | Formula (17-1) | 30 | 92 | 2 | 92 | 5 |
| Experiment example 14 | Formula (2-1) | 31 | 31 | 0 | 89 | 1 |
| Experiment example 15 | Formula (22) | 46 | 10 | 10 | 35 | 3000 |
| Experiment example 16 | Formula (13-30) | 22 | 22 | 0 | 23 | 23 |

From Table 4, it was found that the response speed of the photoelectric conversion device using DBP-DTT (formula (1-1)), DTP-DTT (formula (1-2)), DTP-rBDT (formula (9-2)), DBP-2T (formula (4-1)), DBP-NDT (formula (17-1)), DBP-BBBT (formula (2-1)), and DBPBT-BTBT (formula (13-30)) as the hole-transporting materials was remarkably improved as compared with that in the case of using DP-DTT (formula (22)). From the result of the response speed, it can be said that it is preferable that the orientation variation amount resulting from the difference in film formation temperature be less than 10°. More preferably, from the orientation variation amount of Experiment example 15 and the orientation variation amount of Experiment example 10, it is set to 7° which is an average value thereof or less. In addition, it can be said that it is preferable that the range of the orientation angle formed by the hole transporting material with respect to the electrode plane is less than 46°. Further, although not described here, from the result of the response speed using another hole transporting material, it was found that the response speed is improved by setting the range of the orientation angle between the hole transporting material and the electrode plane to 37° or less.

FIG. 36 illustrates the relationship between the film formation temperature of the photoelectric conversion layer using each organic semiconductor material obtained by pMAIRS and the orientation angle in the photoelectric conversion layer. It was found that the orientation angle of all the organic semiconductor materials were between about 30° and 45° at the film formation temperature of 0° C., whereas the orientation angle of DP-DTT (formula (22)) varied significantly to about 55° at the film formation temperature of 25° C.

FIG. 37 illustrates a relationship between the amount of variation in orientation angle resulting from the film formation temperature and quantum efficiency at the film formation temperature of 0° C. of each organic semiconductor material obtained by pMAIRS. FIG. 38 illustrates a relationship between the amount of variation in orientation angle resulting from the film formation temperature and a response speed at the film formation temperature of 0° C. of each organic semiconductor material obtained by pMAIRS. Focusing on the amount of variation in the orientation angle resulting from the temperature variation, it was found that the photoelectric conversion device using the organic semiconductor material whose amount of variation in the orientation angle is significantly varied according to the variation in the film formation temperature such as DP-DTT (formula (22)) has low electric characteristics, and favorable electric characteristics were obtained in the photoelectric conversion device using the organic semiconductor material whose amount of variation in the orientation angle is difficult to be varied according to the variation in the film formation temperature such as DBP-DTT (formula (1-1)), DTP-DTT (formula (1-2)), DTP-rBDT (formula (9-2)), DBP-2T (formula (4-1)), DBP-NDT (formula (17-1)), DBP-BBBT (formula (2-1)), and DBPBT-BTBT (formula (13-30)).

Although description has been given above with reference to embodiments and working examples, contents of the present disclosure are not limited to the above-described embodiments and the like, and various modifications can be made. For example, in the above-described embodiment, as an photoelectric conversion device, the configuration is provided in which the organic photoelectric conversion section 11G detecting green light, the inorganic photoelectric conversion section 11B detecting blue light, and the inorganic photoelectric conversion section 11R detecting red light are stacked, but the contents of the present disclosure are not limited to such a structure. That is, the organic photoelectric conversion section may detect the red light or the blue light, or the inorganic photoelectric conversion section may detect the green light.

In addition, the number of these organic photoelectric conversion section and inorganic photoelectric conversion sections or a proportion thereof is not limited. Two or more organic photoelectric conversion sections may be provided or color signals of a plurality of colors may be obtained only by the organic photoelectric conversion section. Furthermore, the structure in which the organic photoelectric conversion section and the inorganic photoelectric conversion sections are stacked in the vertical direction is not limiting, and the organic photoelectric conversion section and the inorganic photoelectric conversion sections may be arranged side by side along a substrate surface.

Furthermore, in the above-described embodiment and the like, the configuration of the solid imaging apparatus of the back irradiation type is exemplified; however, the contents of the present disclosure are also applicable to a solid imaging apparatus of a front irradiation type. Further, in the photoelectric conversion device of the present disclosure, all of the constituent elements described in the above embodiments need not be provided, and on the contrary, other layers may be provided.

Further, in the above-described embodiments and the like, an example in which the photoelectric conversion device 10 is used as the imaging device configuring the imaging apparatus 1 is described, but the photoelectric conversion device 10 of the present disclosure may be applied to a solar cell.

It is to be noted that the effects described in the present specification are merely examples and non-limiting. In addition, there may be other effects.

[1]
A photoelectric conversion device including:
a first electrode;
a second electrode opposed to the first electrode; and
a photoelectric conversion layer provided between the first electrode and the second electrode and including at least one type of one organic semiconductor material having crystallinity, in which
variation in a ratio between horizontally-oriented crystal and vertically-oriented crystal in the photoelectric conversion layer is three times or less between a case where film formation of the one organic semiconductor material is performed at a first temperature and a case where the film formation of the one organic semiconductor material is performed at a second temperature, the second temperature being higher than the first temperature.

[2]
The photoelectric conversion device according to [1] described above, in which the one organic semiconductor material has a carrier transporting property.

[3]
The photoelectric conversion device according to [1] or [2] described above, in which the one organic semiconductor material has a hole transporting property.

[4]
The photoelectric conversion device according to any one of [1] to [3] described above, in which the one organic semiconductor material is a low molecular weight material having a molecular weight of 100 or more and 3000 or less.

[5]
The photoelectric conversion device according to [3] or [4] described above, in which
the photoelectric conversion layer includes one or more types of another organic semiconductor material,
a HOMO level of the one organic semiconductor material is higher than a HOMO level of at least one type of the other organic semiconductor material.

[6]
The photoelectric conversion device according to any one of [1] to [5] described above, in which the one organic semiconductor material has an aromatic skeleton and an aromatic substituent in a molecule.

[7]
The photoelectric conversion device according to [6] described above, in which the aromatic substituent is any of the following formulae (A-1) to (A-50).

[Chem. 1A]

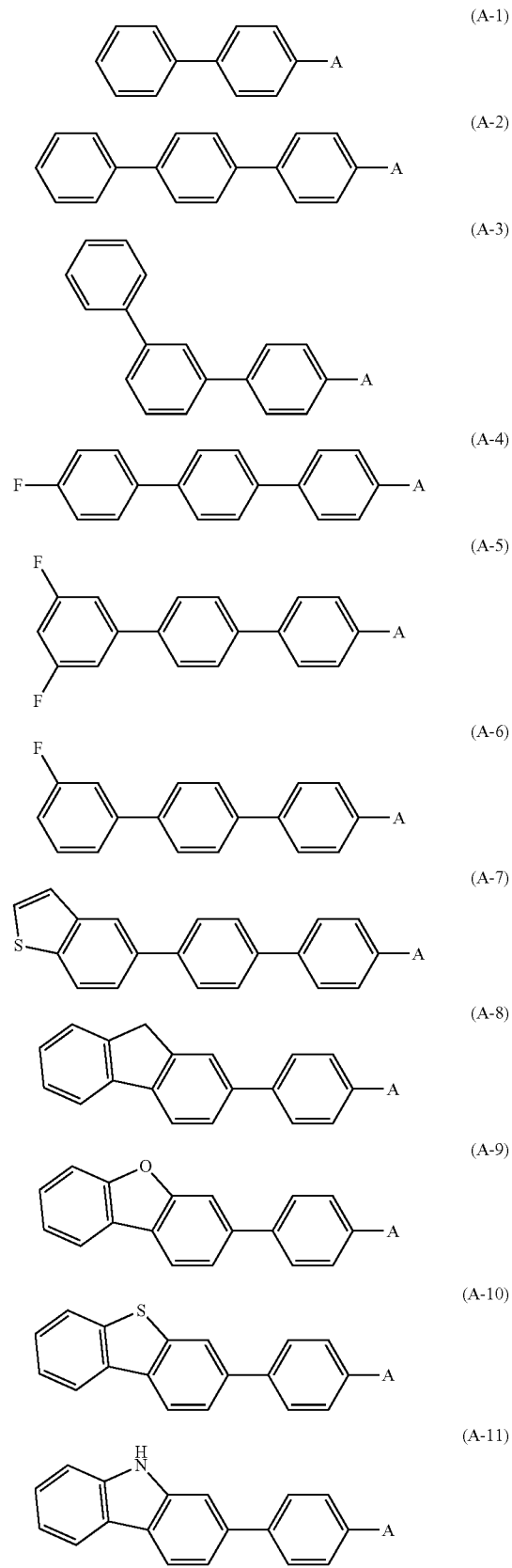

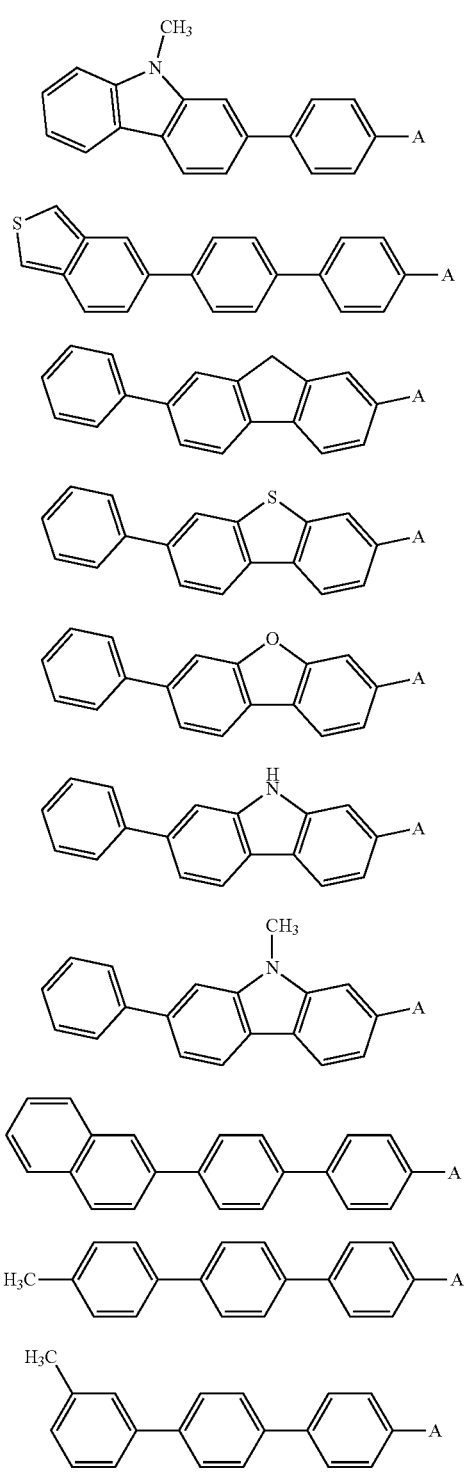
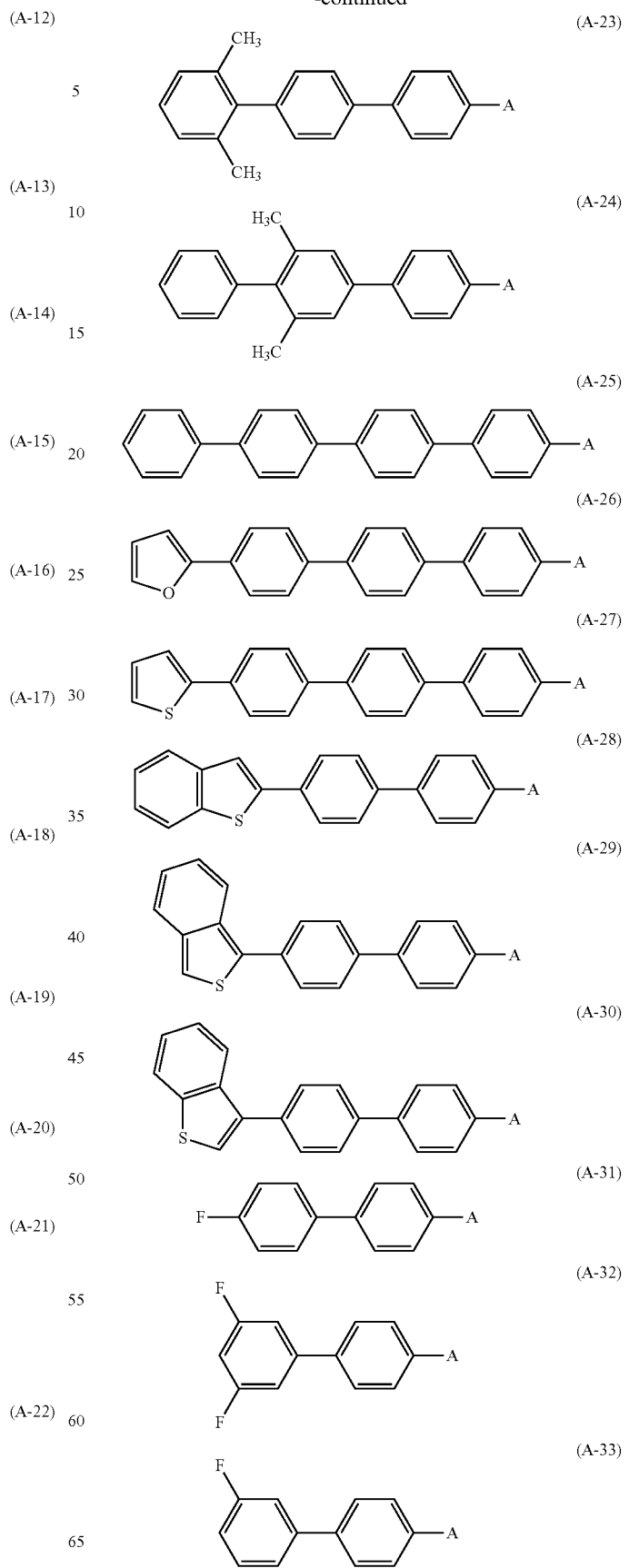
[Chem. 1B]

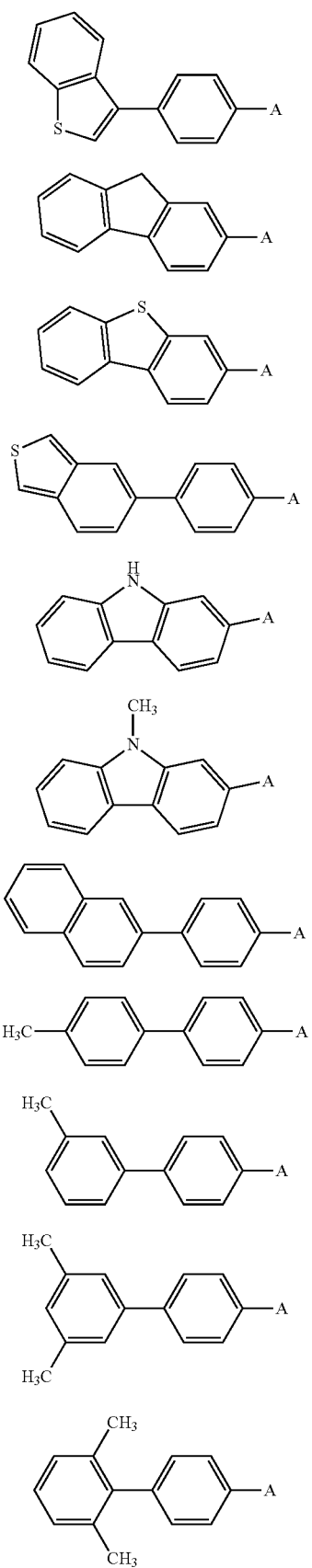

(A-34)
(A-35)
(A-36)
(A-37)
(A-38)
(A-39)
(A-40)
(A-41)
(A-42)
(A-43)
(A-44)

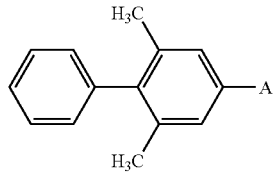

(A-45)

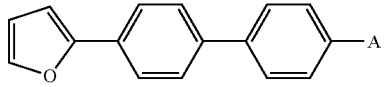

(A-46)

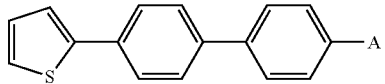

(A-47)

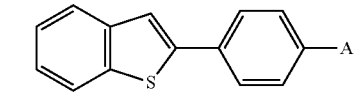

(A-48)

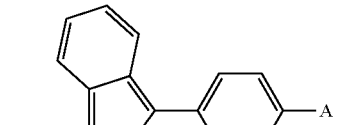

(A-49)

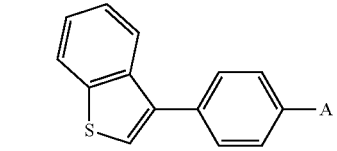

(A-50)

The photoelectric conversion device according to [6] described above, in which the aromatic skeleton is a monocyclic or polycyclic heterocyclic aromatic skeleton.

[9]

The photoelectric conversion device according to [8] described above, in which the monocyclic or polycyclic heterocyclic aromatic skeleton is any of the following general formulae (1) to (17).

[Chem. 2]

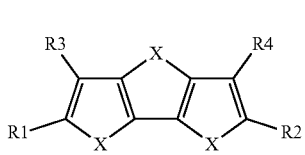

(1)

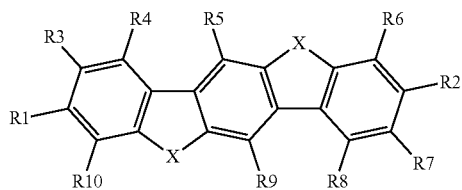

(2)

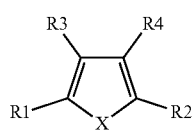

(3)

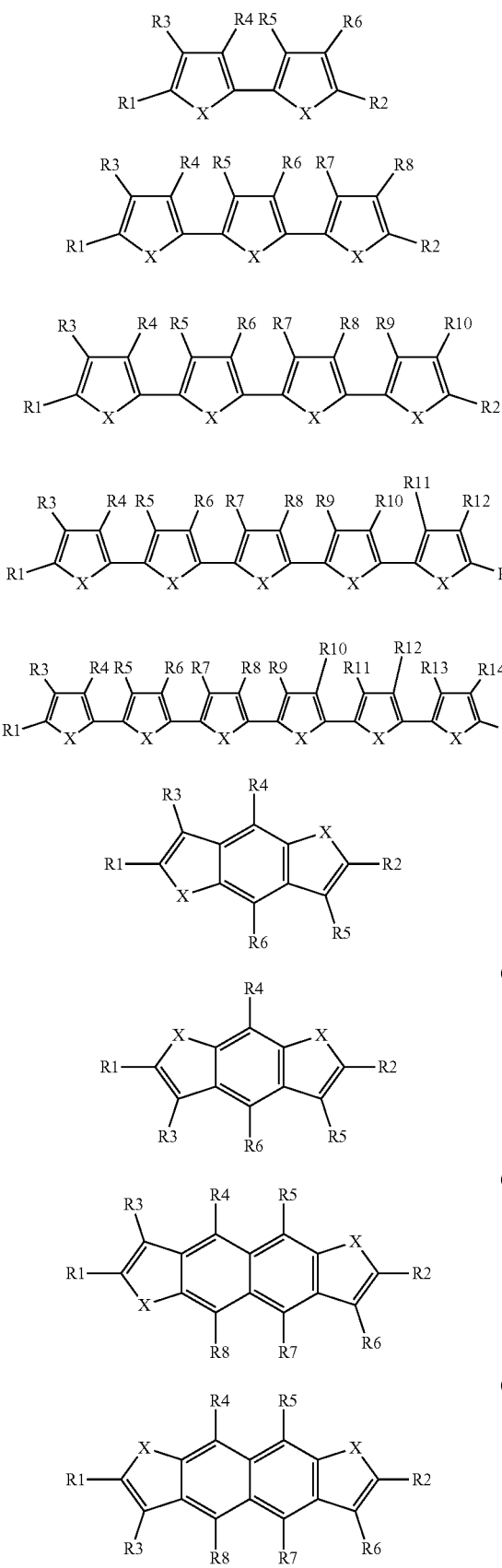
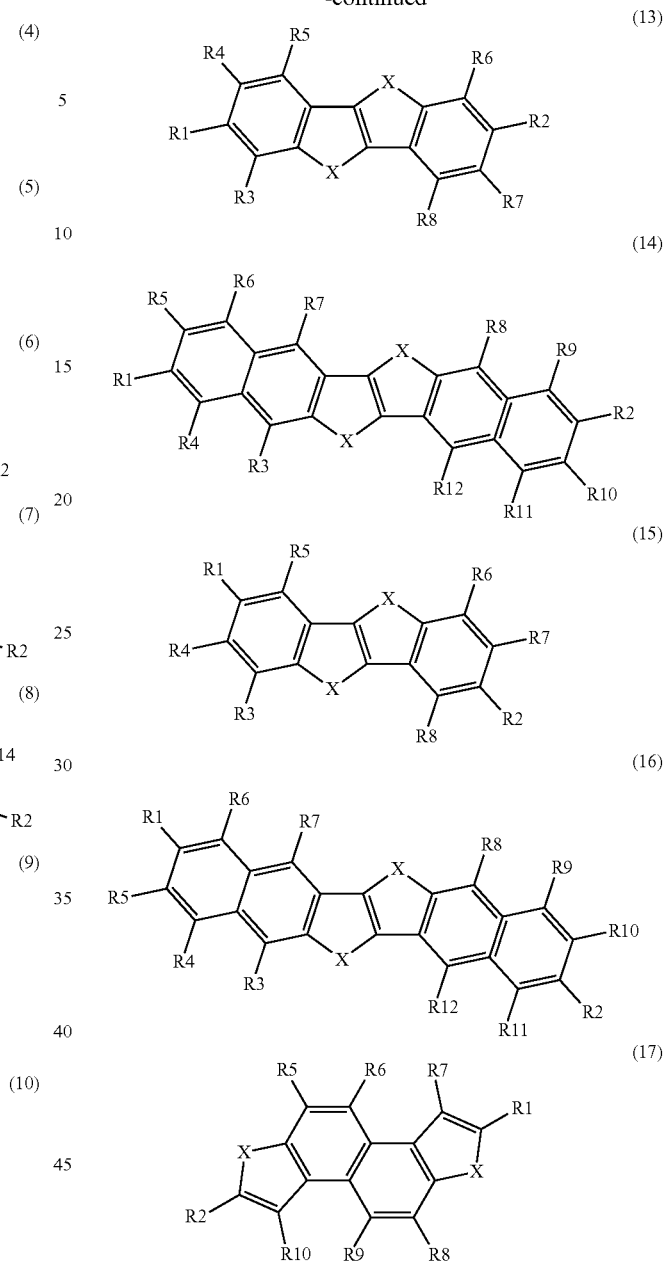

(X is any of oxygen (O), sulfur (S), selenium (Se), and tellurium (Te). R1 and R2 are each independently a substituent represented by the formulae (A-1) to (A-50). R3 to R14 are each independently a hydrogen atom, a halogen atom, a straight-chain, branched, or cyclic alkyl group, an aryl group, or a derivative thereof. Any adjacent ones of R1 to R14 may be bonded to each other to form a condensed aliphatic ring or a condensed aromatic ring. The condensed aliphatic ring or the condensed aromatic ring may contain one or more atoms of oxygen (O), nitrogen (N), sulfur (S), selenium (Se), and tellurium (Te).)

[10]
The photoelectric conversion device according to any one of [1] to [9] described above, in which the one organic semiconductor material is an aromatic compound having a molecular length greater than 1.6 nanometers and equal to or smaller than 10 nanometers.

[11]

The photoelectric conversion device according to [1] or [2] described above, in which the one organic semiconductor material has an electron transporting property.

[12]

The photoelectric conversion device according to [11] described above, in which the photoelectric conversion layer includes another organic semiconductor material, a LUMO level of the one organic semiconductor material is lower than a LUMO level of at least one type of the other organic semiconductor material.

[13]

The photoelectric conversion device according to any one of [1] to [12] described above, in which the photoelectric conversion layer includes another organic semiconductor material, and the other organic semiconductor material is subphthalocyanine or a derivative thereof represented by the following general formula (2).

[Chem. 3]

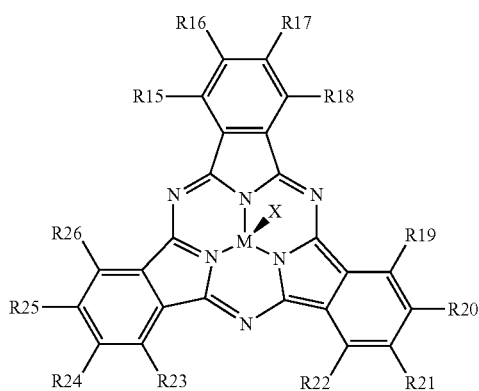

(2)

(R15 to R26 are each independently selected from a group consisting of a hydrogen atom, a halogen atom, a straight-chain, branched, or cyclic alkyl group, a thioalkyl group, a thioaryl group, an arylsulfonyl group, an alkylsulfonyl group, an amino group, an alkylamino group, an arylamino group, a hydroxy group, an alkoxy group, an acylamino group, an acyloxy group, a phenyl group, a carboxy group, a carboxamide group, a carboalkoxy group, an acyl group, a sulfonyl group, a cyano group, and a nitro group, and any adjacent ones of R15 to R26 may be a portion of a condensed aliphatic ring or a condensed aromatic ring. The condensed aliphatic ring or the condensed aromatic ring may include one or more atoms other than carbon. M is boron, divalent metal, or trivalent metal. X is a substituent selected from a group consisting of halogen, a hydroxy group, a thiol group, an imide group, a substituted or unsubstituted alkoxy group, a substituted or unsubstituted aryloxy group, a substituted or unsubstituted alkyl group, a substituted or unsubstituted alkylthio group, and a substituted or unsubstituted arylthio group.)

[14]

The photoelectric conversion device according to any one of [1] to [13] described above, in which the photoelectric conversion layer includes another organic semiconductor material, and the other organic semiconductor material is fullerene or a fullerene derivative represented by the following general formula (3) or (4).

[Chem. 4]

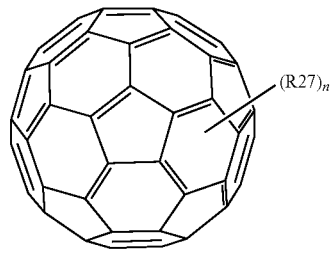

(3)

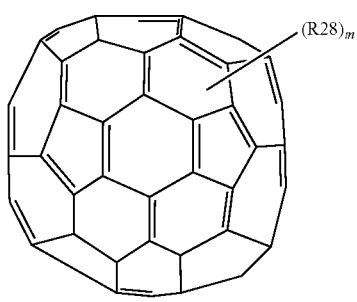

(4)

(R27 and R28 are each a hydrogen atom, a halogen atom, a straight-chain, branched, or cyclic alkyl group, a phenyl group, a group having a straight-chain or condensed aromatic compound, a group having a halide, a partial fluoroalkyl group, a perfluoroalkyl group, a silylalkyl group, a silylalkoxy group, an arylsilyl group, an arylsulfanyl group, an alkylsulfanyl group, an arylsulfonyl group, an alkylsulfonyl group, an alkylsulfide group, an alkylsulfide group, an amino group, an alkylamino group, an arylamino group, a hydroxy group, an alkoxy group, an acylamino group, an acyloxy group, a carbonyl group, a carboxy group, an carboxyamino group, a carboalkoxy group, an acyl group, a sulfonyl group, a cyano group, a nitro group, a group having a chalcogenide, a phosphine group, a phosphone group, or a derivative thereof. "n" and "m" are each an integer of 0 or greater.)

[15]

The photoelectric conversion device according to any one of [1] to [14] described above, in which a variation rate of orientation between the film formation of the one organic semiconductor material at the first temperature and the film formation of the one organic semiconductor material at the second temperature in the photoelectric conversion layer is 0.9 times or greater and 2.7 times or smaller.

[16]

The photoelectric conversion device according to any one of [1] to [15] described above, in which a difference between the first temperature and the second temperature is equal to or greater than 5 degrees Celsius and equal to or smaller than 35 degrees Celsius, the first temperature is equal to or higher than −10 degrees Celsius and equal to or lower than +10 degrees Celsius, and the second temperature is equal to or higher than 15 degrees Celsius and equal to or lower than 35 degrees Celsius.

[17]
A photoelectric conversion device including:
a first electrode;
a second electrode opposed to the first electrode; and
a photoelectric conversion layer provided between the first electrode and the second electrode and including at least one type of one organic semiconductor material having crystallinity, in which
a variation amount of an angle formed with an electrode surface of the first electrode is smaller than 10 degrees between a case where film formation of the one organic semiconductor material is performed at a first temperature and a case where the film formation of the one organic semiconductor material is performed at a second temperature, the second temperature being higher than the first temperature.

[18]
The photoelectric conversion device according to [17] described above, in which
the angle formed by the one organic semiconductor material in the photoelectric conversion layer and the electrode surface of the first electrode is set as an orientation angle, and
an angle range of the orientation angle of the one organic semiconductor material in the photoelectric conversion layer is smaller than 46 degrees.

[19]
An imaging apparatus in which each pixel includes one or a plurality of organic photoelectric conversion sections,
the organic photoelectric conversion section including:
a first electrode;
a second electrode opposed to the first electrode; and
a photoelectric conversion layer provided between the first electrode and the second electrode and including at least one type of one organic semiconductor material having crystallinity, in which
variation in a ratio between horizontally-oriented crystal and vertically-oriented crystal in the photoelectric conversion layer is three times or less between a case where film formation of the one organic semiconductor material is performed at a first temperature and a case where the film formation of the one organic semiconductor material is performed at a second temperature, the second temperature being higher than the first temperature.

[20]
An imaging apparatus in which each pixel includes one or a plurality of organic photoelectric conversion sections,
the photoelectric conversion device including:
a first electrode;
a second electrode opposed to the first electrode; and
a photoelectric conversion layer provided between the first electrode and the second electrode and including at least one type of one organic semiconductor material having crystallinity, in which
a variation amount of an angle formed with an electrode surface of the first electrode is smaller than 10 degrees between a case where film formation of the one organic semiconductor material is performed at a first temperature and a case where the film formation of the one organic semiconductor material is performed at a second temperature, the second temperature being higher than the first temperature.

DESCRIPTION OF REFERENCE NUMBERS

1 . . . imaging device, 2 . . . electronic device (camera), 10A, 10B . . . photoelectric conversion device, 11 . . . semiconductor substrate, 11G . . . organic photoelectric conversion section, 11R, 11B . . . inorganic photoelectric conversion section, 12, 14 . . . interlayer insulating layer, 12A . . . fixed charge layer, 12B . . . dielectric layer, 13A, 13C . . . pad portion, 13B . . . upper contact, 15 . . . lower electrode, 16 . . . photoelectric conversion layer 16 . . . upper electrode, 18 . . . protective layer, 19 . . . on-chip lens layer, 19L . . . on-chip lens.

The invention claimed is:
1. A photoelectric conversion device comprising:
a first electrode;
a second electrode opposed to the first electrode; and
a photoelectric conversion layer provided between the first electrode and the second electrode and including at least one type of one organic semiconductor material having crystallinity, wherein
variation in a ratio between horizontally-oriented crystal and vertically-oriented crystal in the photoelectric conversion layer is three times or less between a case where film formation of the one organic semiconductor material is performed at a first temperature and a case where the film formation of the one organic semiconductor material is performed at a second temperature, the second temperature being higher than the first temperature,
wherein the one organic semiconductor material has an aromatic skeleton and an aromatic substituent in a molecule, and
wherein the aromatic substituent is any of the following formulae (A-1) to (A-50):

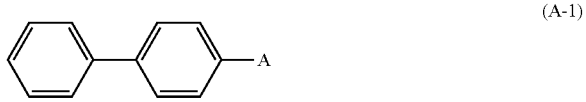
(A-1)

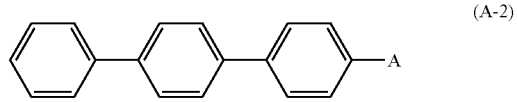
(A-2)

(A-3)

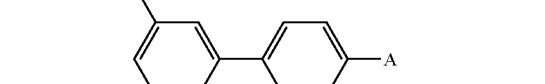
(A-4)

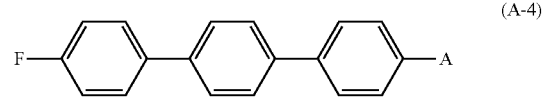
(A-5)

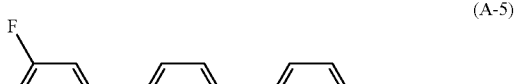
(A-6)

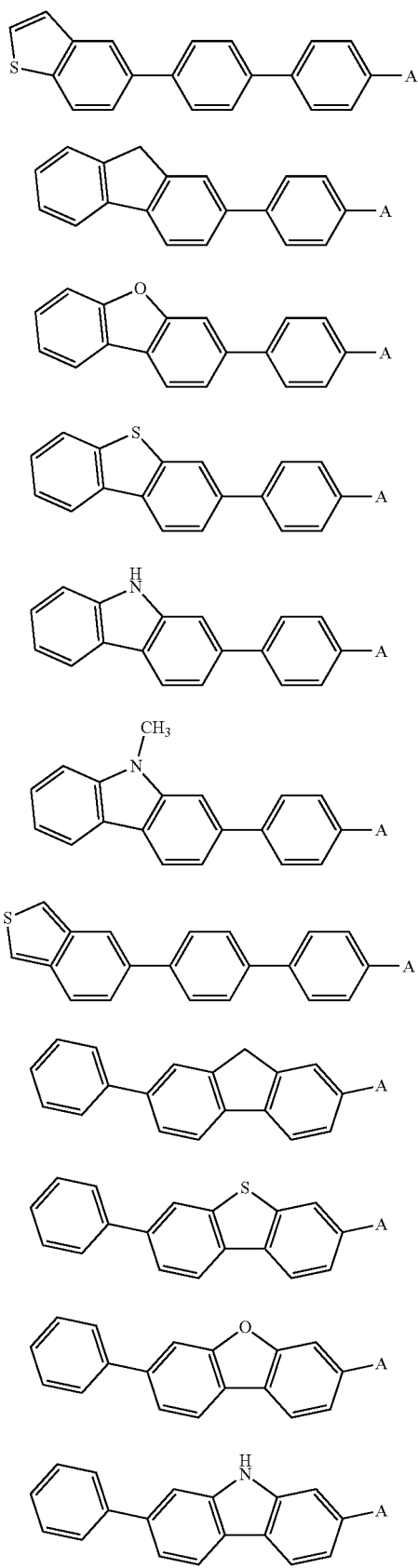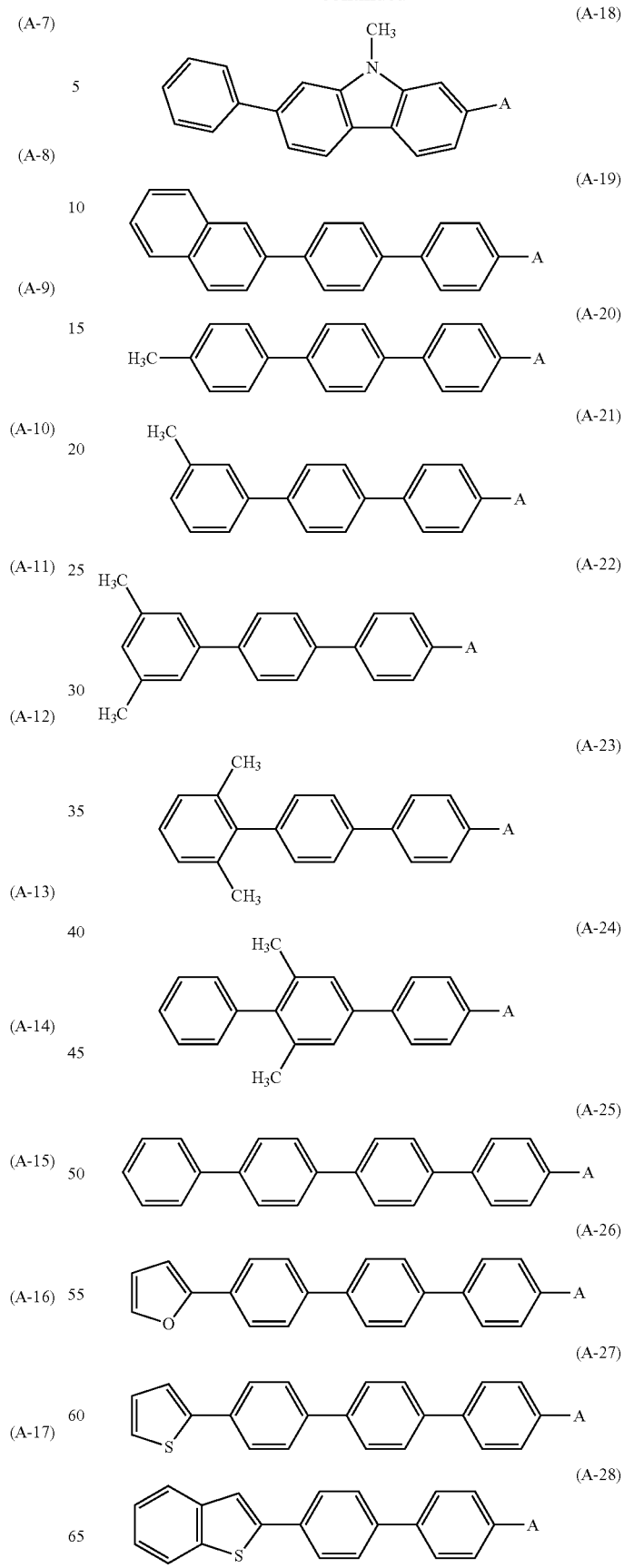

(A-29) 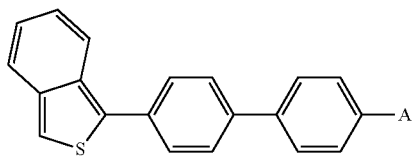
(A-30) 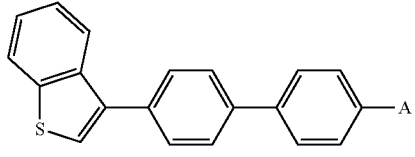
(A-31) 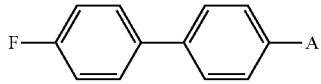
(A-32) 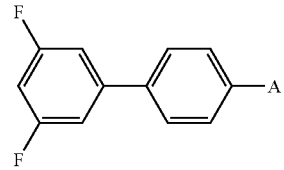
(A-33) 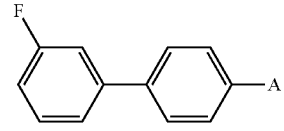
(A-34) 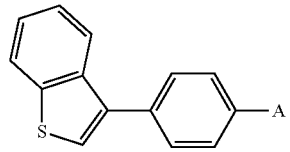
(A-35) 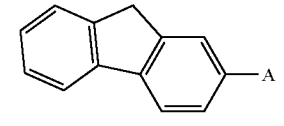
(A-36) 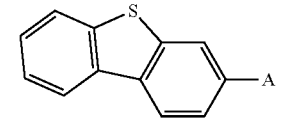
(A-37) 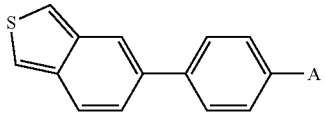
(A-38) 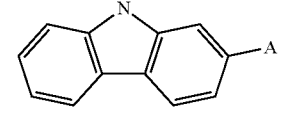
(A-39) 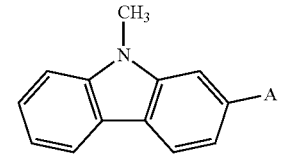
(A-40) 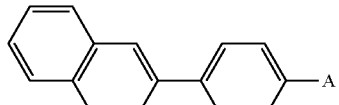
(A-41) 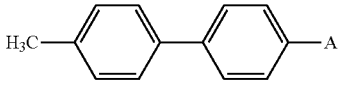
(A-42) 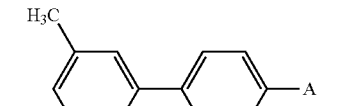
(A-43) 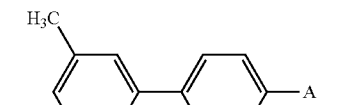
(A-44) 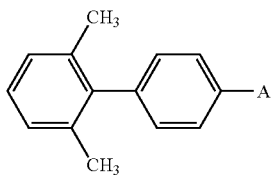
(A-45) 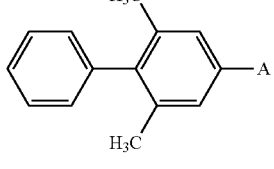
(A-46) 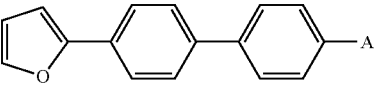
(A-47) 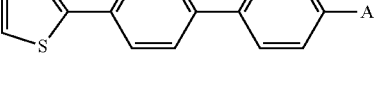
(A-48) 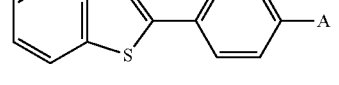
(A-49) 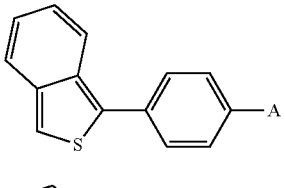
(A-50) 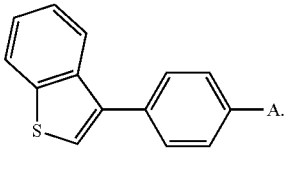

2. The photoelectric conversion device according to claim 1, wherein the one organic semiconductor material has a carrier transporting property.

3. The photoelectric conversion device according to claim 1, wherein the one organic semiconductor material has a hole transporting property.

4. The photoelectric conversion device according to claim 1, wherein the one organic semiconductor material is a low molecular weight material having a molecular weight of 100 or more and 3000 or less.

5. The photoelectric conversion device according to claim 3, wherein
the photoelectric conversion layer includes one or more types of another organic semiconductor material,
a HOMO level of the one organic semiconductor material is higher than a HOMO level of at least one type of the other organic semiconductor material.

6. The photoelectric conversion device according to claim 1, wherein the aromatic skeleton is a monocyclic or polycyclic heterocyclic aromatic skeleton.

7. The photoelectric conversion device according to claim 6, wherein the monocyclic or polycyclic heterocyclic aromatic skeleton is any of the following general formulae (1) to (17);

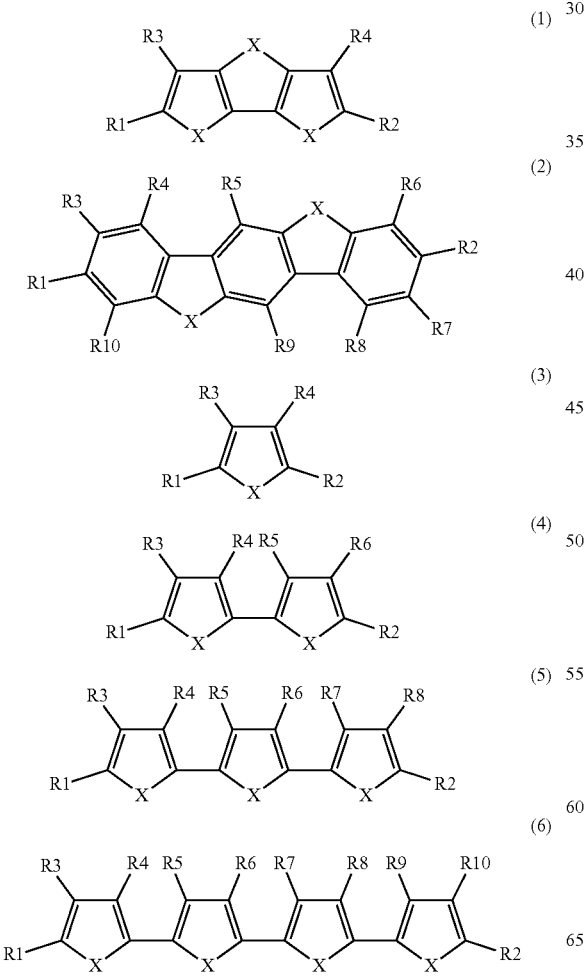

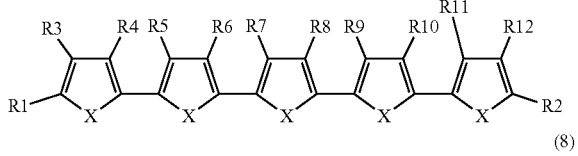

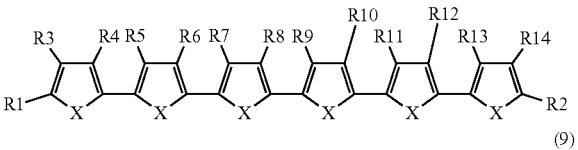

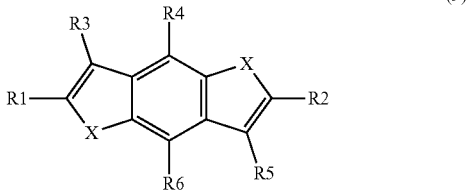

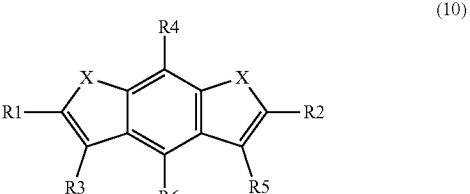

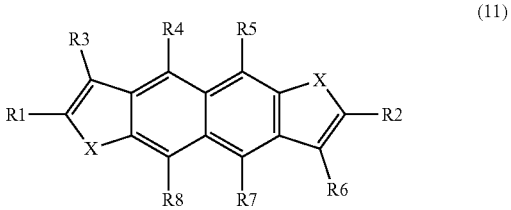

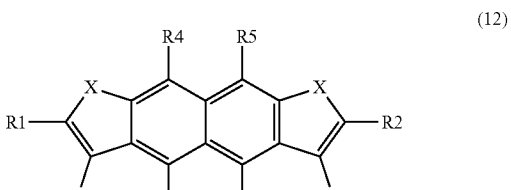

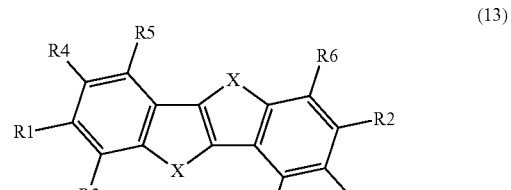

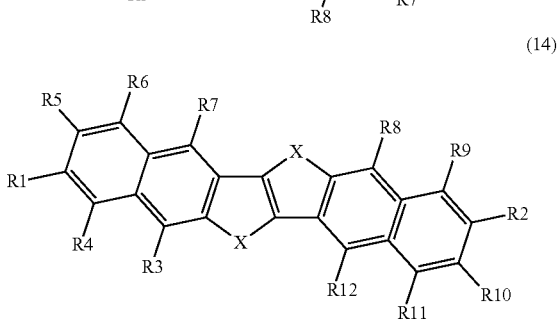

-continued

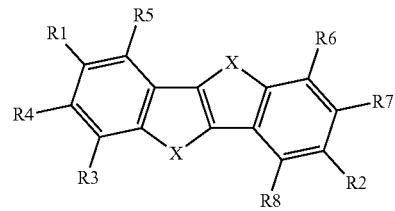
(15)

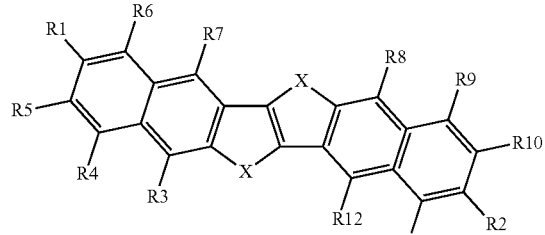
(16)

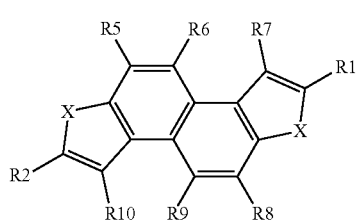
(17)

X is any of oxygen (O), sulfur (S), selenium (Se), and tellurium (Te), R1 and R2 are each independently a substituent represented by the formulae (A-1) to (A-50), where R3 to R14 are each independently a hydrogen atom, a halogen atom, a straight-chain, branched, or cyclic alkyl group, an aryl group, or a derivative thereof, where any adjacent ones of R1 to R14 may be bonded to each other to form a condensed aliphatic ring or a condensed aromatic ring, and where the condensed aliphatic ring or the condensed aromatic ring contain one or more atoms of oxygen (O), nitrogen (N), sulfur (S), selenium (Se), and tellurium (Te).

8. The photoelectric conversion device according to claim 1, wherein the one organic semiconductor material is an aromatic compound having a molecular length greater than 1.6 nanometers and equal to or smaller than 10 nanometers.

9. The photoelectric conversion device according to claim 1, wherein the one organic semiconductor material has an electron transporting property.

10. The photoelectric conversion device according to claim 9, wherein
the photoelectric conversion layer includes another organic semiconductor material,
a LUMO level of the one organic semiconductor material is lower than a LUMO level of at least one type of the other organic semiconductor material.

11. A photoelectric conversion device comprising:
a first electrode;
a second electrode opposed to the first electrode; and
a photoelectric conversion layer provided between the first electrode and the second electrode and including at least one type of one organic semiconductor material having crystallinity, wherein
variation in a ratio between horizontally-oriented crystal and vertically-oriented crystal in the photoelectric conversion layer is three times or less between a case where film formation of the one organic semiconductor material is performed at a first temperature and a case where the film formation of the one organic semiconductor material is performed at a second temperature, the second temperature being higher than the first temperature, and
wherein
the photoelectric conversion layer includes another organic semiconductor material, and
the other organic semiconductor material is subphthalocyanine or a derivative thereof represented by the following general formula (2);

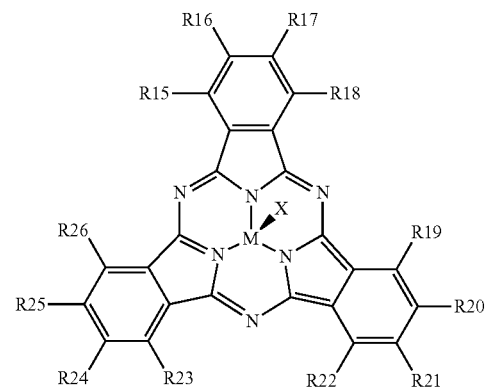
(2)

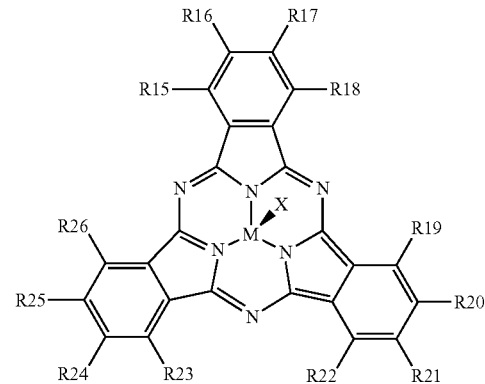
(2)

R15 to R26 are each independently selected from a group consisting of a hydrogen atom, a halogen atom, a straight-chain, branched, or cyclic alkyl group, a thioalkyl group, a thioaryl group, an arylsulfonyl group, an alkylsulfonyl group, an amino group, an alkylamino group, an arylamino group, a hydroxy group, an alkoxy group, an acylamino group, an acyloxy group, a phenyl group, a carboxy group, a carboxamide group, a carboalkoxy group, an acyl group, a sulfonyl group, a cyano group, and a nitro group, and any adjacent ones of R15 to R26 may be a portion of a condensed aliphatic ring or a condensed aromatic ring, where the condensed aliphatic ring or the condensed aromatic ring may include one or more atoms other than carbon, where M is boron, divalent metal, or trivalent metal, and where X is a substituent selected from a group consisting of halogen, a hydroxy group, a thiol group, an imide group, a substituted or unsubstituted alkoxy group, a substituted or unsubstituted aryloxy group, a substituted or unsubstituted alkyl group, a substituted or unsubstituted alkylthio group, and a substituted or unsubstituted arylthio group.

12. The photoelectric conversion device according to claim 1, wherein
the photoelectric conversion layer includes another organic semiconductor material, and
the other organic semiconductor material is fullerene or a fullerene derivative represented by the following general formula (3) or (4);

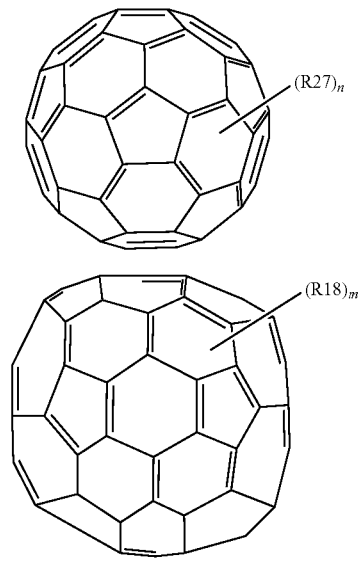

R27 and R28 are each a hydrogen atom, a halogen atom, a straight-chain, branched, or cyclic alkyl group, a phenyl group, a group having a straight-chain or condensed aromatic compound, a group having a halide, a partial fluoroalkyl group, a perfluoroalkyl group, a silylalkyl group, a silylalkoxy group, an arylsilyl group, an arylsulfanyl group, an alkylsulfanyl group, an arylsulfonyl group, an alkylsulfonyl group, an alkylsulfide group, an alkylsulfide group, an amino group, an alkylamino group, an arylamino group, a hydroxy group, an alkoxy group, an acylamino group, an acyloxy group, a carbonyl group, a carboxy group, an carboxyamino group, a carboalkoxy group, an acyl group, a sulfonyl group, a cyano group, a nitro group, a group having a chalcogenide, a phosphine group, a phosphone group, or a derivative thereof, and where "n" and "m" are each an integer of 0 or greater.

13. The photoelectric conversion device according to claim 1, wherein a variation rate of orientation between the film formation of the one organic semiconductor material at the first temperature and the film formation of the one organic semiconductor material at the second temperature in the photoelectric conversion layer is 0.9 times or greater and 2.7 times or smaller.

14. The photoelectric conversion device according to claim 1, wherein
a difference between the first temperature and the second temperature is equal to or greater than 5 degrees Celsius and equal to or smaller than 35 degrees Celsius,
the first temperature is equal to or higher than −10 degrees Celsius and equal to or lower than +10 degrees Celsius, and
the second temperature is equal to or higher than 15 degrees Celsius and equal to or lower than 35 degrees Celsius.

15. A photoelectric conversion device comprising:
a first electrode;
a second electrode opposed to the first electrode; and
a photoelectric conversion layer provided between the first electrode and the second electrode and including at least one type of one organic semiconductor material having crystallinity, wherein
a variation amount of an angle formed with an electrode surface of the first electrode is smaller than 10 degrees between a case where film formation of the one organic semiconductor material is performed at a first temperature and a case where the film formation of the one organic semiconductor material is performed at a second temperature, the second temperature being higher than the first temperature,
wherein the one organic semiconductor material has an aromatic skeleton and an aromatic substituent in a molecule, and
wherein the aromatic substituent is any of the following formulae (A-1) to (A-50):

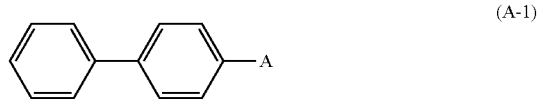

(A-1)

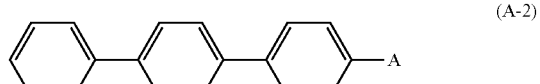

(A-2)

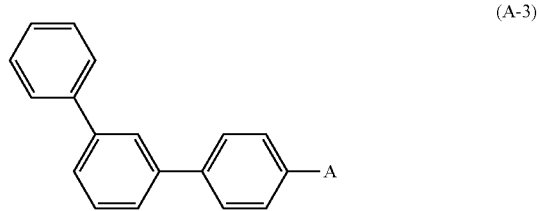

(A-3)

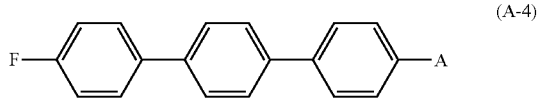

(A-4)

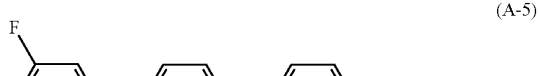

(A-5)

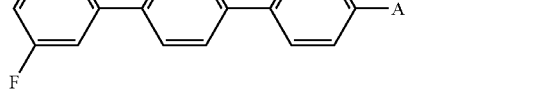

(A-6)

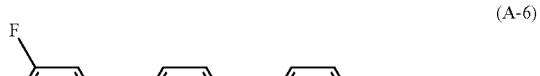

(A-7)

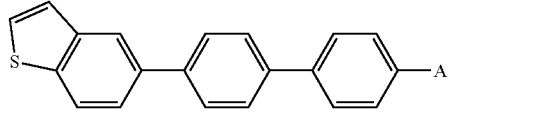

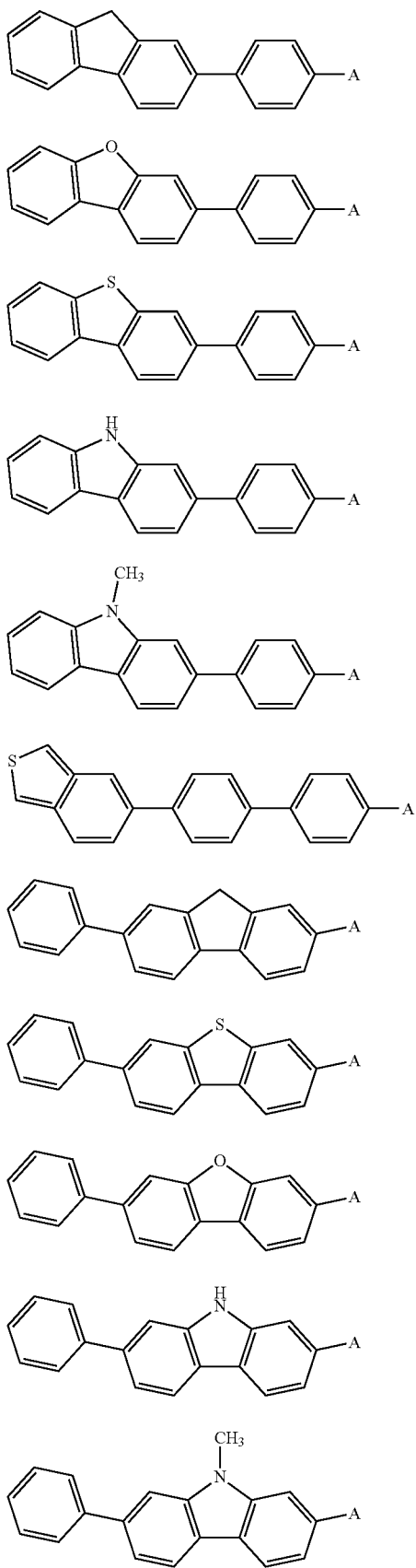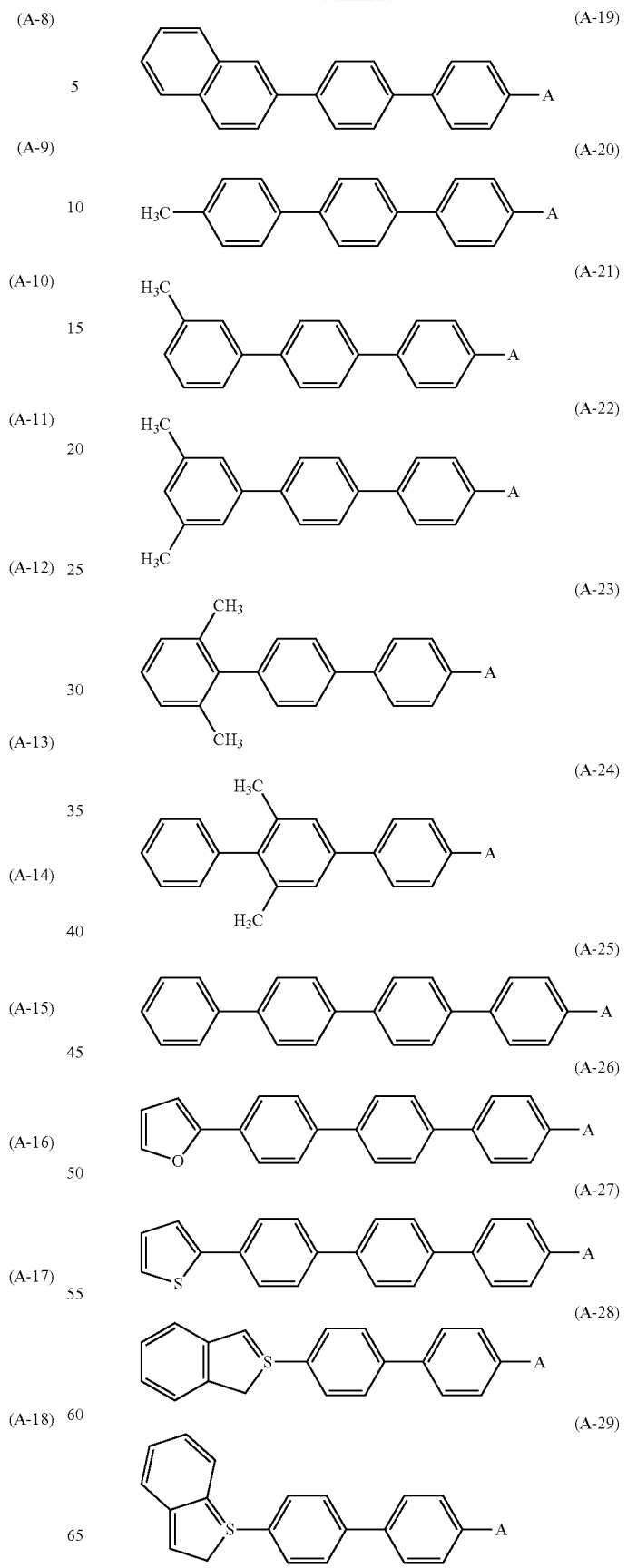

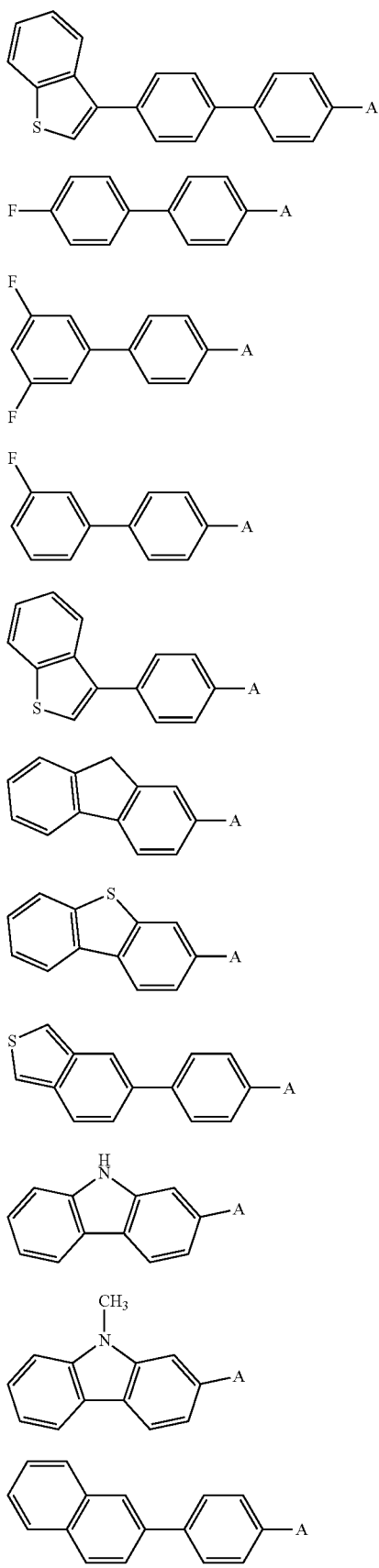
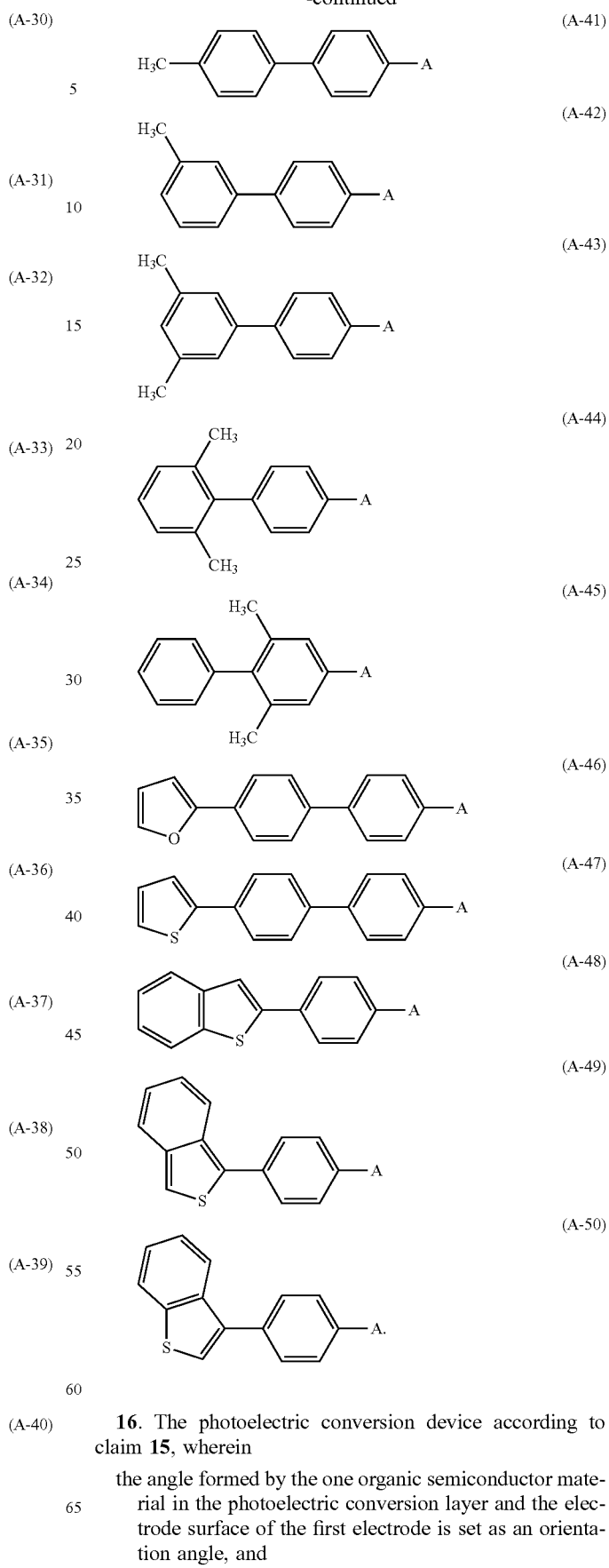
16. The photoelectric conversion device according to claim 15, wherein
the angle formed by the one organic semiconductor material in the photoelectric conversion layer and the electrode surface of the first electrode is set as an orientation angle, and an angle range of the orientation angle of the one organic semiconductor material in the photoelectric conversion layer is smaller than 46 degrees.

17. An imaging apparatus in which each pixel includes one or a plurality of organic photoelectric conversion sections,
the organic photoelectric conversion section comprising:
a first electrode;
a second electrode opposed to the first electrode; and
a photoelectric conversion layer provided between the first electrode and the second electrode and including at least one type of one organic semiconductor material having crystallinity, wherein
variation in a ratio between horizontally-oriented crystal and vertically-oriented crystal in the photoelectric conversion layer is three times or less between a case where film formation of the one organic semiconductor material is performed at a first temperature and a case where the film formation of the one organic semiconductor material is performed at a second temperature, the second temperature being higher than the first temperature,
wherein the one organic semiconductor material has an aromatic skeleton and an aromatic substituent in a molecule, and
wherein the aromatic substituent is any of the following formulae (A-1) to (A-50):

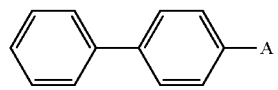 (A-1)

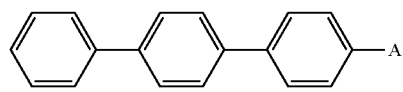 (A-2)

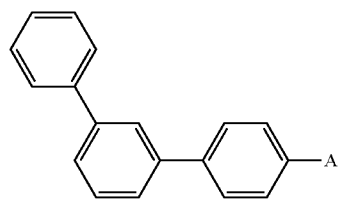 (A-3)

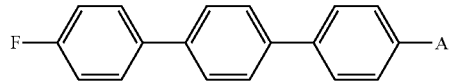 (A-4)

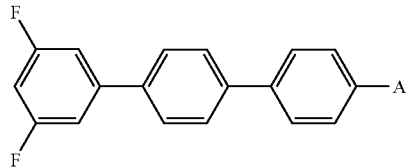 (A-5)

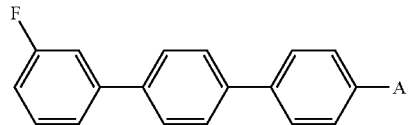 (A-6)

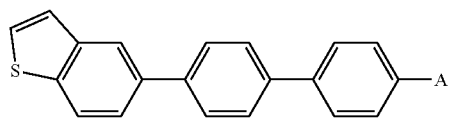 (A-7)

-continued

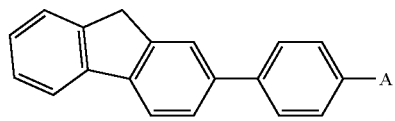 (A-8)

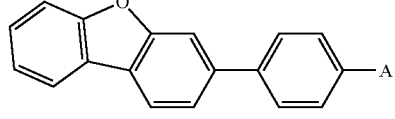 (A-9)

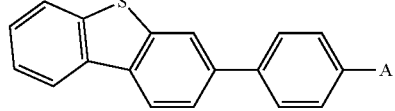 (A-10)

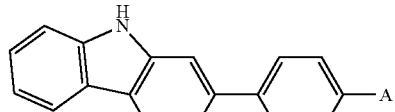 (A-11)

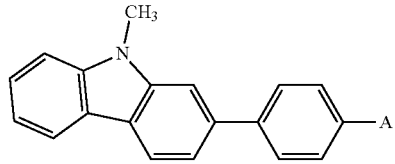 (A-12)

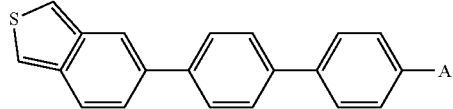 (A-13)

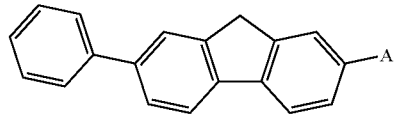 (A-14)

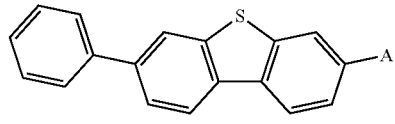 (A-15)

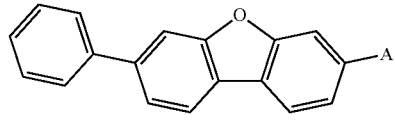 (A-16)

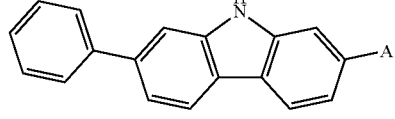 (A-17)

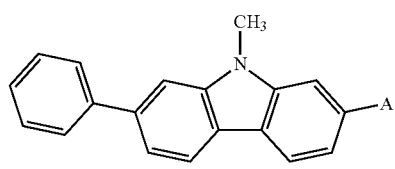 (A-18)

(A-19)
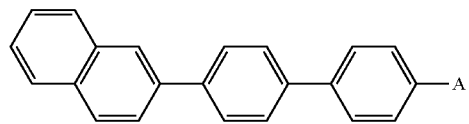
(A-20)
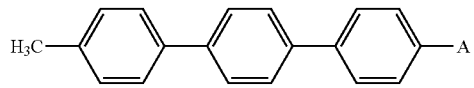
(A-21)
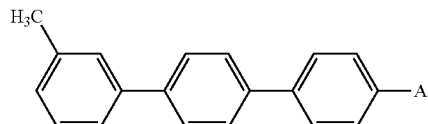
(A-22)
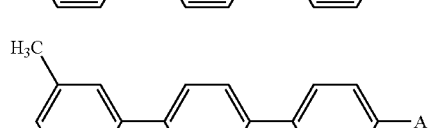
(A-23)
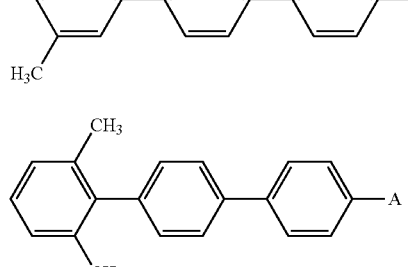
(A-24)
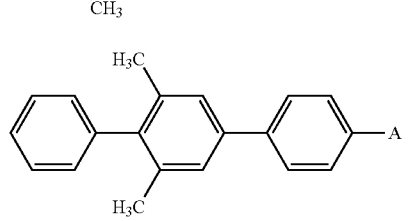
(A-25)
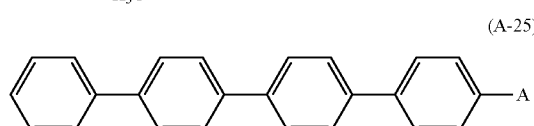
(A-26)
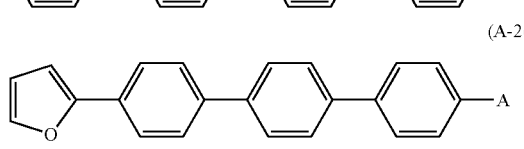
(A-27)
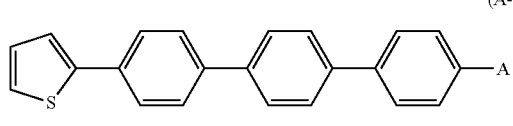
(A-28)
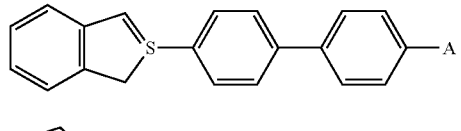
(A-29)
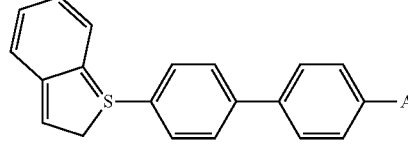
(A-30)
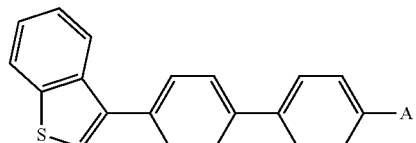
(A-31)
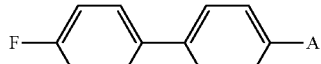
(A-32)
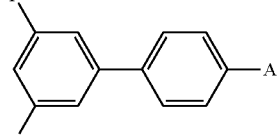
(A-33)
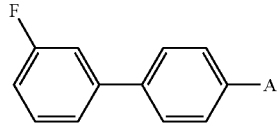
(A-34)
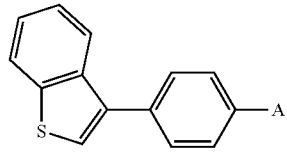
(A-35)
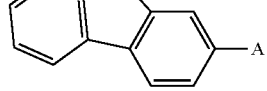
(A-36)
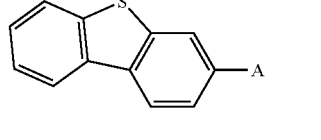
(A-37)
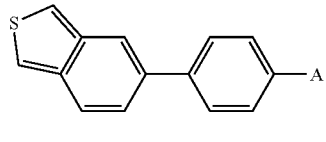
(A-38)
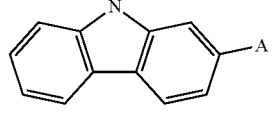
(A-39)
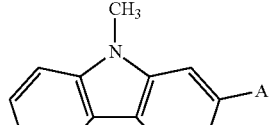
(A-40)

-continued

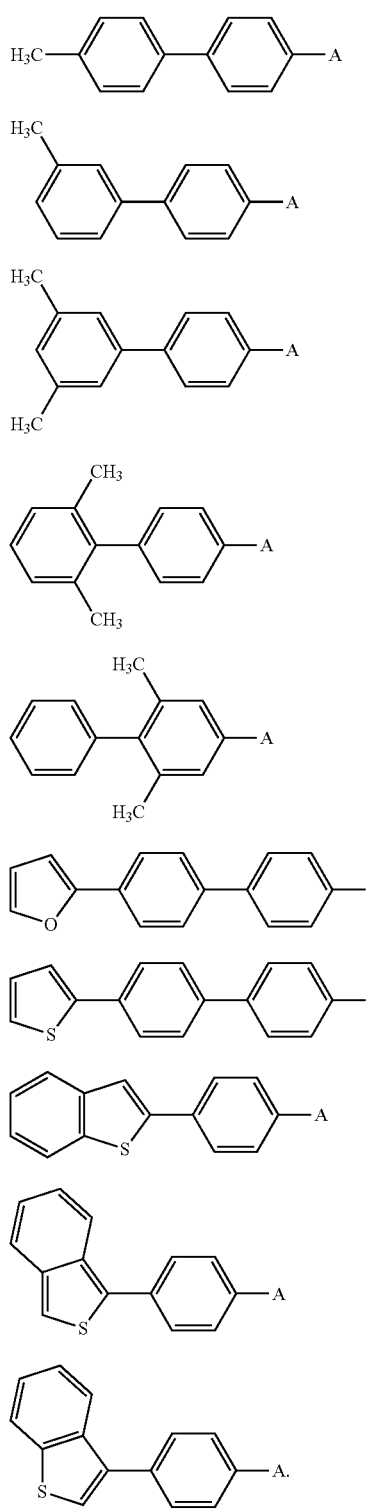

18. An imaging apparatus in which each pixel includes one or a plurality of organic photoelectric conversion sections, the photoelectric conversion device comprising:
a first electrode;
a second electrode opposed to the first electrode; and
a photoelectric conversion layer provided between the first electrode and the second electrode and including at least one type of one organic semiconductor material having crystallinity, wherein a variation amount of an angle formed with an electrode surface of the first electrode is smaller than 10 degrees between a case where film formation of the one organic semiconductor material is performed at a first temperature and a case where the film formation of the one organic semiconductor material is performed at a second temperature, the second temperature being higher than the first temperature, wherein the one organic semiconductor material has an aromatic skeleton and an aromatic substituent in a molecule, and wherein the aromatic substituent is any of the following formulae (A-1) to (A-50):

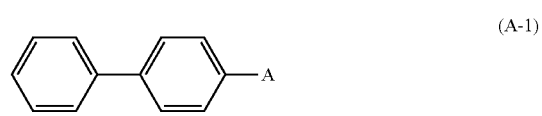

(A-1)

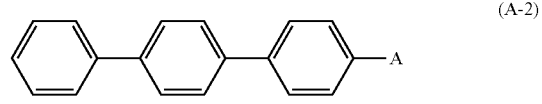

(A-2)

(A-3)

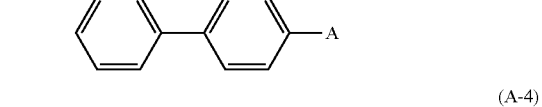

(A-4)

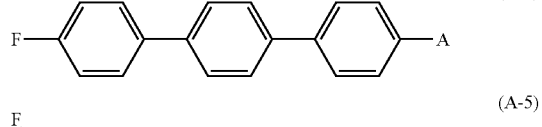

(A-5)

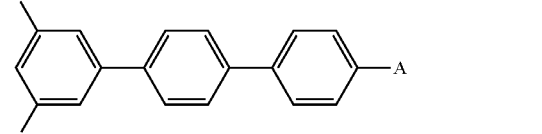

(A-6)

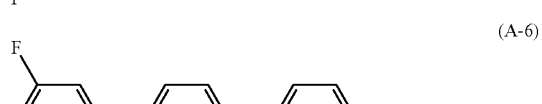

(A-7)

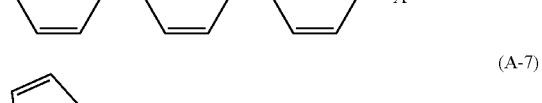

(A-8)

(A-9) 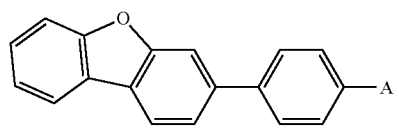
(A-10) 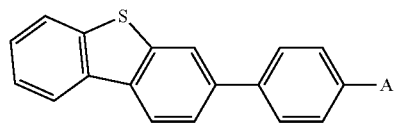
(A-11) 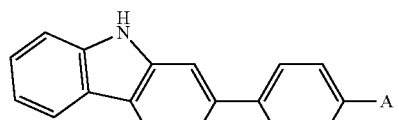
(A-12) 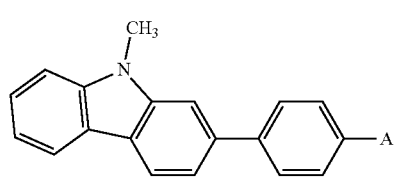
(A-13) 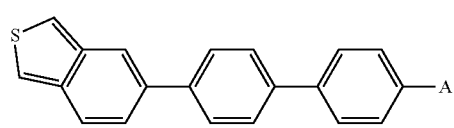
(A-14) 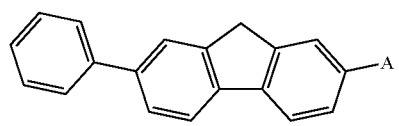
(A-15) 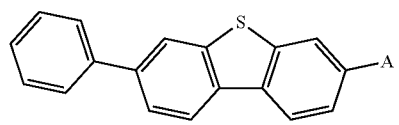
(A-16) 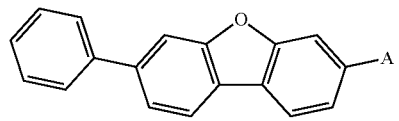
(A-17) 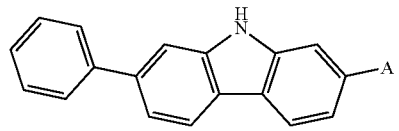
(A-18) 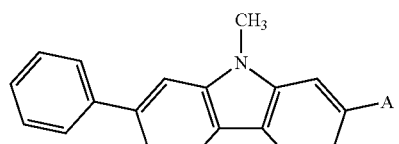
(A-19) 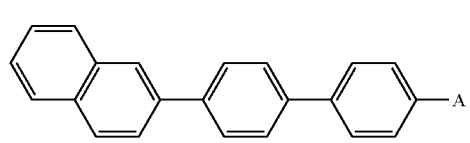
(A-20) 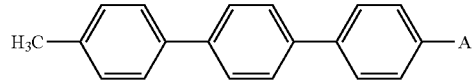
(A-21) 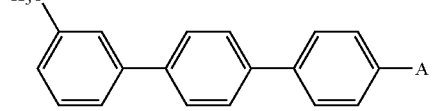
(A-22) 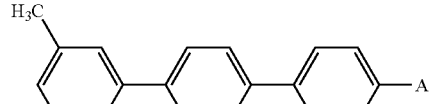
(A-23) 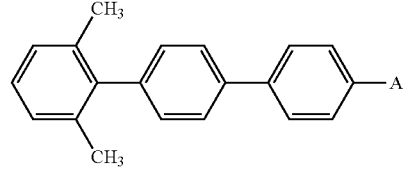
(A-24) 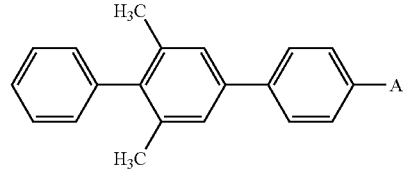
(A-25) 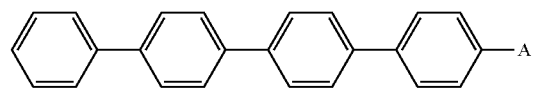
(A-26) 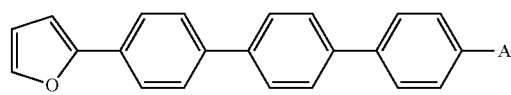
(A-27) 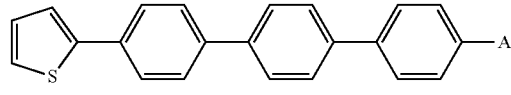
(A-28) 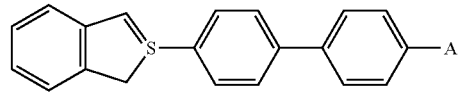
(A-29) 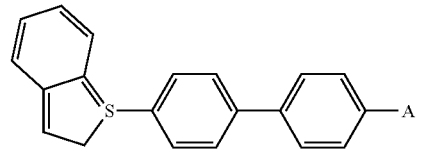
(A-30) 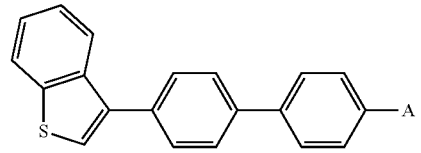

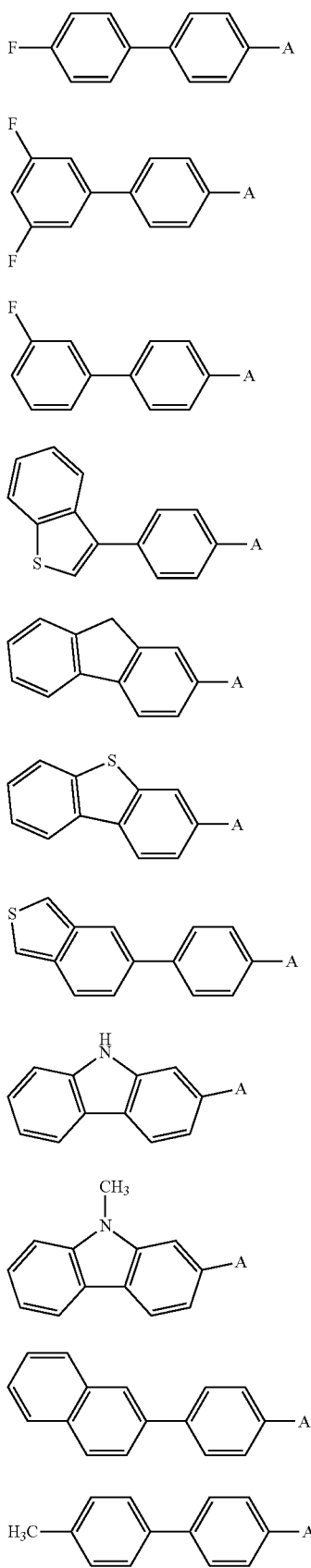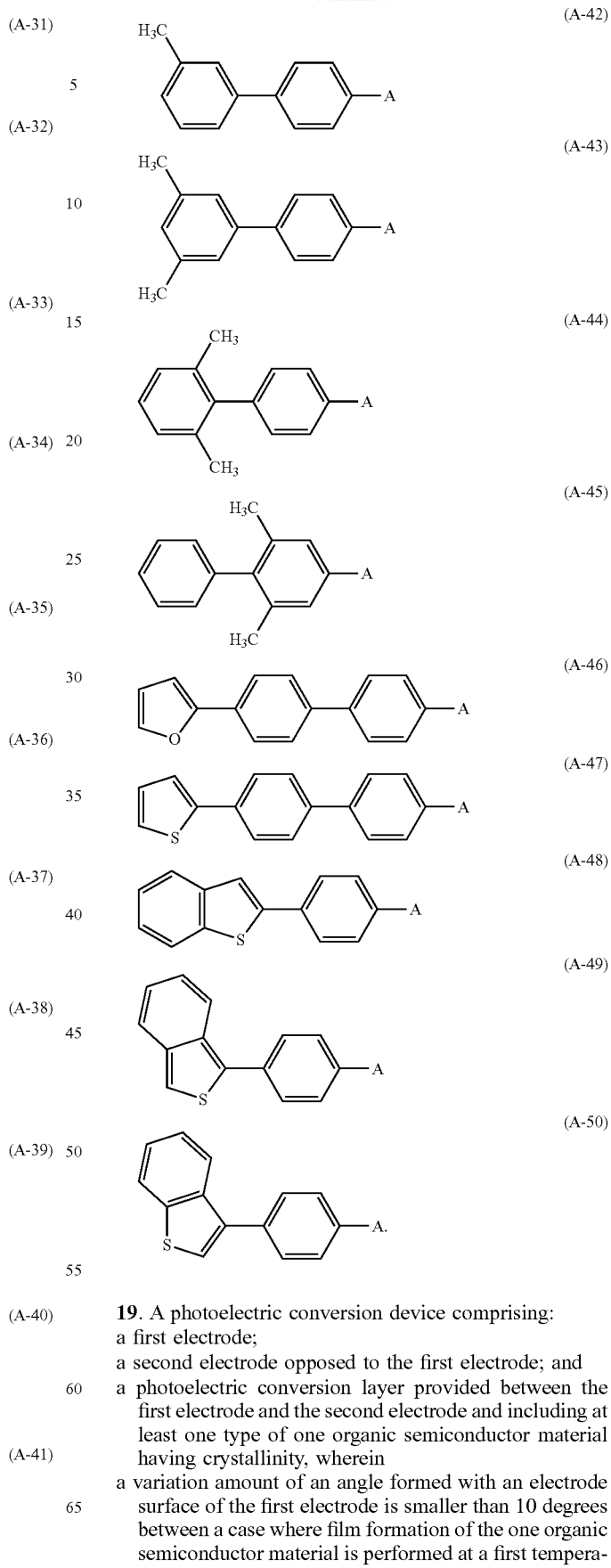

19. A photoelectric conversion device comprising:
a first electrode;
a second electrode opposed to the first electrode; and
a photoelectric conversion layer provided between the first electrode and the second electrode and including at least one type of one organic semiconductor material having crystallinity, wherein
a variation amount of an angle formed with an electrode surface of the first electrode is smaller than 10 degrees between a case where film formation of the one organic semiconductor material is performed at a first temperature and a case where the film formation of the one organic semiconductor material is performed at a second temperature, the second temperature being higher than the first temperature, wherein the photoelectric conversion layer includes another organic semiconductor material, and wherein the other organic semiconductor material is subphthalocyanine or a derivative thereof represented by the following general formula (2):

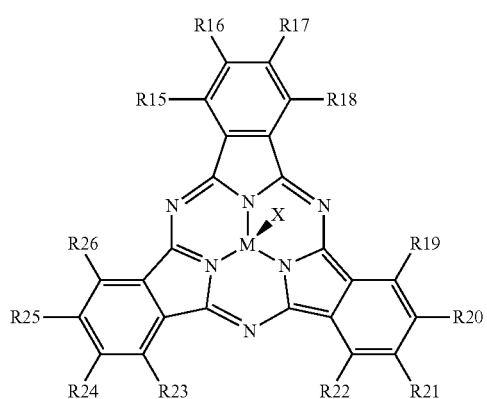

(2)

R15 to R26 are each independently selected from a group consisting of a hydrogen atom, a halogen atom, a straight-chain, branched, or cyclic alkyl group, a thioalkyl group, a thioaryl group, an arylsulfonyl group, an alkylsulfonyl group, an amino group, an alkylamino group, an arylamino group, a hydroxy group, an alkoxy group, an acylamino group, an acyloxy group, a phenyl group, a carboxy group, a carboxamide group, a carboalkoxy group, an acyl group, a sulfonyl group, a cyano group, and a nitro group, and any adjacent ones of R15 to R26 may be a portion of a condensed aliphatic ring or a condensed aromatic ring, where the condensed aliphatic ring or the condensed aromatic ring may include one or more atoms other than carbon, where M is boron, divalent metal, or trivalent metal, and where X is a substituent selected from a group consisting of halogen, a hydroxy group, a thiol group, an imide group, a substituted or unsubstituted alkoxy group, a substituted or unsubstituted aryloxy group, a substituted or unsubstituted alkyl group, a substituted or unsubstituted alkylthio group, and a substituted or unsubstituted arylthio group.

20. An imaging apparatus in which each pixel includes one or a plurality of organic photoelectric conversion sections, the organic photoelectric conversion section comprising:
a first electrode;
a second electrode opposed to the first electrode; and
a photoelectric conversion layer provided between the first electrode and the second electrode and including at least one type of one organic semiconductor material having crystallinity, wherein
variation in a ratio between horizontally-oriented crystal and vertically-oriented crystal in the photoelectric conversion layer is three times or less between a case where film formation of the one organic semiconductor material is performed at a first temperature and a case where the film formation of the one organic semiconductor material is performed at a second temperature, the second temperature being higher than the first temperature, wherein the photoelectric conversion layer includes another organic semiconductor material, and wherein the other organic semiconductor material is subphthalocyanine or a derivative thereof represented by the following general formula (2):

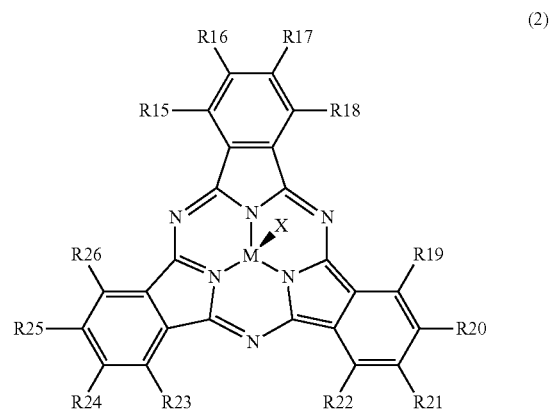

(2)

R15 to R26 are each independently selected from a group consisting of a hydrogen atom, a halogen atom, a straight-chain, branched, or cyclic alkyl group, a thioalkyl group, a thioaryl group, an arylsulfonyl group, an alkylsulfonyl group, an amino group, an alkylamino group, an arylamino group, a hydroxy group, an alkoxy group, an acylamino group, an acyloxy group, a phenyl group, a carboxy group, a carboxamide group, a carboalkoxy group, an acyl group, a sulfonyl group, a cyano group, and a nitro group, and any adjacent ones of R15 to R26 may be a portion of a condensed aliphatic ring or a condensed aromatic ring, where the condensed aliphatic ring or the condensed aromatic ring may include one or more atoms other than carbon, where M is boron, divalent metal, or trivalent metal, and where X is a substituent selected from a group consisting of halogen, a hydroxy group, a thiol group, an imide group, a substituted or unsubstituted alkoxy group, a substituted or unsubstituted aryloxy group, a substituted or unsubstituted alkyl group, a substituted or unsubstituted alkylthio group, and a substituted or unsubstituted arylthio group.

21. An imaging apparatus in which each pixel includes one or a plurality of organic photoelectric conversion sections, the photoelectric conversion device comprising:
a first electrode;
a second electrode opposed to the first electrode; and
a photoelectric conversion layer provided between the first electrode and the second electrode and including at least one type of one organic semiconductor material having crystallinity, wherein
a variation amount of an angle formed with an electrode surface of the first electrode is smaller than 10 degrees between a case where film formation of the one organic semiconductor material is performed at a first temperature and a case where the film formation of the one organic semiconductor material is performed at a second temperature, the second temperature being higher than the first temperature, wherein the photoelectric conversion layer includes another organic semiconductor material, and
wherein the other organic semiconductor material is subphthalocyanine or a derivative thereof represented by the following general formula (2):

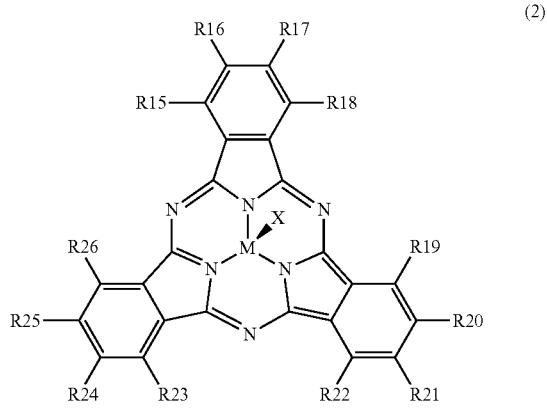

(2)

R15 to R26 are each independently selected from a group consisting of a hydrogen atom, a halogen atom, a straight-chain, branched, or cyclic alkyl group, a thioalkyl group, a thioaryl group, an arylsulfonyl group, an alkylsulfonyl group, an amino group, an alkylamino group, an arylamino group, a hydroxy group, an alkoxy group, an acylamino group, an acyloxy group, a phenyl group, a carboxy group, a carboxamide group, a carboalkoxy group, an acyl group, a sulfonyl group, a cyano group, and a nitro group, and any adjacent ones of R15 to R26 may be a portion of a condensed aliphatic ring or a condensed aromatic ring, where the condensed aliphatic ring or the condensed aromatic ring may include one or more atoms other than carbon, where M is boron, divalent metal, or trivalent metal, and where X is a substituent selected from a group consisting of halogen, a hydroxy group, a thiol group, an imide group, a substituted or unsubstituted alkoxy group, a substituted or unsubstituted aryloxy group, a substituted or unsubstituted alkyl group, a substituted or unsubstituted alkylthio group, and a substituted or unsubstituted arylthio group.

\* \* \* \* \*